United States Patent [19]

Bard et al.

[11] Patent Number: 5,714,381
[45] Date of Patent: Feb. 3, 1998

[54] DNA ENCODING HUMAN ALPHA 1 ADRENERGIC RECEPTORS AND USES THEREOF

[75] Inventors: Jonathan A. Bard, Wyckoff; Carlos Forray, Waldwick, both of N.J.; Richard L. Weinshank, New York, N.Y.

[73] Assignee: Synaptic Pharmaceutical Corporation, Paramus, N.J.

[21] Appl. No.: 468,939

[22] Filed: Jun. 6, 1995

Related U.S. Application Data

[63] Continuation of Ser. No. 334,698, Nov. 4, 1994, Pat. No. 5,556,753, which is a continuation of Ser. No. 952,798, Sep. 25, 1992, abandoned.

[51] Int. Cl.⁶ ............... C12N 5/10; C12N 15/12; C12N 15/79; C12N 15/63
[52] U.S. Cl. ............ 435/325; 435/356; 435/320.1; 435/252.3; 435/254.11; 435/69.1; 536/23.5
[58] Field of Search .................. 435/69.1, 240.2, 435/320.1, 325, 252.3, 254.11, 356; 536/22.1, 23.5, 23.1; 530/350

[56] References Cited

PUBLICATIONS

Voight, M.M. et al., Nucleic Acids Res. 1990 18:1053.
Schwinn, D.A. et al., J. Biol. Chem. 1990 265:8183–8189.
Lomasney, J.W. et al., J. Biol. Chem. 1991 266:6365–6369.
Bruno, J.F. et al., Biochem. Biophys. Res. Co . 1991 179: 1485–1490.
Weinshank, R.L. et al., Proc. Natl. Acad. Sci. USA 1992 89:3630–3634.
Schwinn, D.A. et al., Eur. J. Pharmacol. 1992 227: 433–436.
Adham N., et al., Proc. Natl. Acad. Sci. USA 1993 90:408–412.
Laz, T.M. et al., Molecular Pharmacol. 1994 46:414–422.
Forray, C., et al., Molecular Pharmacol. 1994 45:703–708.

*Primary Examiner*—Robert A. Wax
*Assistant Examiner*—Gabriele E. Bugaisky
*Attorney, Agent, or Firm*—John P. White

[57] ABSTRACT

This invention provides an isolated nucleic acid molecule encoding a human $\alpha_{1c}$ adrenergic receptor.

14 Claims, 35 Drawing Sheets

FIG. 1A

| FIG. 1A |
|---------|
| FIG. 1B |
| FIG. 1C |
| FIG. 1D |
| FIG. 1E |
| FIG. 1F |
| FIG. 1G |
| FIG. 1H |
| FIG. 1I |

Human alpha1a

```
        -170              -150              -130             -117
         .                 .                 .
-176  CCGGGCCAGGCACGTCCGCTCTCGGACAGCCGCTCNGCGTCACAGGAACTTGGGCAGGAC

-110               -90               -70              -57
         .                 .                 .
-116  CCGACGGGACCCCGTGCGGAGCTGCATCTGGAGCCCCGGCTATGCCCTGTGCTCCCC

-50               -30               -10               3
         .                 .                 .                 M
 -56  TCCTGCCGGCCGCTCGTTCTGTGCCCCCGGCCACCGACGGCCCGCGCGTTGAGATG
 -18                                                            1

10                30                50               63
           .                 .                 .
   4  ACTTTCCGCGATCTCCTGAGCGTCAGTTTCGAGGACCCCGCCCCGGACAGCAGCGCAGGG
   2   T  F  R  D  L  L  S  V  S  F  E  G  P  R  P  D  S  S  A  G    21
```

FIG. 1B

```
 64  GGCTCCAGCGGCGGGGGCGGGGGCAGCGGCGGGGCGCCCCTCGGAGGCCCG  123
 22  G  S  S  A  G  G  G  G  G  S  A  G  G  A  A  P  S  E  G  P   41
                    70              90             110

124  GCGGTGGGCGGCGTGCCGGGGGGAGGGGGCGCGGCGTGGTGGGCGCAGGCAGC  183
 42  A  V  G  G  V  P  G  G  A  G  G  G  G  V  V  G  A  G  S   61
                   130             150             170

184  GGCGAGGACAACCGGAGCTCCGCGGGAGCCCGGGGAGCCGGGGCGGGCGACGTG  243
 62  G  E  D  N  R  S  S  A  G  E  P  G  S  A  G  A  G  D  V   81
                   190             210             230

244  AATGGCACGGCCGTCGGGGACTGGTGTGAGCCGCAGGTGAGCGCTGGGCCGTC  303
 82  N  G  T  A  A  V  G  G  L  V  V  S  A  Q  G  V  G  V  V  101
                   250             270             290
```

FIG. 1C

```
304  TTCCTGGCAGCCTTCATCCTTATGGCCGTGGCAGGTAACCTGCTGTCATCCTCTCAGTG  363
102   F  L  A  A  F  I  L  M  A  V  A  G  N  L  L  V  I  L  S  V   121

364  GCCTGCAACCGCCACCTGCAGACCGTCACCAACTATTTCATCGTGAACCTGGCCGTGGCC  423
122   A  C  N  R  H  L  Q  T  V  T  N  Y  F  I  V  N  L  A  V  A   141

424  GACCTGCTGCTGAGCGCCACCGTACTGCCCTTCTCGGCCACCATGGAGGTTCTGGGCTTC  483
142   D  L  L  L  S  A  T  V  L  P  F  S  A  T  M  E  V  L  G  F   161

484  TGGGCCTTTGGCCGCGCCTTCTGCGACGTATGGGCCGCGGTGGACGTGCTGTGCTGCACG  543
162   W  A  F  G  R  A  F  C  D  V  W  A  A  V  D  V  L  C  C  T   181
```

FIG. 1D

```
544  GCCTCCATCCTCAGCCTCTGCACCATCTCCGTGGACCGTGTACGTGGGCGTGCGCCACTCA  603
182   A  S  I  L  S  L  C  T  I  S  V  D  R  Y  V  G  V  R  H  S   201

604  CTCAAGTACCCAGCCATCATGACCGAGCGCAAGGCGGCCGCCATCCTGGCCCTGCTCTGG  663
202   L  K  Y  P  A  I  M  T  E  R  K  A  A  A  I  L  A  L  L  W   221

664  GTCGTAGCCCTGGTGGTCCGTAGGCCCCTGCTGGGCTGGAAGGAGCCCGTGCCCCCT     723
222   V  V  A  L  V  V  S  V  G  P  L  L  G  W  K  E  P  V  P  P   241

724  GACGAGCGCTTCTGCGGTATCACCGAGGAGGCGGGCTACGCTGTCTTCTCCTCCGTGTGC  783
242   D  E  R  F  C  G  I  T  E  E  A  G  Y  A  V  F  S  S  V  C   261
```

FIG. 1E

```
         790                810                830
784  TCCTTCTACCTGCCCATGGGCGGTGTCATCGTGGTCATGTACTGCCGCGTGTACGTGGTCGCG  843
262   S  F  Y  L  P  M  A  V  I  V  V  M  Y  C  R  V  Y  V  V  A    281

850                870                890
844  CGCAGCACCACCCGCGGCAGCCTCGAGGCCGGAGGCGTCAAGGCGAGGCAAGGCCTCCGAG  903
282   R  S  T  T  R  S  L  E  A  G  V  K  R  E  R  G  K  A  S  E   301

910                930                950
904  GTGGTGCTGCGCCATCCACTGTCGCGGGCCCACGGGCGGCCACGGCATG  963
302   V  V  L  R  I  H  C  R  G  A  A  T  G  A  D  G  A  H  G  M   321

970                990               1010
964  CGCAGCGCCAAGGGCCACACCTTCCGCAGCTCGCTCTCCGTGCGCTCAAGTTCTCC  1023
322   R  S  A  K  G  H  T  F  R  S  S  L  S  V  R  L  L  K  F  S   341
```

FIG. 1F

```
1024  CGTGAGAAGAAGCGGCCAAGACTCTGGCCATCGTCGTGGGTGTCTTCGTGCTCTGCTGG  1083
 342   R   E   K   K   A   A   K   T   L   A   I   V   V   G   V   F   V   L   C   W   361

1084  TTCCCTTTCTTCTTTGTCCTGCCTCCTTGGGCTCGCCTCCTGGTTCCCGGCAGCTGAAGCCATCGGAG  1143
 362   F   P   F   F   F   V   L   P   L   G   S   L   F   P   Q   L   K   P   S   E   381

1144  GGCGTCTTCAAGGTCATCTTCTGGCTCGGCTACTTCAACAGCTGCGTGAACCCGCTCATC  1203
 382   G   V   F   K   V   I   F   W   L   G   Y   F   N   S   C   V   N   P   L   I   401

1204  TACCCCTGTTCCAGCCGGGAGTTCAAGCGGCGCGCCTTCCTCCGGCTGCTGCGCCAGTGC  1263
 402   Y   P   C   S   S   R   E   F   K   R   R   A   F   L   R   L   L   R   C   Q   C   421
```

FIG. 1G

```
1264  CGTCGTGCCGGCCCGCGCCTCTCTGGCGTGTCTACGGCCACCACTGGCGGGCCTCC  1323
422   R  R  R  R  R  R  P  L  W  R  V  Y  G  H  H  W  R  A  S    441

1324  ACCAGCGGCCTGCGCCAGGACTGCGCCCCGAGTTCGGGGACGCGCCCCCGGAGCCCG  1383
442   T  S  G  L  R  Q  D  C  A  P  S  S  G  D  A  P  P  G  A  P  461

1384  CTGGCCCTCACCGCTCCCCGACCCCGAACCCCAGGCCCGGAGGTACCCGAGATGCAG  1443
462   L  A  L  T  A  L  P  D  D  P  E  P  P  P  G  T  P  E  M  Q  481

1444  GCTCCGGTCGCCAGCCGTCGAAAGCCACCCAGCCTTCCGGCAGTGGAGGCTGCTGGGG  1503
482   A  P  V  A  S  R  R  K  P  P  S  A  F  R  E  W  R  L  L  G  501
```

FIG. 1H

```
1504  CCGTTCCGGAGACCCAGCGACCCCAGCTGCGCGCCAAAGTCTCCAGCCTGTCGCACAAGATC  1563
 502   P  F  R  R  P  T  T  Q  L  R  A  K  V  S  S  L  S  H  K  I   521
              1510           1530              1550

1564  CGCGCCGGGGGCGCGCAGCGCCAGAGGCAGCGCCCAGCGTGCGCCCAGCGCTCAGAGGTGGAGGCT  1623
 522   R  A  G  G  A  Q  R  A  E  A  A  C  A  Q  R  S  E  V  E  A   541
              1570           1590              1610

1624  GTGTCCCTAGGCGTCCCACACGAGGTGGCCGAGGGCGCCACCTGCCAGGCCTACGAATTG  1683
 542   V  S  L  G  V  P  H  E  V  A  E  G  A  T  C  Q  A  Y  E  L   561
              1630           1650              1670

1684  GCCGACTACAGCAACCTACGGGAGACCGATATTTAAGGACCCCAGAGCTAGGCCCGCGGAG  1743
 562   A  D  Y  S  N  L  R  E  T  D  I  *                            572
              1690           1710              1730
```

FIG. 1I

```
                  1750                    1770                1790
                   .                       .                   .
1744    TGTGCTGGGCTTGGGGGTAAGGGGGACCAGAGAGGGCGGGCTGGTGTTCTAAGAGCCCCCG    1803

1810                    1830                1850
                   .                       .                   .
1804    TGCAAATCGGAGACCCGGAAACTGATCAGGGCCAGCTGCTCTGTGACATCCCTGAGGAACT    1863

1870                    1890                1910
                   .                       .                   .
1864    GGGCAGAGCTTGAGGCTTGAGGCCCTTGAAAGGTGAAAAGTAGTGGGCCCCTGCTGGAC    1923

1930                    1950
                   .                       .
1924    TCAGGTGCCCCAGAACTCTTTTCTTAGAAGGGGAGAGGCTGC    1963
```

FIG. 2A

| FIG. 2A |
|---|
| FIG. 2B |
| FIG. 2C |
| FIG. 2D |
| FIG. 2E |
| FIG. 2F |
| FIG. 2G |
| FIG. 2H |

Human alpha1b

```
            -120                     -100                    -80
-122   GCCAGGAGGGCGCCTCTGGGAAGAAGACCACGGGGGAAGCAAAGTTTCAGGGCAGCTGAG    -63

-60                      -40                     -20
 -62   GAGCCTTCGCCCGCAGCCCCTTCCGAGCCCCAATCATCCCCCAGGCTATGGAGGGGACTCT     -3

0                       20                     40
  -2   AAGATGAATCCCGACCTGGACACCGGCCACAACACATCAGCACCTGCCCACTGGGGAGAG     57
   0    K  M  N  P  D  L  D  T  G  H  N  T  S  A  P  A  H  W  G  E     19

60                       80                    100
  58   TTGAAAAATGCCAACTTCACTGGCCCCAACCAGACCTCGAGCAACTCCACACTGCCCCAG    117
  20    L  K  N  A  N  F  T  G  P  N  Q  T  S  S  N  S  T  L  P  Q     39
```

FIG. 2B

```
          120              140              160
          .                .                .
118  CTGGACATCACCAGGGCCATCTCTGTGGGCCTGGTGCTGGGCGCCTTCATCCTTCTTTGCC  177
 40  L   D   I   T   R   A   I   S   V   G   L   V   L   G   A   F   I   L   F   A   59

180              200              220
          .                .                .
178  ATCGTGGGCAACATCCTAGTCATCTTGTCTGTGGCCTGCAACCGGCACCTGCGGACGCCC  237
 60  I   V   G   N   I   L   V   I   L   S   V   A   C   N   R   H   L   R   T   P   79

240              260              280
          .                .                .
238  ACCAACTACTTCATTGTCAACCTGGCCATGGCCGACCTGCTGTTGAGCTTCACCGTCCTG  297
 80  T   N   Y   F   I   V   N   L   A   M   A   D   L   L   L   S   F   T   V   L   99

300              320              340
          .                .                .
298  CCCTTCTCAGCGGCCCTAGAGGTGCTCGGCTACTGGGTGCTGGGGCGGATCTTCTGTGAC  357
100  P   F   S   A   A   L   E   V   L   G   Y   W   V   L   G   R   I   F   C   D   119
```

FIG. 2C

```
     360                                       380                                       400
358  ATCTGGGCAGCCGTGGATGTCCTGTGCTGCACAGGCGTCCATTCTGAGCCTGTGCGCCATC  417
120   I  W  A  A  V  D  V  L  C  C  T  A  S  I  L  S  L  C  A  I   139

420                                       440                                       460
418  TCCATCGATCGCTACATCGGGGTGCGCTACTCTCTGCAGTATCCCACGCTGGTCACCCGG  477
140   S  I  D  R  Y  I  G  V  R  Y  S  L  Q  Y  P  T  L  V  T  R   159

480                                       500                                       520
478  AGGAAGGCCATCTTGGCGCTGCTCAGTGTCTGGGTCTTGTCCACCGTCATCTCCATCGGG  537
160   R  K  A  I  L  A  L  L  S  V  W  V  L  S  T  V  I  S  I  G   179

540                                       560                                       580
538  CCTCTCCTTGGGTGGAAGGAGCCGGCACCCAACGATGACAAGGAGTGCGGGGTCACCGAA  597
180   P  L  L  G  W  K  E  P  A  P  N  D  D  K  E  C  G  V  T  E   199
```

FIG. 2D

```
                 600                   620                   640
598  GAACCCTTCTATGCCCTCTTCTCCTCTCTGGGCTCCTTCTACATCCCTCTGGCCGTCATT  657
200   E  P  F  Y  A  L  F  S  S  L  G  S  F  Y  I  P  L  A  V  I   219

660                   680                   700
658  CTAGTCATGTACTGCCGTGTCTATATAGTGGCCAAGAGAACCACCAAGAACCTAGAGGCA  717
220   L  V  M  Y  C  R  V  Y  I  V  A  K  R  T  T  K  N  L  E  A   239

720                   740                   760
718  GGAGTCATGAAGGAGATGTCCAACTCCAAGGAGCTGACCCTGAGGATCCATTCCAAGAAC  777
240   G  V  M  K  E  M  S  N  S  K  E  L  T  L  R  I  H  S  K  N   259

780                   800                   820
778  TTTCACGAGGACACCCTTAGCAGTACCAAGGCCAAGGGCCACAACCCCCAGGAGTTCCATA  837
260   F  H  E  D  T  L  S  S  T  K  A  K  G  H  N  P  R  S  S  I   279
```

FIG. 2E

```
                840                  860                   880
838  GCTGTCAAACTTTTTAAGTTCTCCAGGGAAAAGAAAGCAGCTAAGACGTTGGGCATTGTG   897
280   A  V  K  L  F  K  F  S  R  E  K  K  A  A  K  T  L  G  I  V   299

900                  920                   940
898  GTCGGTATGTTCATCTTGTGCTGGCTACCCTTCTTCATCGCTCTACCGCTTGGCTCCTTG   957
300   V  G  M  F  I  L  C  W  L  P  F  F  I  A  L  P  L  G  S  L   319

960                  980                  1000
958  TTCTCCACCCTGAAGCCCCCCGACGCCGTGTTCAAGGTGGTGTTCTGGCTGGGCTACTTC  1017
320   F  S  T  L  K  P  P  D  A  V  F  K  V  V  F  W  L  G  Y  F   339

1020                 1040                  1060
1018 AACAGCTGCCTCAACCCTCATCATCTACCCCATGCTCCAGCAAGGAGTTCAAGCGGCGCTTC 1077
340   N  S  C  L  N  P  I  I  Y  P  C  S  S  K  E  F  K  R  A  F   359
```

FIG. 2F

```
        1080                1100              1120
1078  GTGGCGCATCCTCGGGGTGCCAGTGCCGCGGCCGACGCCGCCGCCGT    1137
360    V  R  I  L  G  C  Q  C  R  G  R  R  R  R  R  R  R   379

1140                1160              1180
1138  CGCCTGGGGCGGCTGCGCCTACACCTACCGGCCGTGGACGCGCTCGGAGCGC    1197
380    R  L  G  G  C  A  Y  T  Y  R  P  W  T  R  G  G  S  L  E  R   399

1200                1220              1240
1198  TCGCAGTCGCGCAAGGACTCGCTGGACGACAGCGGCAGCTGCCTGAGCGGCAGCCAGCGG    1257
400    S  Q  S  R  K  D  S  L  D  D  S  G  S  C  L  S  G  S  Q  R   419

1260                1280              1300
1258  ACCCTGCCCTCGGCCTCGCCCAGCCCCGGCTACCTGGGCCGGGCCCCGCCACCGCCAGTC    1317
420    T  L  P  S  A  S  P  S  P  G  Y  L  G  R  G  A  P  P  P  V   439
```

FIG. 2G

```
                              1320                        1340                        1360
1318  GAGCTGTGCGCCTTCCCCGAGTGGAAGGCCCCGGGCGCCCTCCTGAGCCTGCCCGCGCCT  1377
440    E   L   C   A   F   P   E   W   K   A   P   G   A   L   L   S   L   P   A   P   459

1380                        1400                        1420
1378  GAGCCCCCCGGCGGCCGCCGGGGCCGCCGCGCACGACTCGGGCCCGCTCTTCACCTTCAAGCTCCTG  1437
460    E   P   P   G   R   R   R   G   R   H   D   S   G   P   L   F   T   F   K   L   L   479

1440                        1460                        1480
1438  ACCGAGCCCGAGAGCCCCGGGACCGACGGGGGCGCCAGCAACGGAGGCTGCGAGGCCGCG  1497
480    T   E   P   E   S   P   G   T   D   G   G   A   S   N   G   G   C   E   A   A   499

1500                        1520                        1540
1498  GCCGACGTGGCCAACGGGCAGCCCGGGCTTCAAAAGCAACATGCCCCTGGCGCCCGGGCAG  1557
500    A   D   V   A   N   G   Q   P   G   F   K   S   N   M   P   L   A   P   G   Q   519
```

FIG. 2H 1558 520

TTTTAGGGCCCCCGTGCGCAGCTTTCTTTCCCTGGGAGGAAAACATCGTGGGGGGA
F  *

| FIG. 3A |
|---------|
| FIG. 3B |
| FIG. 3C |
| FIG. 3D |
| FIG. 3E |
| FIG. 3F |
| FIG. 3G |

Human alpha1c

```
-124                    -120              -100              -80               -65
     CCAGCCAAACCACTGGCAGGCTCCCCTCCAGCCGAGACCTTTTATTCCCGGCTCCCGAGCT

-64                     -60               -40               -20               -5
     CCGCCTCCGCGCCAGCCCGGGAGGTGGCCCTGACAGCCGGACCCTCGCCGGACCCCGGCTG

-4                      0                 20                40                55
   0 GGACCATGGTGTTTCTCTCGGGAAATGCTTCCGACAGCTCCAACTGCACCCAACCGCCGG   19
       M  V  F  L  S  G  N  A  S  D  S  S  N  C  T  Q  P  P  A 56                     60                 80               100               115
  20 CACCGGTGAACATTTCCAAGGCCATTCTGCTTCTCGGGGTGATCTTGGGGGCCTCATTCTTT  39
       P  V  N  I  S  K  A  I  L  L  L  G  V  I  L  G  G  L  I  L  F
```

FIG. 3B

```
                     120             140             160
                      .               .               .
116  TCGGGGTGTGCTGGGTAACATCCTAGTGATCCTCCGTAGCCTGTCACCGACACCTGCACT  175
 40   G  V  L  G  N  I  L  V  I  L  S  V  A  C  H  R  H  L  H  S   59

180             200             220
                      .               .               .
176  CAGTCACGGCACTACTACATCGTCAACCTGGGCGTGGCCGACCTCCTGCTCACCTCCACGG  235
 60   V  T  H  Y  Y  I  V  N  L  A  V  A  D  L  L  L  T  S  T  V   79

240             260             280
                      .               .               .
236  TGCTGCCCTTCTCCGCCATCTTCGAGGTCCTAGGCTACTGGGCCTTCGGCAGGGTCTTCT  295
 80   L  P  F  S  A  I  F  E  V  L  G  Y  W  A  F  G  R  V  F  C   99

300             320             340
                      .               .               .
296  GCAACATCTGGGCGGCAGTGGATGTGCTGTGCTGCACCGCGTCCATCATGGGCCTCTGCA  355
100   N  I  W  A  A  V  D  V  L  C  C  T  A  S  I  M  G  L  C  I  119
```

FIG. 3C

```
356  TCATCTCCATCGACCGGCTACATCGGCGTGAGCTACCCGCTGCGCTACCCAACCATCGTCA  415
120   I  S  I  D  R  Y  I  G  V  S  Y  P  L  R  Y  P  T  I  V  T  139

416  CCCAGAGGAGGGTCTCATGGCTCTGCTCTGCGTCTGGGCACTCTCCCTGGTCATATCCA   475
140   Q  R  R  G  L  M  A  L  L  C  V  W  A  L  S  L  V  I  S  I  159

476  TTGGACCCCTGTTCGGCTGGAGGCAGCCCGAGGACGAGACCATCTGCCAGATCA        535
160   G  P  L  F  G  W  R  Q  P  A  P  E  D  E  T  I  C  Q  I  N  179

536  ACGAGGAGCCCGGCTACGTGCTCTTCTCAGCGCTGGGCTCCTTCTACCTGCCTCTGGCCA  595
180   E  E  P  G  Y  V  L  F  S  A  L  G  S  F  Y  L  P  L  A  I  199
```

FIG. 3D

```
             600            620            640
             .              .              .
596  TCATCCTGGTCATGTACTGCCGCGTCTACGTGGTGGCCAAGAGGGAGAGCCGGGGCCTCA  655
200   I  L  V  M  Y  C  R  V  Y  V  V  A  K  R  E  S  R  G  L  K  219

660            680            700
             .              .              .
656  AGTCTGGCCTCAAGACCGACAAGAGTCGGACTCGGAGCAAGTGACGCTCCGCATCCATCGGA  715
220   S  G  L  K  T  D  K  S  D  S  E  Q  V  T  L  R  I  H  R  K  239

720            740            760
             .              .              .
716  AAAACGCCCCGGGAGGCAGGAGGCAGCGGGATGGCCAGCGCCAAGACGCCACTTCTCAG  775
240   N  A  P  A  G  G  S  G  M  A  S  A  K  T  K  T  H  F  S  V  259

780            800            820
             .              .              .
776  TGAGGCTCCTCAAGTTCTCCCGGGAGAAGAAGGCCAAAACGCTGGGCATCGTGGTCG  835
260   R  L  L  K  F  S  R  E  K  K  A  A  K  T  L  G  I  V  V  G  279
```

FIG. 3E

```
836  GCTGCTTCGTCCTCTGCTGGCTGCCTTTTTCTTAGTCATGCCCATTGGGTCTTTCTTCC  895
280    C  F  V  L  C  W  L  P  F  F  L  V  M  P  I  G  S  F  F  P   299

896  CTGATTTCAAGCCCCTCTGAAACAGTTTTTAAAATAGTATTTTGGCTCGGATATCTAAACA  955
300    D  F  K  P  S  E  T  V  F  K  I  V  F  W  L  G  Y  L  N  S   319

956  GCTGCATCAACCCCATCATATACCCATGCTCCAGCAGTTCAAAAAGGCCTTTCAGA  1015
320    C  I  N  P  I  I  Y  P  C  S  S  Q  E  F  K  K  A  F  Q  N   339

1016 ATGTCTTGAGAATCCAGTGTCTCTGCAGAAAGCAGTCTTCCAAACATGCCCTGGGCTACA  1075
340    V  L  R  I  Q  C  L  C  R  K  Q  S  S  K  H  A  L  G  Y  T   359
```

FIG. 3F

```
1076  CCCTGCACCCGCCCAGCCCAGGCCCAGGGCAACACAAGGACATGGTGCGCATCCCCG  1135
360   L   H   P   P   S   Q   A   V   E   G   Q   H   K   D   M   V   R   I   P   V   379

1136  TGGGATCAAGAGAGACCTTCTACAGGATCTCCAAGACGGATGGCGTTTGTGAATGGAAAT  1195
380   G   S   R   E   T   F   Y   R   I   S   K   T   D   G   V   C   E   W   K   F   399

1196  TTTTCTTCCATGCCCCGTGGATCTGCCAGGATTACAGTGTCCAAAGACCAATCCTCCT  1255
400   F   S   S   M   P   R   G   S   A   R   I   T   V   S   K   D   Q   S   S   C   419

1256  GTACCACAGCCCCGGGTGAGAAGTAAAAGCTTTTGCAGGTCTGCTGTGTAGGCCCT  1315
420   T   T   A   R   V   R   S   K   S   F   L   Q   V   C   C   C   V   G   P   S   439
```

FIG. 3G

```
                              1320                    1340                     1360
1316    CAACCCCCAGCCTTGACAAGAACCATCAAGTTCCAACCATTAAGGTCCACACCATCTCCC    1375
440      T  P  S  L  D  K  N  H  Q  V  P  T  I  K  V  H  T  I  S  L     459

1380                    1400                     1420
1376    TCAGTGAGAACGGGGAGGAAGTCTAGGACAGGAAAGATGCAGAGGAAAGGGGAATATCTT    1435
460      S  E  N  G  E  E  V  *                                          466

1440                    1460                     1480
1436    AGGTACCATACCCTGGAGTTCTAGAGGATTCCCTGACAAGCTTATTCCGATCCAGACATG    1495

1500
1496    ATAGATACATTGATGAGTT    1514
```

FIG. 4A

Alignment of Human and Rat Alpha-1a Adrenergic Receptors

```
                          1                                                    40
human  alpha1a   mtfrdllsvs  fegprpdssa  ggssaggggg  saggaapseg
H318/3 alpha1a   ..........  ..........  ..........  ..........
Rat    alpha1a   mtfrdilsvt  fegprsssst  gggsgagggag  tvg....peg
       Consensus MTFRD-LS--  FEGPR--SS-  GGS-AGGG-G  --G-----EG 41                                                   80
human  alpha1a   pavggvpgg-  ggggg-vga-  sgednrssa.  .....gepgs
H318/3 alpha1a   .........m  --aalrs-mma-  ylsewrtpty  rstemvqrlr
Rat    alpha1a   gavggvpg.-  tggga-vgt-  sgedngsst.  .....gepg
       Consensus -------A--  -----V---G  ----------  ----------

81                                                  120
human  alpha1a   ag-ggdvngt  ----------  ----------  ----m-----
H318/3 alpha1a   me-vqhstst  ----------  ----------  ----m-----
Rat    alpha1a   aa-sgevngs  ----------  ----------  ----t-----
       Consensus --A-------  AAVGGLVVSA  QGVGVGVFLA  AFIL-AVAGN 121                                                 160
human  alpha1a   ----------  ----------  ----------  ---t------
H318/3 alpha1a   ----------  ----------  ----------  ---t------
Rat    alpha1a   ----------  ----------  ----------  ---a------
       Consensus LLVILSVACN  RHLQTVTNYF  IVNLAVADLL  LSA-VLPFSA
```

```
                   161                                                               200
human  alpha1a     ------- ---------- ---------- --a------- ----------
H318/3 alpha1a     ------- ---------- ---------- --a------- ----------
Rat    alpha1a     ------- ---------- ---------- --t------- ----------
Consensus          TMEVLGFWAF GR-FCDVWAA VDVLCCTASI LSLCTISVDR 201                                                               240
human  alpha1a     ---------- ---------- ---------- ---v------ ----------
H318/3 alpha1a     ---------- ---------- ---------- ---v------ ----------
Rat    alpha1a     ---------- ---------- ------a--- ---------- ----------
Consensus          YVGVRHSLKY PAIMTERKAA AILALLW-VA LVVSVGPLLG 241                                                               280
human  alpha1a     ---------- ------a--- ---v------ ----------
H318/3 alpha1a     ---------- ------a--- ---v------ ----------
Rat    alpha1a     ---------- ------v--- ---i------ ----------
Consensus          WKEPVPPDER FCGITEE-GY A-FSSVCSFY LPMAVIVVMY 281                                                               320
human  alpha1a     ---------- ----v----- ---r------ ---------g
H318/3 alpha1a     ---------- ----v----- ---r------ ---------g
Rat    alpha1a     ---------- ----i----- ---p------ ---------s
Consensus          CRVYVVARST TRSLEAG-KR E-GKASEVVL RIHCRGAAT-
```

FIG. 4C

```
                        321                                                              360
human    alpha1         -d-ah-mr-a  ----f-----  ----------  ----------  ----------
H318/3   alpha1         -d-ah-mr-a  ----f-----  ----------  ----------  ----------
Rat      alpha1         -k-yp-tq-s  ----l-----  ----------  ----------  ----------
         Consensus      A-G--G---S  KGHT-RSSLS  VRLLKFSREK  KAAKTLAIVV 361                                                              400
human    alpha1         ----------  ----------  ----------  ----------  ----------
H318/3   alpha1         ----------  ----------  ----------  ----------  ----------
Rat      alpha1         ----------  ----------  ----------  ----------  ----------
         Consensus      GVFVLCWFPF  FFVLPLGSLF  PQLKPSEGVF  KVIFWLGYFN 401                                                              440
human    alpha1         ----------  ----------  ----------  ----.rp-wrv
H318/3   alpha1         ----------  ----------  ----------  ----.rp-wrv
Rat      alpha1         ----------  ----------  ----------  ---lws-rpp
         Consensus      SCVNPLIYPC  SSREFKRAFL  RLLRCQCRRR  RRR---L---

441                                                              480
human    alpha1         yg..hhw---  ...stsgl-q  dca----gdap  --ap-alt-l
H318/3   alpha1         yg..hhw---  ...stsgl-q  dca----gdap  --ap-alt-l
Rat      alpha1         lasldrr--f  rlrpqpsh-s  prg---phct  --cg-grh-.
         Consensus      ------RA-   ------R-   ---PSS----  PG--L---A-
```

FIG. 4D

```
                481
human  alpha1a  pdpdpeppgt pem-apv--r  -k..ppsafr ewrllgpfr-
H318/3 alpha1a  pdpdpeppgt pem-apv--r  -shpapsasg gcwgrsgdp-
Rat    alpha1a  ......gdag fgl-qsk--l  l......lr  ewrllgplq-
       Consensus ---------  ---Q---AS- R--------  ---------R
                                                          520

521                                       560
human  alpha1a  -ttqlrakvs slshkiragg  -q-aeaac-q -seveavslg
H318/3 alpha1a  -scapkspac rtrsppgars  -q-qraps-q -wrlcp*...
Rat    alpha1a  -ttqlrakvs slshkirs.g  -r-aetac-l -seveavsln
       Consensus P--------  ---------  ----A----A R-----SL- 561                                       588
human  alpha1a  vphevaegat cqayeladys  nlretdi*
H318/3 alpha1a  .........  .........   ........
Rat    alpha1a  vpqdgaeavi cqayepgdys  nlretdi*
       Consensus VP---AE--- CQAYE--DYS NLRETDI*
```

FIG. 5A Alignment of the Human Alpha-1b, Hamster Alpha-1b, and Rat Alpha-1b Adrenergic Receptors.

|  | FIG. 5A |
|---|---|
|  | FIG. 5B |
|  | FIG. 5C |
|  | FIG. 5D |

```
                 1                                                          40
Rat     alpha1b  ----------- ----h----- ----------- -dd------- -----------
Hamster alpha1b  ----------- ----q----- ----------- -da------- -----------
Human   alpha1b  ----------- ----h----- ----------- -na------- -----------
Consensus        MNPDLDTGHN  TSAPA-WGEL K--NFTGPNQ  TSSNSTLPQL 41                                                         80
Rat     alpha1b  -v--------- ----------- ----------- ----------- -----------
Hamster alpha1b  -v--------- ----------- ----------- ----------- -----------
Human   alpha1b  -i--------- ----------- ----------- ----------- -----------
Consensus        D-TRAISVGL  VLGAFILFAI VGNILVILSV ACNRHLRTPT 81                                                        120
Rat     alpha1b  ------i---- ----------- ----------- ----t------ -----------
Hamster alpha1b  ------i---- ----------- ----------- ----t------ -----------
Human   alpha1b  ------m---- ----------- ----------- ----a------ -----------
Consensus        NYFIVNLA-A  DLLLSFTVLP FSA-LEVLGY WVLGRIFCDI 121                                                       160
Rat     alpha1b  ----------- ----------- ----------- ----------- -----------
Hamster alpha1b  ----------- ----------- ----------- ----------- -----------
Human   alpha1b  ----------- ----------- ----------- ----------- -----------
Consensus        WAAVDVLCCT  ASILSLCAIS IDRYIGVRYS LQYPTLVTRR
```

FIG. 5B

```
                   161                                                                        200
Rat      alpha1b   ---------- ---------- ---------- ---------- ---------- ----------
Hamster  alpha1b   ---------- ---------- ---------- ---------- ---------- ----------
Human    alpha1b   ---------- ---------- ---------- ---------- ---------- ----------
Consensus          KAILALLSVW VLSTVISIGP LLGWKEPAPN DDKECGVTEE 201                                                                        240
Rat      alpha1b   --c----c-- ---------- ---------- ---------- ---------- ----------
Hamster  alpha1b   --y----s-- ---------- ---------- ---------- ---------- ----------
Human    alpha1b   --y----s-- ---------- ---------- ---------- ---------- ----------
Consensus          PF-ALF-SLG SFYIPLAVIL VMYCRVYIVA KRTTKNLEAG 241                                                                        280
Rat      alpha1b   ---------- ---------- ---------- ---------- ---------- ----------
Hamster  alpha1b   ---------- ---------- ---------- ---------- ---------- ----------
Human    alpha1b   ---------- ---------- ---------- ---------- ---------- ----------
Consensus          VMKEMSNSKE LTLRIHSKNF HEDTLSSTKA KGHNPRSSIA 281                                                                        320
Rat      alpha1b   ---------- ---------- ---------- ---------- ---------- ----------
Hamster  alpha1b   ---------- ---------- ---------- ---------- ---------- ----------
Human    alpha1b   ---------- ---------- ---------- ---------- ---------- ----------
Consensus          VKLFKFSREK KAAKTLGIVV GMFILCWLPF FIALPLGSLF
```

FIG. 5C

```
                                                                          360
Rat     alpha1b    ----------  ----------  ----------  ----------  -------m-
Hamster alpha1b    ----------  ----------  ----------  ----------  -------m-
Human   alpha1b    ----------  ----------  ----------  ----------  -------v-
        Consensus  STLKPPDAVF  KVVFWLGYFN  SCLNPIIYPC  SSKEFKRAF-
321
                                                                          400
Rat     alpha1b    -------..-  ----gg----  ----a-----  ----------  ---------
Hamster alpha1b    -------..-  ----sg----  ----a-----  ----------  ---------
Human   alpha1b    ------rg--  ----gr----  ----g-----  ----------  ---------
        Consensus  RILGCQC--R  --RRRRRRRR  LG-CAYTYRP  WTRGGSLERS
361
                                                                          440
Rat     alpha1b    ----------  ---m--qk--  ----------  ----------  ---tq--v-
Hamster alpha1b    r---------  ---m--sq--  ----------  ----------  ---aq--l-
Human   alpha1b    ----------  ---l--sq--  ----------  ----------  ---ap--v-
        Consensus  QSRKDSLDDS  GSC-SG---RT LPSASPSPGY LGRG--PP-E
401
                                                                          480
Rat     alpha1b    ---f-----p  ----------  -------l--  ----------  -------g-
Hamster alpha1b    ---y-----s  ----------  -------l--  ----------  -------g-
Human   alpha1b    ---f-----ap -----pa---  -------h--  ----------  -------t-
        Consensus  LCA-PEWK--  GALLSL--PE  PPGRRGR-DS  GPLFTFKLL-
441
```

FIG. 5D

```
                481                                              520
Rat    alpha1b  d------eat  -----dttt  -l--------  -------g--h-
Hamster alpha1b e-------    ------egd  -----datt  -l--------  -------a--h-
Human  alpha1b  e-------    ------dgg  ------eaaa  -v--------  -------a--q-
Consensus       -PESPGT---  ASNGGC----  D-ANGQPGFK  SNMPL-PG-F 521
Rat    alpha1b  *
Hamster alpha1b *
Human  alpha1b  *
Consensus       *
```

FIG. 6A Alignment of the Human Alpha-1c and Bovine Alpha-1c Adrenergic Receptors.

| FIG. 6A |
|---------|
| FIG. 6B |
| FIG. 6C |

```
                        1                                                        40
Human   alpha1c    ---------- ---------- ----q--a-- ---------- ----------
Bovine  alpha1c    ---------- ---------- ----h--p-- ---------- ----------
        Consensus  MVFLSGNASD SSNCT-PP-P VNISKAILLG VILGGLILFG 41                                                       80
Human   alpha1c    ---------- ---------- ----v----- ---------- ----------
Bovine  alpha1c    ---------- ---------- ----i----- ---------- ----------
        Consensus  VLGNILVILS VACHRHLHSV THYYIVNLAV ADLLLTSTVL 81                                                      120
Human   alpha1c    ---------- ---------- ---------- ----i----- ----------
Bovine  alpha1c    ---------- ---------- ---------- ----v----- ----------
        Consensus  PFSAIFE-LG YWAFGRVFCN -WAAVDVLCC TASIMGLCII 121                                                      160
Human   alpha1c    ---------- ---------- ---------- ----r----- ----------
Bovine  alpha1c    ---------- ---------- ---------- ----k----- ----------
        Consensus  SIDRYIGVSY PLRYPTIVTQ -RGLMALLCV WALSLVISIG
```

FIG. 6B

```
                     161                                                      200
Human    alpha1c     ----------  ----------  ----------  ----------  ----l---a---
Bovine   alpha1c     ----------  ----------  ----------  ----------  ----v---t---
         Consensus   PLFGWRQPAP  EDETICQINE  EPGYVLFSAL  GSFY-PL-II 201                                                      240
Human    alpha1c     ----------  ----------  ----------  ----------  ----------
Bovine   alpha1c     ----------  ----------  ----------  ----------  ----------
         Consensus   LVMYCRVYVV  AKRESRGLKS  GLKTDKSDSE  QVTLRIHRKN 241                                                      280
Human    alpha1c     -pa----ma-  ---t------  ----------  ----------  ----------
Bovine   alpha1c     -qv----vt-  ---n------  ----------  ----------  ----------
         Consensus   A--GGSG--S  AK-KTHFSVR  LLKFSREKKA  AKTLGIVVGC 281                                                      320
Human    alpha1c     ----------  ----------  ----------  -k--------  -v--------
Bovine   alpha1c     ----------  ----------  ----------  -r--------  -a--------
         Consensus   FVLCWLPFFL  VMPIGSFFPD  F-PSETVFKI  -FWLGYLNSC
```

FIG. 6C

```
                      321                                                           360
Human    alpha1c      ------------  ------------  ------c-----  ------a-----
Bovine   alpha1c      ------------  ------------  ------------  ------t-----
Consensus             INPIIYPCSS    QEFKKAFQNV    LRIQCL-RKQ    SSKH-LGYTL 361                                                           400
Human    alpha1c      -p--qav-----  ---m--------  -r-----r----  ------f-----
Bovine   alpha1c      -a--hvl-----  ---l--------  -a-----k----  -------i----
Consensus             H-PS---EGQ    HKD-VRIPVG    S-ETFY-ISK    TDGVCEWK-F 401                                                           440
Human    alpha1c      --m------i    t-sk-q-s---   ------------  ------v-----
Bovine   alpha1c      --l------m    a-ar-p-a---   ------------  ------l-----
Consensus             SS-PRGSAR-    -V--D-S-CT    TARVRSKSFL    QVCCC-GPST 441                       467
Human    alpha1c      --ldk---v-    ---v--------  ------*
Bovine   alpha1c      --hge--i--    ---i--------  ------*
Consensus             PS---NHQ-P    TIK-HTISLS    ENGEEV*
```

DNA ENCODING HUMAN ALPHA 1 ADRENERGIC RECEPTORS AND USES THEREOF

This application is a continuation of U.S. Ser. No. 08/334,698, filed Nov. 4, 1994, now U.S. Pat. No. 5,556,753, issued Sep. 17, 1996, which is a continuation of U.S. Ser. No. 07/952,798, filed Sep. 25, 1992, now abandoned, the contents of which are incorporated by reference.

BACKGROUND OF THE INVENTION

Throughout this application various publications are referred to by partial citations within parenthesis. Full citations for these publications may be found at the end of the specification immediately preceding the claims. The disclosures of these publications, in their entireties, are hereby incorporated by reference into this application in order to more fully describe the state of the art to which this invention pertains.

Although adrenergic receptors (ARs) bind the same endogenous catecholamines (epinephrine and norepinephrine, NE) their physiological as well as pharmacological specificity is markedly diverse. This diversity is due primarily to the existence of at least nine different proteins encoding three distinct adrenergic receptors types ($\alpha_1$, $\alpha 2$, and $\beta$). These proteins belong to the super-family of G-protein coupled receptors, and are characterized by a single polypeptide chain which span the plasma membrane seven times, with an extracellular amino terminus, and a cytoplasmic carboxyl terminus. The molecular cloning of three genes encoding $\alpha_1$-ARs supports the existence of pharmacologically and anatomically distinct $\alpha_1$-receptor subtypes. The $\alpha_{1b}$-receptor was originally cloned from a hamster smooth muscle cell line cDNA library, and encodes a 515 a.a. peptide that shows 42–47% homology with other ARs. The message for the $\alpha_{1b}$-receptor is abundant in rat liver, heart, cerebral cortex and kidney, and its gene was localized to human chromosome 5 (4). A second cDNA clone from a bovine brain library was found which encoded a 466-residue polypeptide with 72% homology to the $\alpha_{1b}$-AR gene. It was further distinguished from $\alpha_{1b}$ by the finding that its expression was restricted to human hippocampus, and by its localization to human chromosome 8 and it has been designated as the $\alpha_{1c}$-AR (20). The cloning of an $\alpha_{1a}$-AR has been reported recently. This gene, isolated from a rat brain cDNA library, encodes a 560-residue polypeptide that shows 73% homology with the hamster $\alpha_{1b}$-receptor. The message for this subtype is abundant in rat vas deferens, aorta, cerebral cortex and hippocampus, and its gene has been localized to human chromosome 5 (12).

Pharmacological studies have demonstrated the existence of two $\alpha_1$-adrenergic receptor subtypes. The studies of $\alpha_1$-AR-mediated responses in vascular tissue suggested the possible existence of receptor subtypes, based on the potency and efficacy of adrenergic agonists, as well as differential sensitivity of $\alpha_1$ receptor-mediated responses to extracellular calcium and calcium channel blockers (6, 24). Although radioligand binding studies of brain $\alpha_1$-ARs with either [$^3$H]WB4101 and [$^3$H]prazosin showed good agreement with the potency of $\alpha$-adrenergic antagonists on vascular responses (23,10), subsequent binding studies of rat brain $\alpha_1$-ARs provided strong evidence for the existence of receptor heterogeneity, based on the relative affinities for prazosin and WB4101 (15). These observations were supported by the finding that chloroethylclonidine (CEC) inactivated 50% of the $\alpha_1$ sites from rat cerebral cortex and 80% of the binding sites from liver or spleen ($\alpha_{1b}$), but did not inactivate $\alpha_1$-receptors from the hippocampus or vas deferens ($\alpha_{1a}$) (14). Taken together, these results suggested a classification of the $\alpha_{1a}$-subtype as high affinity for WB4101 and insensitive to alkylation by CEC, and $\alpha_{1b}$-subtype as 10 to 20 fold lower affinity for WB4101, but sensitive to inactivation by CEC. Consistent with this evidence the transfection of the hamster $\alpha_{1b}$ gene into COS-7 cells induced the expression of an $\alpha$1-receptor with high affinity for WB4101, 95% of which could be inactivated by CEC. Conversely, upon expression of the rat $\alpha_{1a}$ receptor gene in COS-7 cells, it showed a 10-fold higher affinity for WB4101 than the $\alpha_{1b}$-receptor, and the binding site was resistant to inactivation by CEC. The existence of the $\alpha_{1c}$ receptor was not predicted from pharmacological data and upon expression it showed 16 and 30 fold higher affinity for WB4101 and phentolamine respectively, than the $\alpha_{1b}$-receptor and was partially inactivated (65%) by CEC.

Molecular cloning and pharmacological studies have demonstrated the existence of at least three $\alpha_1$-adrenergic receptor subtypes. However, it is not clear whether the pharmacological properties of these three cognates might be due also to species differences. This caveat is particularly relevant in the case of the bovine $\alpha_{1c}$ receptor, due to its restricted species and tissue expression. The cloning and expression of the human $\alpha_1$ adrenergic receptors will allow the further characterization of the pharmacology of the individual human $\alpha_1$ receptor subtypes.

SUMMARY OF THE INVENTION

This invention provides and isolated nucleic acid molecule encoding a human $\alpha_1$ adrenergic receptor. This invention further provides an isolated nucleic acid molecule encoding a human $\alpha_{1a}$ receptor. In one embodiment of this invention, the nucleic acid molecule comprises a plasmid pcEXV-$\alpha_{1a}$. This invention also provides an isolated nucleic acid molecule encoding a human $\alpha_{1b}$ receptor. In one embodiment of this invention, the nucleic acid molecule comprises a plasmid pcEXV-$\alpha_{1b}$. This invention further provides an isolated nucleic acid molecule encoding a human $\alpha_{1c}$ receptor. In one embodiment of this invention, the nucleic acid molecule comprises a plasmid pcEXV-$\alpha_{1c}$.

This invention also provides vectors such as plasmids comprising a DNA molecule encoding a human $\alpha_{1a}$ receptor, adapted for expression in a bacterial, a yeast cell, or a mammalian cell which additionally comprise regulatory elements necessary for expression of the DNA in the bacteria, yeast or mammalian cells so located relative to the DNA encoding the human $\alpha_{1a}$ receptor as to permit expression thereof. This invention also provides vectors such as plasmids comprising a DNA molecule encoding a human $\alpha_{1b}$ receptor, adapted for expression in a bacterial, a yeast cell, or a mammalian cell which additionally comprise regulatory elements necessary for expression of the DNA in the bacteria, yeast or mammalian cells so located relative to the DNA encoding the human receptor as to permit expression thereof. This invention also provides vectors such as plasmids comprising a DNA molecule encoding a human $\alpha_{1c}$ receptor, adapted for expression in a bacterial, a yeast cell, or a mammalian cell which additionally comprise regulatory elements necessary for expression of the DNA in the bacteria, yeast or mammalian cells so located relative to the DNA encoding the human $\alpha_{1c}$ receptor as to permit expression thereof.

This invention provides a mammalian cell comprising a DNA molecule encoding a human $\alpha_{1a}$ receptor. This invention also provides a mammalian cell comprising a DNA molecule encoding a human $\alpha_{1b}$ receptor. This invention also provides a mammalian cell comprising a DNA molecule encoding a human $\alpha_{1c}$ receptor.

This invention provides a nucleic acid probe comprising a nucleic acid molecule of at least 15 nucleotides capable of specifically hybridizing with a sequence included within the sequence of a nucleic acid molecule encoding a human $\alpha_{1a}$ receptor. This invention provides a nucleic acid probe comprising a nucleic acid molecule of at least 15 nucleotides capable of specifically hybridizing with a sequence included within the sequence of a nucleic acid molecule encoding a human $\alpha_{1b}$ receptor. This invention provides a nucleic acid probe comprising a nucleic acid molecule of at least 15 nucleotides capable of specifically hybridizing with a sequence included within the sequence of a nucleic acid molecule encoding a human $\alpha_{1c}$ receptor.

This invention provides an antisense oligonucleotide having a sequence capable of specifically binding to any sequences of an mRNA molecule encoding a human receptor so as to prevent translation of the mRNA molecule. This invention provides an antisense oligonucleotide having a sequence capable of specifically binding to any sequences of an mRNA molecule encoding a human $\alpha_{1b}$ receptor so as to prevent translation of the mRNA molecule. This invention provides an antisense oligonucleotide having a sequence capable of specifically binding to any sequences of an mRNA molecule encoding a human $\alpha_{1c}$ receptor so as to prevent translation of the mRNA molecule.

This invention provides method for detecting expression of a specific human $\alpha_1$ adrenergic receptor, which comprises obtaining RNA from cells or tissue, contacting the RNA so obtained with a nucleic acid probe comprising a nucleic acid molecule of at least 15 nucleotides capable of specifically hybridizing with a sequence included within the sequence of a nucleic acid molecule encoding a human $\alpha_1$ receptor under hybridizing conditions, detecting the presence of any mRNA hybridized to the probe, the presence of mRNA hybridized to the probe indicating expression of the specific human $\alpha_1$ adrenergic receptor, and thereby detecting the expression of the specific human $\alpha_1$ adrenergic receptor.

This invention provides a method for detecting the expression of a specific human α1 adrenergic receptor in a cell or tissue by in situ hybridization which comprises, contacting the cell or tissue with a nucleic acid probe comprising a nucleic acid molecule of at least 15 nucleotides capable of specifically hybridizing with a sequence included within the sequence of a nucleic acid molecule encoding a human $\alpha_1$ receptor under hybridizing conditions, detecting the presence of any mRNA hybridized to the probe, the presence of mRNA hybridized to the probe indicating expression of the specific human $\alpha_1$ adrenergic receptor, and thereby detecting the expression of the specific human $\alpha_1$ adrenergic receptor.

This invention provides a method for isolating a nucleic acid molecule encoding a receptor by nucleic acid sequence homology using a nucleic acid probe, the sequence of which is derived from the nucleic acid sequence encoding a human $\alpha_1$ adrenergic receptor.

This invention provides a method for isolating a nucleic acid molecule encoding a human $\alpha_1$ adrenergic receptor which comprises the use of the polymerase chain reaction and oligonucleotide primers, the sequence of which are derived from the nucleic acid sequence encoding a human α1 adrenergic receptor.

This invention provides a method for isolating a human $\alpha_{1a}$ adrenergic receptor protein which comprises inducing cells to express the human $\alpha_1$ adrenergic receptor protein, recovering the human $\alpha_1$ adrenergic receptor from the resulting cells, and purifying the human $\alpha_1$ adrenergic receptor so recovered.

This invention provides an antibody to the human $\alpha_{1a}$ adrenergic receptor. This invention also provides an antibody to the human $\alpha_{1b}$ adrenergic receptor. This invention also provides an antibody to the human $\alpha_{1c}$ adrenergic receptor.

A pharmaceutical composition comprising an amount of a substance effective to alleviate the abnormalities resulting from overexpression of a human $\alpha_{1a}$ adrenergic receptor and a pharmaceutically acceptable carrier is provided by this invention. A pharmaceutical composition comprising an amount of a substance effective to alleviate the abnormalities resulting from overexpression of a human $\alpha_{1b}$ adrenergic receptor and a pharmaceutically acceptable carrier is provided by this invention. A pharmaceutical composition comprising an amount of a substance effective to alleviate the abnormalities resulting from overexpression of a human $\alpha_{1c}$ adrenergic receptor and a pharmaceutically acceptable carrier is provided by this invention.

A pharmaceutical composition comprising an amount of a substance effective to alleviate abnormalities resulting from underexpression of a human $\alpha_{1a}$ adrenergic receptor and a pharmaceutically acceptable carrier is provided by this invention. A pharmaceutical composition comprising an amount of a substance effective to alleviate abnormalities resulting from underexpression of a human $\alpha_{1b}$ adrenergic receptor and a pharmaceutically acceptable carrier is provided by this invention. A pharmaceutical composition comprising an amount of a substance effective to alleviate abnormalities resulting from underexpression of a human $\alpha_{1c}$ adrenergic receptor and a pharmaceutically acceptable carrier is provided by this invention.

This invention provides a transgenic non-human mammal whose genome comprises a nucleic acid molecule encoding a human α1 adrenergic receptor, the DNA molecule so placed as to be transcribed into antisense mRNA complementary to mRNA encoding a human $\alpha_1$ adrenergic receptor and which hybridizes to mRNA encoding a human $\alpha_1$ adrenergic receptor thereby reducing its translation.

This invention provides a method for determining the physiological effects of varying the levels of expression of a specific human α1 adrenergic receptor which comprises producing a transgenic non-human mammal whose levels of expression of a human $\alpha_1$ adrenergic receptor can be varied by use of an inducible promoter.

This invention provides method for determining the physiological effects of expressing varying levels of a specific human $\alpha_1$ adrenergic receptor which comprises producing a panel of transgenic non-human mammals each expressing a different amount of the human $\alpha_1$ adrenergic receptor.

This invention provides a method for determining whether a ligand not known to be capable of specifically binding to a human $\alpha_1$ adrenergic receptor can bind to a human $\alpha_1$ adrenergic receptor, which comprises contacting a mammalian cell comprising a plasmid adapted for expression in a mammalian cell which further comprises a DNA molecule which expresses a human $\alpha_1$ adrenergic receptor on the cell surface with the ligand under conditions permitting binding of ligands known to bind to a human $\alpha_1$ adrenergic receptor, detecting the presence of any ligand bound to the human $\alpha_1$ adrenergic receptor, the presence of bound ligand thereby determining the ligand binds to the human $\alpha_1$ adrenergic receptor.

This invention provides a method for screening drugs to identify drugs which interact with, and specifically bind to, a human $\alpha_1$ adrenergic receptor on the surface of a cell, which comprises contacting a mammalian cell which comprises a plasmid adapted for expression in a mammalian cell which further comprises a DNA molecule which expresses a human $\alpha_1$ adrenergic receptor on the cell surface with a plurality of drugs, determining those drugs which bind to the human $\alpha_1$ adrenergic receptor expressed on the cell surface of the mammalian cell, and thereby identifying drugs which interact with, and bind to, the human $\alpha_1$ adrenergic receptor.

This invention provides a method for identifying a ligand which binds to and activates or blocks the activation of, a human $\alpha_1$ adrenergic receptor expressed on the surface of a cell, which comprises contacting a mammalian cell which comprises a plasmid adapted for expression in a mammalian cell which further comprises a DNA molecule which expresses a human $\alpha_1$ adrenergic receptor on the cell surface with the ligand, determining whether the ligand binds to and activates or blocks the activation of the receptor using a bioassay such as a second messenger assays.

This invention also provides a method for identifying a ligand which is capable of binding to and activating or inhibiting a human $\alpha_1$ adrenergic receptor, which comprises contacting a mammalian cell, wherein the membrane lipids have been labelled by prior incubation with a labelled lipid precursor molecule, the mammalian cell comprising a plasmid adapted for expression in a mammalian cell which further comprises a DNA molecule which expresses a human $\alpha_1$ adrenergic receptor with the ligand and identifying an inositol phosphate metabolite released from the membrane lipid as a result of ligand binding to and activating an $\alpha_1$ adrenergic receptor.

This invention also provides a method for identifying a ligand that is capable of binding to and activating or inhibiting a human $\alpha_1$ adrenergic receptor, wherein the binding of ligand to the adrenergic receptor results in a physiological response, which comprises contacting a mammalian cell which comprises a plasmid adapted for expression in a mammalian cell which further comprises a DNA molecule which expresses a human $\alpha_1$ adrenergic receptor with a calcium sensitive fluorescent indicator, removing the indicator that has not been taken up by the cell, contacting the cells with the ligand and identifying an increase or decrease in intracellular $Ca^{+2}$ as a result of ligand binding to and activating or inhibiting $\alpha_1$ adrenergic receptor activity.

This invention provides a method for detecting the presence of a human $\alpha_{1a}$ adrenergic receptor on the surface of a cell, which comprises contacting the cell with an antibody to human $\alpha_{1a}$ adrenergic receptor under conditions which permit binding of the antibody to the receptor, detecting the presence of any of the antibody bound to the human $\alpha$1a adrenergic receptor and thereby the presence of a human $\alpha_{1a}$ adrenergic receptor on the surface of the cell.

This invention provides a method for detecting the presence of a human $\alpha_{1b}$ adrenergic receptor on the surface of a cell, which comprises contacting the cell with an antibody to human $\alpha_{1b}$ adrenergic receptor under conditions which permit binding of the antibody to the receptor, detecting the presence of any of the antibody bound to the human $\alpha_{1b}$ adrenergic receptor and thereby the presence of a human $\alpha_{1b}$ adrenergic receptor on the surface of the cell.

This invention provides a method for detecting the presence of a human $\alpha_{1c}$ adrenergic receptor on the surface of a cell, which comprises contacting the cell with an antibody to human $\alpha_{1c}$ adrenergic receptor under conditions which permit binding of the antibody to the receptor, detecting the presence of any of the antibody bound to the human $\alpha_{1c}$ adrenergic receptor and thereby the presence of a human $\alpha_{1c}$ adrenergic receptor on the surface of the cell.

This invention provides a method of treating an abnormal condition related to an excess of activity of a human $\alpha_1$ adrenergic receptor subtype, which comprises administering an amount of a pharmaceutical composition effective to reduce $\alpha_1$ adrenergic activity as a result of naturally occurring substrate binding to and activating a specific $\alpha_1$ adrenergic receptor.

This invention provides a method for treating abnormalities which are alleviated by an increase in the activity of a specific human $\alpha_1$ adrenergic receptor, which comprises administering a patient an amount of a pharmaceutical composition effective to increase the activity of the specific human $\alpha_1$ adrenergic receptor thereby alleviating abnormalities resulting from abnormally low receptor activity.

This invention provides a method for diagnosing a disorder or a predisposition to a disorder associated with the expression of a specific human $\alpha_1$ adrenergic receptor allele which comprises: a.) obtaining DNA from subjects suffering from a disorder; b.) performing a restriction digest of the DNA with a panel of restriction enzymes; c.) electrophoretically separating the resulting DNA fragments on a sizing gel; d.) contacting the gel with a nucleic acid probe labelled with a detectable marker and which hybridizes to the nucleic acid encoding a specific human $\alpha_1$ adrenergic receptor; e.) detecting the labelled bands which have hybridized to the DNA encoding the specific $\alpha_1$ adrenergic receptor labelled with the detectable marker to create a unique band pattern specific to the DNA of subjects suffering with the disorder; f.) preparing DNA for diagnosis by steps a–e; g.) comparing the unique band pattern specific to the DNA of patients suffering from the disorder from step e and DNA obtained for diagnosis from step f to determine whether the patterns are the same or different and to diagnose thereby predisposition to the disorder if the patterns are the same.

This invention provides a method for identifying a substance capable of alleviating the abnormalities resulting from overexpression of a specific human $\alpha_1$ adrenergic receptor which comprises administering a substance to the transgenic non-human mammal comprising the DNA encoding a specific $\alpha_1$ adrenergic receptor and determining whether the substance alleviates the physical and behavioral abnormalities displayed by the transgenic nonhuman mammal as a result of overexpression of the human $\alpha_1$ adrenergic receptor subtype.

This invention provides a method for identifying a substance capable of alleviating the abnormalities resulting from underexpression of a human $\alpha_1$ adrenergic receptor subtype, which comprises administering a substance to a non-human transgenic mammal which is expressing a human $\alpha_1$ adrenergic receptor incapable of receptor activity or is underexpressing the human $\alpha_1$ adrenergic receptor subtype, and determining whether the substance alleviates the physical and behavioral abnormalities displayed by the transgenic nonhuman mammal as a result of underexpression of a human $\alpha_1$ adrenergic receptor subtype.

This invention provides a method of treating abnormalities in a subject, wherein the abnormality is alleviated by the reduced expression of a human $\alpha_1$ adrenergic receptor subtype which comprises administering to a subject an effective amount of the pharmaceutical composition effective to reduce expression of a specific $\alpha_1$ adrenergic receptor subtype.

This invention provides a method of treating abnormalities resulting from underexpression of a human $\alpha_1$ adrenergic receptor which comprises administering to a subject an amount of a pharmaceutical composition effective to alleviate abnormalities resulting from underexpression of the specific human $\alpha_1$ adrenergic receptor.

BRIEF DESCRIPTION OF THE FIGURES

FIGS. 1A–1I. Nucleotide Sequence and Deduced Amino Acid Sequence of Novel Human Alpha-1a Adrenergic Receptor.

Nucleotides are presented in the 5' to 3' orientation and the coding region is numbered starting from the initiating methionine and ending in the termination codon. Deduced amino acid sequence by translation of a long open reading frame is shown, along with the 5' and 3' untranslated regions. Numbers in the left and right margins represent nucleotide (top line) and amino acid (bottom line) numberings, starting with the first position as the adenosine (A) and the initiating methionine (M), respectively.

FIGS. 2A–2H. Nucleotide Sequence and Deduced Amino Acid Sequence of Novel Human Alpha-1b Adrenergic Receptor.

Nucleotides are presented in the 5' to 3' orientation and the coding region is numbered starting from the initiating methionine and ending in the termination codon. Deduced amino acid sequence by translation of a long open reading frame is shown, along with the 5' and 3' untranslated regions. Numbers in the left and right margins represent nucleotide (top line) and amino acid (bottom line) numberings, starting with the first position as the adenosine (A) and the initiating methionine (M), respectively.

FIGS. 3A–3G. Nucleotide Sequence and Deduced Amino Acid Sequence of Novel Human Alpha-1c Adrenergic Receptor.

Nucleotides are presented in the 5' to 3' orientation and the coding region is numbered starting from the initiating methionine and ending in the termination codon. Deduced amino acid sequence by translation of a long open reading frame is shown, along with the 5' and 3' untranslated regions. Numbers in the left and right margins represent nucleotide (top line) and amino acid (bottom line) numberings, starting with the first position as the adenosine (A) and the initiating methionine (M), respectively.

FIGS. 4A–4D. Alignment of the Human Alpha-1a, H318/3 Alpha-1a, and Rat Alpha-1a Adrenergic Receptors.

The deduced amino acid sequence of the human $\alpha_{1a}$ receptor (first line), from the starting methionine (M) to the stop codon (*), is aligned with the previously published human "$\alpha_{1a}$" adrenergic receptor clone, H318/3 (2) (second line) and with the rat alpha-1a (12) (third line). Also shown is a consensus amino acid sequence (fourth line), containing a hyphen at a particular position, when all receptors have the same amino acid or an amino acid at this position, when there is disparity in the three receptors. Dots indicate spaces corresponding to no amino acid at this position. Note that the human and rat $\alpha_{1a}$ receptors have greater homology in the amino (positions 1–90) and carboxyl (positions 440–598) termini than do the previously published "$\alpha_{1a}$" (H318/3) and rat $\alpha_{1a}$ receptors (see text). Dots indicate spaces corresponding to no amino acid at this position. Numbers above amino acid sequences correspond to amino acid positions, starting with the initiating methionine (M) and ending with the termination codon (*).

FIGS. 5A–5D. Alignment of the Human Alpha-1b, Hamster Alpha-1b, and Rat Alpha-1b Adrenergic Receptors.

The deduced amino acid sequence of the human $\alpha_{1b}$ receptor (third line), from the starting methionine (M) to the stop codon (*), is aligned with the previously published rat $\alpha_{1b}$ adrenergic receptor clone (25) (first line) and with the hamster alpha-1b (4) (second line). Also shown is a consensus amino acid sequence (fourth line), containing a hyphen at a particular position, when all receptors have the same amino acid or an amino acid at this position, when there is disparity in the three receptors. Dots indicate spaces corresponding to no amino acid at this position. Numbers above amino acid sequences correspond to amino acid position, starting with the initiating methionine (M) and ending with the termination codon (*).

FIGS. 6A–6C. Alignment of the Human Alpha-1c and Bovine Alpha-1c Adrenergic Receptors.

The deduced amino acid sequence of the human sic receptor (first line), from the starting methionine (M) to the stop codon (*), is aligned with the previously published bovine $\alpha_{1b}$ adrenergic receptor clone (13)(first line). Also shown is a consensus amino acid sequence (third line), containing a hyphen at a particular position, when all receptors have the same amino acid or an amino acid at this position, when there is disparity in the three receptors. Dots indicate spaces corresponding to no amino acid at this position. Numbers above amino acid sequences correspond to amino acid position, starting with the initiating methionine (M) and ending with the termination codon (*).

DETAILED DESCRIPTION OF THE INVENTION

This invention provides an isolated nucleic acid molecule encoding a human $\alpha_1$ adrenergic receptor. This invention also provides an isolated nucleic acid molecule encoding a human $\alpha_{1a}$ adrenergic receptor. This invention also provides an isolated nucleic acid molecule encoding a human $\alpha_{1b}$ adrenergic receptor. This invention also provides an isolated nucleic acid molecule encoding a human $\alpha_{1c}$ adrenergic receptor. As used herein, the term "isolated nucleic acid molecule" means a non-naturally occurring nucleic acid molecule that is, a molecule in a form which does not occur in nature. Examples of such an isolated nucleic acid molecule are an RNA, cDNA, or an isolated genomic DNA molecule encoding a human $\alpha_{1a}$, human $\alpha_{1b}$ or human $\alpha_{1c}$ adrenergic receptor. As used herein, the term "$\alpha_{1a}$ receptor", "$\alpha_{1b}$ receptor", or "$\alpha_{1c}$ receptor" means a molecule which is a distinct member of a class of $\alpha_1$ adrenergic receptor molecules which under physiologic conditions, is substantially specific for the the catecholamines epinephrine and norepinephrine, is saturable, and having high affinity for the catecholamines epinephrine and norepinephrine. The term "$\alpha_1$ adrenergic receptor subtype" refers to a distinct member of the class of human $\alpha_1$ adrenergic receptors, which may be any one of the human $\alpha_{1a}$, $\alpha_{1b}$ or $\alpha_{1c}$ adrenergic receptors. The term "specific $\alpha_1$ adrenergic receptor" refers to a distinct member of the group or class of human $\alpha_1$ adrenergic receptors, which may be any one of the human $\alpha_{1a}$, $\alpha_{1b}$ or $\alpha_{1c}$ adrenergic receptors. One embodiment of this invention is an isolated human nucleic acid molecule encoding a human $\alpha_{1a}$ adrenergic receptor. Such a molecule may have coding sequences substantially the same as the coding sequence in FIGS. 1A–1I. The DNA molecule of FIGS. 1A–1I encodes the sequence of the human $\alpha_{1a}$ adrenergic receptor. Another, preferred embodiment is an isolated human nucleic acid molecule encoding a human $\alpha_{1b}$ adrenergic receptor. Such a molecule may have coding sequences substantially the same as the coding sequence in FIGS. 2A–2H. The DNA molecule of FIGS. 2A–2H encodes the sequence of the human $\alpha_{1b}$ adrenergic receptor. Another, preferred embodiment is an isolated human nucleic acid molecule encoding a human $\alpha_{1c}$ adrenergic receptor. Such a molecule may have coding sequences substantially the same as the coding sequence in FIGS. 3A–3G. The DNA molecule of FIGS. 3A–3G encodes the sequence of the human $\alpha_{1c}$ adrenergic receptor. One means of isolating a nucleic acid molecule encoding a $\alpha_1$ adrenergic receptor is to screen a genomic DNA or cDNA library with a natural or artificially designed DNA probe, using methods well known in the art. In the preferred embodiment of this invention, $\alpha_1$ adrenergic receptors include the human $\alpha_{1a}$, human $\alpha_{1b}$ and human $\alpha_{1c}$ adrenergic receptors and the nucleic acid molecules encoding them were isolated by screening a human genomic DNA library and by further screening screening of a human cDNA library to obtain the sequence of the entire human $\alpha_{1a}$, human $\alpha_{1b}$ or human $\alpha_{1c}$ adrenergic receptor. To obtain a single nucleic acid molecule encoding the entire human $\alpha_{1a}$, $\alpha_{1b}$ or $\alpha_{1c}$ adrenergic receptor two or more DNA clones encoding portions of the same receptor were digested with DNA restriction endonucleases and ligated together with DNA ligase in the proper orientation using techniques known to one of skill in the art. DNA or cDNA molecules which encode a human $\alpha_{1a}$, $\alpha_{1b}$ or $\alpha_{1c}$ adrenergic receptor are used to obtain complementary genomic DNA, cDNA or RNA from human, mammalian or other animal sources, or to isolate related cDNA or genomic DNA clones by the screening of cDNA or genomic DNA libraries, by methods described in more detail below. Transcriptional regulatory elements from the 5' untranslated region of the isolated clone, and other stability, processing, transcription, translation, and tissue specificity determining regions from the 3' and 5' untranslated regions of the isolated gene are thereby obtained.

This invention provides an isolated nucleic acid molecule which has been so mutated as to be incapable of encoding a molecule having normal human $\alpha_1$ adrenergic receptor activity, and not expressing native human $\alpha_1$ adrenergic receptor. An example of a mutated nucleic acid molecule provided by this invention is an isolated nucleic acid molecule which has an in-frame stop codon inserted into the coding sequence such that the transcribed RNA is not translated into protein.

This invention provides a cDNA molecule encoding a human $\alpha_{1a}$ adrenergic receptor, wherein the cDNA molecule has a coding sequence substantially the same as the coding sequence shown in FIGS. 1A–1I. This invention also provides a cDNA molecule encoding a human $\alpha_{1b}$ adrenergic receptor, wherein the cDNA molecule has a coding sequence substantially the same as the coding sequence shown in FIGS. 2A–2H. This invention also provides a cDNA molecule encoding a human $\alpha_{1c}$ adrenergic receptor, wherein the cDNA molecule has a coding sequence substantially the same as the coding sequence shown in FIGS. 3A–3G. These molecules and their equivalents were obtained by the means further described below.

This invention provides an isolated protein which is a human $\alpha_1$ adrenergic receptor. In one embodiment of this invention, the protein is a human $\alpha_{1a}$ adrenergic receptor having an amino acid sequence substantially similar to the amino acid sequence shown in FIGS. 1A–1H. In another embodiment of this invention, the protein is a human $\alpha_{1b}$ adrenergic receptor having an amino acid sequence substantially similar to the amino acid sequence shown in FIGS. 2A–2H. In another embodiment of this invention, the protein is a human $\alpha_{1c}$ adrenergic receptor having an amino acid sequence substantially similar to the amino acid sequence shown in FIGS. 3A–3G. As used herein, the term "isolated protein" is intended to encompass a protein molecule free of other cellular components. One means for obtaining an isolated human $\alpha_1$ adrenergic receptor is to express DNA encoding the $\alpha_1$ adrenergic receptor in a suitable host, such as a bacterial, yeast, or mammalian cell, using methods well known to those skilled in the art, and recovering the human $\alpha_1$ adrenergic receptor after it has been expressed in such a host, again using methods well known in the art. The human $\alpha_1$ adrenergic receptor may also be isolated from cells which express it, in particular from cells which have been transfected with the expression vectors described below in more detail.

This invention also provides a vector comprising an isolated nucleic acid molecule such as DNA, RNA, or cDNA, encoding a human $\alpha_{1a}$ receptor. This invention also provides a vector comprising an isolated nucleic acid molecule such as DNA, RNA, or cDNA, encoding a human human $\alpha_{1b}$ adrenergic receptor. This invention also provides a vector comprising an isolated nucleic acid molecule such as DNA, RNA, or cDNA, encoding a human human $\alpha_{1c}$ adrenergic receptor. Examples of vectors are viruses such as bacteriophages (such as phage lambda), cosmids, plasmids (such as pUC18, available from Pharmacia, Piscataway, N.J.), and other recombination vectors. Nucleic acid molecules are inserted into vector genomes by methods well known to those skilled in the art. Examples of such plasmids are plasmids comprising cDNA having a coding sequence substantially the same as: the coding sequence shown in FIGS. 1A–1I, 2A–2H, and FIGS. 3A–3G. Alternatively, to obtain these vectors, insert and vector DNA can both be exposed to a restriction enzyme to create complementary ends on both molecules which base pair with each other and are then ligated together with a ligase. Alternatively, linkers can be ligated to the insert DNA which correspond to a restriction site in the vector DNA, which is then digested with the restriction enzyme which cuts at that site. Other means are also available.

This invention also provides vectors comprising a DNA molecule encoding a human $\alpha_{1a}$, vectors comprising a DNA molecule encoding a human $\alpha_{1b}$ adrenergic receptor and vectors comprising a DNA molecule encoding a human adrenergic receptor adapted for expression in a bacterial cell, a yeast cell, or a mammalian cell which additionally comprise the regulatory elements necessary for expression of the DNA in the bacterial, yeast, or mammalian cells so located relative to the DNA encoding a human $\alpha_1$ adrenergic receptor as to permit expression thereof. DNA having coding sequences substantially the same as the coding sequence shown in FIGS. 1A–1I may be inserted into the vectors to express a human $\alpha_{1a}$ adrenergic receptor. DNA having coding sequences substantially the same as the coding sequence shown in FIGS. 2A–2H may be inserted into the vectors to express a human $\alpha_{1b}$ adrenergic receptor. DNA having coding sequences substantially the same as the coding sequence shown in FIGS. 3A–3G may usefully be inserted into the vectors to express a human $\alpha_{1c}$ adrenergic receptor. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Maniatis, et al., Molecular Cloning, Cold Spring Harbor Laboratory, 1982). Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general. Expression vectors are useful to produce cells that express a human $\alpha_1$ adrenergic receptor. Certain uses for such cells are described in more detail below.

In one embodiment of this invention a plasmid is adapted for expression in a bacterial, yeast, or, in particular, a mammalian cell wherein the plasmid comprises a DNA molecule encoding a human $\alpha_{1a}$ adrenergic receptor, a DNA molecule encoding a human $\alpha_{1b}$ adrenergic receptor or a DNA molecule encoding a human $\alpha_{1c}$ adrenergic receptor and the regulatory elements necessary for expression of the DNA in the bacterial, yeast, or mammalian cell so located relative to the DNA encoding a human $\alpha_1$ adrenergic receptor as to permit expression thereof. Suitable plasmids may include, but are not limited to plasmids adapted for expression in a mammalian cell, e.g., pCEXV-3 derived expression vector. Examples of such plasmids adapted for expression in a mammalian cell are plasmids comprising cDNA having coding sequences substantially the same as the coding sequence shown in FIGS. 1A–1I, 2A–2H, and 3A–3G and the regulatory elements necessary for expression of the DNA in the mammalian cell. These plasmids have been designated pcEXV-$\alpha_{1a}$ deposited under ATCC Accession No. 75319, on Sep. 25, 1992, pcEXV-$\alpha_{1b}$ deposited under ATCC Accession No. 75318, on Sep. 25, 1992, and pcEXV-$\alpha_{1c}$ deposited under ATCC Accession No. 75317, on Sep. 25, 1992, respectively. Those skilled in the art will readily appreciate that numerous plasmids adapted for expression in a mammalian cell which comprise DNA encoding human $\alpha_1$ adrenergic receptors and the regulatory elements necessary to express such DNA in the mammalian cell may be constructed utilizing existing plasmids and adapted as appropriate to contain the regulatory elements necessary to express the DNA in the mammalian cell. The plasmids may be constructed by the methods described above for expression vectors and vectors in general, and by other methods well known in the art.

The deposits discussed supra were made pursuant to, and in satisfaction of, the provisions of the Budapest Treaty on the International Recognition of the Deposit of Microorganisms for the Purpose of Patent Procedure with the American Type Culture Collection (ATCC), 12301 Parklawn Drive, Rockville, Md. 20852.

This invention provides a mammalian cell comprising a DNA molecule encoding a human $\alpha_1$ adrenergic receptor, such as a mammalian cell comprising a plasmid adapted for expression in a mammalian cell, which comprises a DNA molecule encoding a human $\alpha_1$ adrenergic receptor and the regulatory elements necessary for expression of the DNA in the mammalian cell so located relative to the DNA encoding a human $\alpha_1$ adrenergic receptor as to permit expression thereof. Numerous mammalian cells may be used as hosts, including, but not limited to, the mouse fibroblast cell NIH3T3, CHO cells, HeLa cells, Ltk⁻ cells, human embryonic kidney cells, Cos cells, etc.

Expression plasmids such as that described supra may be used to transfect mammalian cells by methods well known in the art such as calcium phosphate precipitation, or DNA encoding these human $\alpha_1$ adrenergic receptors may be otherwise introduced into mammalian cells, e.g., by microinjection, to obtain mammalian cells which comprise DNA, e.g., cDNA or a plasmid, encoding a human $\alpha_1$ adrenergic receptor.

This invention provides a nucleic acid probe comprising a nucleic acid molecule of at least 15 nucleotides capable of specifically hybridizing with a sequence included within the sequence of a nucleic acid molecule encoding a human $\alpha_{1a}$ adrenergic receptor, for example with a coding sequence included within the sequence shown in FIGS. 1A–1I. This invention also provides a nucleic acid probe comprising a nucleic acid molecule of at least 15 nucleotides capable of specifically hybridizing with a sequence included within the sequence of a nucleic acid molecule encoding a human $\alpha_{1b}$ adrenergic receptor, for example with a coding sequence included within the sequence shown in FIGS. 2A–2H. This invention also provides a nucleic acid probe comprising a nucleic acid molecule of at least 15 nucleotides capable of specifically hybridizing with a sequence included within the sequence of a nucleic acid molecule encoding a human $\alpha_{1c}$ adrenergic receptor, for example with a coding sequence included within the sequence shown in FIGS. 3A–3G. As used herein, the phrase "specifically hybridizing" means the ability of a nucleic acid molecule to recognize a nucleic acid sequence complementary to its own and to form double-helical segments through hydrogen bonding between complementary base pairs. Nucleic acid probe technology is well known to those skilled in the art who will readily appreciate that such probes may vary greatly in length and may be labeled with a detectable label, such as a radioisotope or fluorescent dye, to facilitate detection of the probe. Detection of nucleic acid encoding a human $\alpha_1$ adrenergic receptor is useful as a diagnostic test for any disease process in which levels of expression of the corresponding human $\alpha_{1a}$, $\alpha_{1b}$ or $\alpha_{1c}$ adrenergic receptor are altered. DNA probe molecules are produced by insertion of a DNA molecule which encodes a human $\alpha_{1a}$, human $\alpha_{1b}$, or human $\alpha_{1c}$ adrenergic receptor or fragments thereof into suitable vectors, such as plasmids or bacteriophages, followed by insertion into suitable bacterial host cells and replication and harvesting of the DNA probes, all using methods well known in the art. For example, the DNA may be extracted from a cell lysate using phenol and ethanol, digested with restriction enzymes corresponding to the insertion sites of the DNA into the vector (discussed above), electrophoresed, and cut out of the resulting gel. Examples of such DNA molecules are shown in FIGS. 1A–1I, 2A–2H, and 3A–3G. The probes are useful for 'in situ' hybridization or in order to identify tissues which express this gene family, or for other hybridization assays for the presence of these genes or their mRNA in various biological tissues. In addition, synthesized oligonucleotides (produced by a DNA synthesizer) complementary to the sequence of a DNA molecule which encodes a human $\alpha_{1a}$ adrenergic receptor, or complementary to the sequence of a DNA molecule which encodes a human $\alpha_{1b}$ adrenergic receptor or complementary to the sequence of a DNA molecule which encodes a human $\alpha_{1c}$ adrenergic receptor are useful as probes for these genes, for their associated mRNA, or for the isolation of related genes by homology screening of genomic or cDNA libraries, or by the use of amplification techniques such as the Polymerase Chain Reaction.

This invention also provides a method for detecting expression of a human $\alpha_{1a}$ adrenergic receptor on the surface of a cell by detecting the presence of mRNA coding for a human $\alpha_{1a}$ adrenergic receptor. This invention also provides a method for detecting expression of a human $\alpha_{1b}$ adrenergic receptor on the surface of a cell by detecting the presence of mRNA coding for a human $\alpha_{1b}$ adrenergic receptor. This invention also provides a method for detecting expression of a human $\alpha_{1c}$ adrenergic receptor on the surface of a cell by detecting the presence of mRNA coding for a human $\alpha_{1c}$ adrenergic receptor. These methods comprise obtaining total mRNA from the cell using methods well known in the art and contacting the mRNA so obtained with a nucleic acid probe as described hereinabove, under hybridizing conditions, detecting the presence of mRNA hybridized to the probe, and thereby detecting the expression of the human $\alpha_1$ adrenergic receptor by the cell. Hybridization of probes to target nucleic acid molecules such as mRNA molecules employs techniques well known in the art. However, in one embodiment of this invention, nucleic acids are extracted by precipitation from lysed cells and the mRNA is isolated from the extract using a column which binds the poly-A tails of the mRNA molecules (Maniatis, T. et al., Molecular Cloning; Cold Spring Harbor Laboratory, pp. 197–98 (1982)). The mRNA is then exposed to radioactively labelled probe on a nitrocellulose membrane, and the probe hybridizes to and thereby labels complementary mRNA sequences. Binding may be detected by autoradiography or scintillation counting. However, other methods for performing these steps are well known to those skilled in the art, and the discussion above is merely an example.

This invention provides an antisense oligonucleotide having a sequence capable of specifically binding with any sequences of an mRNA molecule which encodes a human $\alpha_{1a}$ adrenergic receptor so as to prevent translation of the human $\alpha_{1a}$ adrenergic receptor. This invention also provides an antisense oligonucleotide having a sequence capable of specifically binding with any sequences of an mRNA molecule which encodes a human $\alpha_{1b}$ adrenergic receptor so as to prevent translation of the human $\alpha_{1b}$ adrenergic receptor. This invention also provides an antisense oligonucleotide having a sequence capable of binding specifically with any sequences of an mRNA molecule which encodes a human $\alpha_{1c}$ adrenergic receptor so as to prevent translation of the human $\alpha_{1c}$ adrenergic receptor. As used herein, the phrase "specifically binding" means the ability of an antisense oligonucleotide to recognize a nucleic acid sequence complementary to its own and to form double-helical segments through hydrogen bonding between complementary base pairs. The antisense oligonucleotide may have a sequence capable of specifically binding with any sequences of the cDNA molecules whose sequences are shown in FIGS. 1A–1I, 2A–2H or 3A–3G. A particular example of an antisense oligonucleotide is an antisense oligonucleotide comprising chemical analogues of nucleotides which are known to one of skill in the art.

This invention also provides a pharmaceutical composition comprising an effective amount of the oligonucleotide described above effective to reduce expression of a human $\alpha_{1a}$ adrenergic receptor, by passing through a cell membrane and specifically binding with mRNA encoding the human $\alpha_{1a}$ adrenergic receptor in the cell so as to prevent its translation and a pharmaceutically acceptable hydrophobic carrier capable of passing through a cell membrane. This invention also provides a pharmaceutical composition comprising an effective amount of the oligonucleotide described above effective to reduce expression of a human $\alpha_{1b}$ adrenergic receptor, by passing through a cell membrane and specifically binding with mRNA encoding the the human $\alpha_{1b}$ adrenergic receptor in the cell so as to prevent its translation and a pharmaceutically acceptable hydrophobic carrier capable of passing through a cell membrane. This invention further provides a pharmaceutical composition comprising an effective amount of the oligonucleotide described above effective to reduce expression of a human $\alpha_{1c}$ adrenergic receptor, by passing through a cell membrane and specifically binding with mRNA encoding the human adrenergic receptor in the cell so as to prevent its translation and a pharmaceutically acceptable hydrophobic carrier capable of passing through a cell membrane. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The oligonucleotide may be coupled to a substance which inactivates mRNA, such as a ribozyme. The pharmaceutically acceptable hydrophobic carrier capable of passing through cell membranes may also comprise a structure which binds to a transporter specific for a selected cell type and is thereby taken up by cells of the selected cell type. The structure may be part of a protein known to bind a cell-type specific transporter, for example an insulin molecule, which would target pancreatic cells. DNA molecules having coding sequences substantially the same as the coding sequence shown in FIGS. 1A–1I, 2A–2H, or 3A–3G may be used as the oligonucleotides of the pharmaceutical composition.

This invention also provides a method of treating abnormalities which are alleviated by reduction of expression of a human $\alpha_1$ adrenergic receptor. This method comprises administering to a subject an effective amount of the pharmaceutical composition described above effective to reduce expression of the human $\alpha 1$ adrenergic receptor by the subject. This invention further provides a method of treating an abnormal condition related to $\alpha 1$ adrenergic receptor activity which comprises administering to a subject an amount of the pharmaceutical composition described above effective to reduce expression of the human $\alpha 1$ adrenergic receptor by the subject. An example of such an abnormal condition is benign prostatic hypertrophy.

Antisense oligonucleotide drugs inhibit translation of mRNA encoding the human $\alpha 1a$, human $\alpha 1b$ or human $\alpha 1c$ adrenergic receptors. Synthetic antisense oligonucleotides, or other antisense chemical structures are designed to bind to mRNA encoding the human $\alpha 1a$ adrenergic receptor, to mRNA encoding the human $\alpha 1b$ adrenergic receptor or to mRNA encoding the human $\alpha 1c$ adrenergic receptor and inhibit translation of mRNA and are useful as drugs to inhibit expression of the human $\alpha_{1a}$ adrenergic receptor, the human $\alpha_{1b}$ adrenergic receptor or the human $\alpha_{1c}$ adrenergic receptor in patients. This invention provides a means to therapeutically alter levels of expression of the human $\alpha_{1a}$ adrenergic receptor, the human $\alpha_{1b}$ adrenergic receptor or the human $\alpha_{1c}$ adrenergic receptor by the use of a synthetic antisense oligonucleotide drug (SAOD) which inhibits translation of mRNA encoding these $\alpha_1$ adrenergic receptors. Synthetic antisense oligonucleotides, or other antisense chemical structures designed to recognize and selectively bind to mRNA, are constructed to be complementary to portions of the nucleotide sequences shown in FIGS. 1A–1I, 2A–2H, or 3A–3G of DNA, RNA or of chemically modified, artificial nucleic acids. The SAOD is designed to be stable in the blood stream for administration to patients by injection, or in laboratory cell culture conditions, for administration to cells removed from the patient. The SAOD is designed to be capable of passing through cell membranes in order to enter the cytoplasm of the cell by virtue of physical and chemical properties of the SAOD which render it capable of passing through cell membranes (e.g., by designing small, hydrophobic SAOD chemical structures) or by virtue of specific transport systems in the cell which recognize and transport the SAOD into the cell. In addition, the SAOD can be designed for administration only to certain selected cell populations by targeting the SAOD to be recognized by specific cellular uptake mechanisms which bind and take up the SAOD only within certain selected cell populations. For example, the SAOD may be designed to bind to a transporter found only in a certain cell type, as discussed above. The SAOD is also designed to recognize and selectively bind to the target mRNA sequence, which may correspond to a sequence contained within the sequences shown in FIGS. 1A–1I, 2A–2H, or 3A–3G by virtue of complementary base pairing to the mRNA. Finally, the SAOD is designed to inactivate the target mRNA sequence by any of three mechanisms: 1) by binding to the target mRNA and thus inducing degradation of the mRNA by intrinsic cellular mechanisms such as RNAse I digestion, 2) by inhibiting translation of the mRNA target by interfering with the binding of translation-regulating factors or of ribosomes, or 3) by inclusion of other chemical structures, such as ribozyme sequences or reactive chemical groups, which either degrade or chemically modify the target mRNA. Synthetic antisense oligonucleotide drugs have been shown to be capable of the properties described above when directed against mRNA targets (J. S. Cohen, Trends in Pharm. Sci. 10, 435 (1989); H. M. Weintraub, Sci. Am. January (1990) p. 40). In addition, coupling of ribozymes to antisense oligonucleotides is a promising strategy for inactivating target mRNA (N. Sarver et al., Science 247, 1222 (1990)). An SAOD serves as an effective therapeutic agent if it is designed to be administered to a patient by injection, or if the patient's target cells are removed, treated with the SAOD in the laboratory, and replaced in the patient. In this manner, an SAOD serves as a therapy to reduce human $\alpha_1$ adrenergic receptor expression in particular target cells of a patient, in any clinical condition which may benefit from reduced expression of a specific human $\alpha_1$ adrenergic receptor.

This invention provides an antibody directed to a human $\alpha_{1a}$ adrenergic receptor. This antibody may comprise, for example, a monoclonal antibody directed to an epitope of a human $\alpha_{1a}$ adrenergic receptor present on the surface of a cell, the epitope having an amino acid sequence substantially the same as an amino acid sequence for a cell surface epitope of the human $\alpha_{1a}$ adrenergic receptor included in the amino acid sequence shown in FIGS. 1A–1I. This invention also provides an antibody directed to a human $\alpha_{1b}$ adrenergic receptor. This antibody may comprise, for example, a monoclonal antibody directed to an epitope of a human $\alpha_{1b}$ adrenergic receptor present on the surface of a cell, the epitope having an amino acid sequence substantially the same as an amino acid sequence for a cell surface epitope of the human $\alpha_{1b}$ adrenergic receptor included in the amino acid sequence shown in FIGS. 2A–2H. This invention also provides an antibody directed to a human $\alpha_{1c}$ adrenergic receptor. This antibody may comprise, for example, a monoclonal antibody directed to an epitope of a human $\alpha_{1c}$ adrenergic receptor present on the surface of a cell, the epitope having an amino acid sequence substantially the same as an amino acid sequence for a cell surface epitope of the human $\alpha_{1c}$ adrenergic receptor included in the amino acid sequence shown in FIGS. 3A–3G. Amino acid sequences may be analyzed by methods well known to those skilled in the art to determine whether they produce hydrophobic or hydrophilic regions in the proteins which they build. In the case of cell membrane proteins, hydrophobic regions are well known to form the part of the protein that is inserted into the lipid bilayer which forms the cell membrane, while hydrophilic regions are located on the cell surface, in an aqueous environment. Therefore antibodies to the hydrophilic amino acid sequences shown in FIGS. 1A–1I will bind to a surface epitope of a the human $\alpha_{1a}$ adrenergic receptor, antibodies to the hydrophilic amino acid sequences shown in FIGS. 2A–2H will bind to a surface epitope of a human $\alpha_{1b}$ adrenergic receptor, and antibodies to the hydrophilic amino acid sequences shown in FIGS. 3A–3G will bind to a surface epitope of a human $\alpha_{1c}$ adrenergic receptor as described. Antibodies directed to human $\alpha_1$ adrenergic receptors may be serum-derived or monoclonal and are prepared using methods well known in the art. For example, monoclonal antibodies are prepared using hybridoma technology by fusing antibody producing B cells from immunized animals with myeloma cells and selecting the resulting hybridoma cell line producing the desired antibody. Cells such as NIH3T3 cells or Ltk⁻ cells may be used as immunogens to raise such an antibody. Alternatively, synthetic peptides may be prepared using commercially available machines and the amino acid sequences shown in FIGS. 1A–1I, 2A–2H, and 3A–3G. As a still further alternative, DNA, such as a cDNA or a fragment thereof, may be cloned and expressed and the resulting polypeptide recovered and used as an immunogen. These antibodies are useful to detect the presence of human $\alpha_1$ adrenergic receptors encoded by the isolated DNA, or to inhibit the function of $\alpha_1$ adrenergic receptors in living animals, in humans, or in biological tissues or fluids isolated from animals or humans.

This invention provides a pharmaceutical composition which comprises an effective amount of an antibody directed to an epitope of a human $\alpha_{1a}$ adrenergic receptor, effective to block binding of naturally occurring substrates to the human $\alpha_{1a}$ adrenergic receptor and a pharmaceutically acceptable carrier. A monoclonal antibody directed to an epitope of a human $\alpha_{1a}$ adrenergic receptor present on the surface of a cell which has an amino acid sequence substantially the same as an amino acid sequence for a cell surface epitope of the human $\alpha_{1a}$ adrenergic receptor included in the amino acid sequence shown in FIGS. 1A–1I is useful for this purpose. This invention also provides a pharmaceutical composition which comprises an effective amount of an antibody directed to an epitope of a human $\alpha_{1b}$ adrenergic receptor, effective to block binding of naturally occurring substrates to the human $\alpha_{1b}$ adrenergic receptor and a pharmaceutically acceptable carrier. A monoclonal antibody directed to an epitope of a human $\alpha_{1b}$ adrenergic receptor present on the surface of a cell which has an amino acid sequence substantially the same as an amino acid sequence for a cell surface epitope of the human adrenergic receptor included in the amino acid sequence shown in FIGS. 2A–2H is useful for this purpose. This invention provides a pharmaceutical composition which comprises an effective amount of an antibody directed to an epitope of a human $\alpha_{1c}$ adrenergic receptor, effective to block binding of naturally occurring substrates to the human $\alpha_{1c}$ adrenergic receptor and a pharmaceutically acceptable carrier. A monoclonal antibody directed to an epitope of a human $\alpha_{1c}$ adrenergic receptor present on the surface of a cell which has an amino acid sequence substantially the same as an amino acid sequence for a cell surface epitope of the human $\alpha_{1c}$ adrenergic receptor included in the amino acid sequence shown in FIGS. 3A–3G is useful for this purpose.

This invention also provides a method of treating abnormalities in a subject which are alleviated by reduction of expression of a specific human $\alpha_1$ adrenergic receptor. The method comprises administering to the subject an effective amount of the pharmaceutical composition described above effective to block binding of naturally occurring substrates to the human $\alpha_1$ adrenergic receptor and thereby alleviate abnormalities resulting from overexpression of the human $\alpha_1$ adrenergic receptor. Binding of the antibody to the human $\alpha_1$ adrenergic receptor prevents the human $\alpha_1$ adrenergic receptor from functioning, thereby neutralizing the effects of overexpression. The monoclonal antibodies described above are useful for this purpose. This invention additionally provides a method of treating an abnormal condition related to an excess of a specific human $\alpha_1$ adrenergic receptor activity which comprises administering to a subject an amount of the pharmaceutical composition described above effective to block binding of naturally occurring substrates to the human $\alpha 1$ adrenergic receptor and thereby alleviate the abnormal condition. An example of an abnormal condition associated with excess human $\alpha 1$ adrenergic receptor activity is benign prostatic hypertrophy.

This invention provides methods of detecting the presence of a specific human $\alpha 1$ adrenergic receptor on the surface of a cell which comprises contacting the cell with an antibody directed to a specific human $\alpha 1$ adrenergic receptor, under conditions permitting binding of the antibody to the human $\alpha 1$ adrenergic receptor, detecting the presence of any antibody bound to the $\alpha 1$ adrenergic receptor, and thereby the presence of the specific human $\alpha 1$ adrenergic receptor on the surface of the cell. Such methods are useful for determining whether a given cell is defective in expression of a specific human adrenergic receptor. Bound antibodies are detected by methods well known in the art, for example by binding fluorescent markers to the antibodies and examining the cell sample under a fluorescence microscope to detect fluorescence on a cell indicative of antibody binding. The monoclonal antibodies described above are useful for this purpose.

This invention provides a transgenic nonhuman mammal comprising DNA encoding a human $\alpha_{1a}$ adrenergic receptor. This invention also provides a transgenic nonhuman mammal comprising DNA encoding a human $\alpha_{1b}$ adrenergic receptor. This invention also provides a transgenic nonhuman mammal comprising DNA encoding a human $\alpha_{1c}$ adrenergic receptor.

This invention also provides a transgenic nonhuman mammal comprising DNA encoding a human $\alpha_{1a}$ adrenergic receptor so mutated as to be incapable of normal human $\alpha_{1a}$ adrenergic receptor activity, and not expressing native human $\alpha 1a$ adrenergic receptor. This invention also provides a transgenic nonhuman mammal comprising DNA encoding a human $\alpha_{1b}$ adrenergic receptor so mutated as to be incapable of normal human $\alpha 1b$ adrenergic receptor activity, and not expressing native human $\alpha 1b$ adrenergic receptor. This invention also provides a transgenic nonhuman mammal comprising DNA encoding a human $\alpha_{1c}$ adrenergic receptor so mutated as to be incapable of normal human $\alpha 1c$ adrenergic receptor activity, and not expressing native human $\alpha 1c$ adrenergic receptor.

This invention provides a transgenic non-human animal whose genome comprises DNA encoding a human $\alpha_{1a}$ adrenergic receptor so placed as to be transcribed into antisense mRNA which is complementary to mRNA encoding a human $\alpha_{1a}$ adrenergic receptor and which hybridizes to mRNA encoding the human $\alpha_{1a}$ adrenergic receptor thereby reducing its translation. This invention also provides a transgenic nonhuman mammal whose genome comprises DNA encoding a human $\alpha_{1b}$ adrenergic receptor so placed as to be transcribed into antisense mRNA which is complementary to mRNA encoding the human $\alpha_{1b}$ adrenergic receptor and which hybridizes to mRNA encoding a human $\alpha_{1b}$ adrenergic receptor thereby reducing its translation. This invention provides a transgenic non-human animal whose genome comprises DNA encoding a human $\alpha_{1c}$ adrenergic receptor so placed as to be transcribed into antisense mRNA which is complementary to mRNA encoding a human $\alpha_{1c}$ adrenergic receptor and which hybridizes to mRNA encoding the human $\alpha_{1c}$ adrenergic receptor thereby reducing its translation. The DNA may additionally comprise an inducible promoter or additionally comprise tissue specific regulatory elements, so that expression can be induced, or restricted to specific cell types. Examples of DNA are DNA or cDNA molecules having a coding sequence substantially the same as the coding sequences shown in FIGS. 1A–1I, 2A–2H, or 3A–3G. An example of a transgenic animal is a transgenic mouse. Examples of tissue specificity-determining regions are the metallothionein promotor (Low, M. J., Lechan, R. M., Hammer, R. E. et al. Science 231: 1002–1004 (1986)) and the L7 promotor (Oberdick, J., Smeyne, R. J., Mann, J. R., Jackson, S. and Morgan, J. I. Science 248: 223–226 (1990)).

Animal model systems which elucidate the physiological and behavioral roles of human $\alpha_1$ adrenergic receptors are produced by creating transgenic animals in which the expression of an $\alpha_1$ adrenergic receptor is either increased or decreased, or the amino acid sequence of the expressed $\alpha_1$ adrenergic receptor is altered, by a variety of techniques. Examples of these techniques include, but are not limited to: 1) Insertion of normal or mutant versions of DNA encoding a human $\alpha_1$ adrenergic receptor or homologous animal versions of these genes, by microinjection, retroviral infection or other means well known to those skilled in the art, into appropriate fertilized embryos in order to produce a transgenic animal (Hogan B. et al. Manipulating the Mouse Embryo, A Laboratory Manual, Cold Spring Harbor Laboratory (1986)) or, 2) Homologous recombination (Capecchi M. R. Science 244: 1288–1292 (1989); Zimmer, A. and Gruss, P. Nature 338: 150–153 (1989)) of mutant or normal, human or animal version of the genes encoding $\alpha 1$ adrenergic receptors with the native gene locus in transgenic animals to alter the regulation of expression or the structure $\alpha 1$ of these $\alpha_1$ adrenergic receptors. The technique of homologous recombination is well known in the art. It replaces the native gene with the inserted gene and so is useful for producing an animal that cannot express native $\alpha_1$ adrenergic receptor but does express, for example, an inserted mutant human $\alpha_1$ adrenergic receptor, which has replaced the native $\alpha_1$ adrenergic receptor in the animal's genome by recombination, resulting in underexpression of the $\alpha_1$ adrenergic receptor.

Microinjection adds genes to the genome, but does not remove them, and so is useful for producing an animal which expresses its own and added $\alpha_1$ adrenergic receptors, resulting in overexpression of the $\alpha_1$ adrenergic receptor.

One means available for producing a transgenic animal, with a mouse as an example, is as follows: Female mice are mated, and the resulting fertilized eggs are dissected out of their oviducts. The eggs are stored in an appropriate medium such as M2 medium (Hogan B. et al. Manipulating the Mouse Embryo, A Laboratory Manual, Cold Spring Harbor Laboratory (1986)). DNA or cDNA encoding a human $\alpha_1$ adrenergic receptor is purified from a vector (such as plasmids pCEXV-$\alpha_{1a}$, pCEXV-$\alpha_{1b}$, or pCEXV-$\alpha_{1c}$ described above) by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

Since the normal action of $\alpha_1$ adrenergic-specific drugs is to activate or to inhibit the $\alpha_1$ adrenergic receptor, the transgenic animal model systems described above are useful for testing the biological activity of drugs directed against specific human $\alpha_1$ adrenergic receptors even before such drugs become available. These animal model systems are useful for predicting or evaluating possible therapeutic applications of drugs which activate or inhibit these human $\alpha 1$ adrenergic receptors by inducing or inhibiting expression of the native or trans-gene and thus increasing or decreasing expression of normal or mutant human $\alpha_1$ adrenergic receptor in the living animal. Thus, a model system is produced in which the biological activity of drugs directed against these human $\alpha_1$ adrenergic receptors are evaluated before such drugs become available. The transgenic animals which over or under produce a specific human $\alpha_1$ adrenergic receptor indicate by their physiological state whether over or under production of the human $\alpha_1$ adrenergic receptor is therapeutically useful. It is therefore useful to evaluate drug action based on the transgenic model system. One use is based on the fact that it is well known in the art that a drug such as an antidepressant acts by blocking neurotransmitter uptake, and thereby increases the amount of neurotransmitter in the synaptic cleft. The physiological result of this action is to stimulate the production of less human $\alpha_1$ adrenergic receptor by the affected cells, leading eventually to underexpression. Therefore, an animal which underexpresses human $\alpha_1$ adrenergic receptor is useful as a test system to investigate whether the actions of such drugs which result in under expression are in fact therapeutic. Another use is that if overexpression is found to lead to abnormalities, then a drug which down-regulates or acts as an antagonist to the human $\alpha_1$ adrenergic receptor is indicated as worth developing, and if a promising therapeutic application is uncovered by these animal model systems, activation or inhibition of the specific human $\alpha_1$ adrenergic receptor is achieved therapeutically either by producing agonist or antagonist drugs directed against these human $\alpha_1$ adrenergic receptors or by any method which increases or decreases the expression of these $\alpha_1$ adrenergic receptors in man.

Further provided by this invention is a method of determining the physiological effects of expressing varying levels of a human $\alpha_1$ adrenergic receptor which comprises producing a transgenic nonhuman animal whose levels of $\alpha_1$ adrenergic receptor expression are varied by use of an inducible promoter which regulates human adrenergic receptor expression. This invention also provides a method of determining the physiological effects of expressing varying levels of human adrenergic receptors which comprises preproducing a panel of transgenic nonhuman animals each expressing a different amount of a human $\alpha_1$ adrenergic receptor. Such animals may be produced by introducing different amounts of DNA encoding a human $\alpha_1$ adrenergic receptor into the oocytes from which the transgenic animals are developed.

This invention also provides a method for identifying a substance capable of alleviating abnormalities resulting from overexpression of a human $\alpha_1$ adrenergic receptor comprising administering the substance to a transgenic nonhuman mammal expressing at least one artificially introduced DNA molecule encoding a human $\alpha_1$ adrenergic receptor and determining whether the substance alleviates the physical and behavioral abnormalities displayed by the transgenic nonhuman mammal as a result of overexpression of a human $\alpha_1$ adrenergic receptor. As used herein, the term "substance" means a compound or composition which may be natural, synthetic, or a product derived from screening. Examples of DNA molecules are DNA or cDNA molecules having a coding sequence substantially the same as the coding sequences shown in FIGS. 1A–1I, 2A–2H, or 3A–3G.

This invention provides a pharmaceutical composition comprising an amount of the substance described supra effective to alleviate the abnormalities resulting from overexpression of a human $\alpha_{1a}$ adrenergic receptor and a pharmaceutically acceptable carrier. This invention provides a pharmaceutical composition comprising an amount of the substance described supra effective to alleviate the abnormalities resulting from overexpression of a human $\alpha_{1b}$ adrenergic receptor and a pharmaceutically acceptable carrier. This invention also provides a pharmaceutical composition comprising an amount of the substance described supra effective to alleviate the abnormalities resulting from overexpression of a human $\alpha_{1c}$ adrenergic receptor and a pharmaceutically acceptable carrier.

This invention further provides a method for treating the abnormalities resulting from overexpression of a human $\alpha_1$ adrenergic receptor which comprises administering to a subject an amount of the pharmaceutical composition described above effective to alleviate the abnormalities resulting from overexpression of the human $\alpha_1$ adrenergic receptor.

This invention provides a method for identifying a substance capable of alleviating the abnormalities resulting from underexpression of a human $\alpha_1$ adrenergic receptor comprising administering the substance to the transgenic nonhuman mammal described above which expresses only a nonfunctional human $\alpha_1$ adrenergic receptor and determining whether the substance alleviates the physical and behavioral abnormalities displayed by the transgenic nonhuman mammal as a result of underexpression of the human $\alpha_1$ adrenergic receptor.

This invention also provides a pharmaceutical composition comprising an amount of a substance effective to alleviate abnormalities resulting from underexpression of a human $\alpha_1$ adrenergic receptor and a pharmaceutically acceptable carrier.

This invention further provides a method for treating the abnormalities resulting from underexpression of a human $\alpha_1$ adrenergic receptor which comprises administering to a subject an amount of the pharmaceutical composition described above effective to alleviate the abnormalities resulting from underexpression of a human $\alpha_1$ adrenergic receptor.

This invention provides a method for diagnosing a predisposition to a disorder associated with the expression of a specific human $\alpha_1$ adrenergic receptor allele which comprises: a) obtaining DNA of subjects suffering from the disorder; b) performing a restriction digest of the DNA with a panel of restriction enzymes; c) electrophoretically separating the resulting DNA fragments on a sizing gel; d)

contacting the resulting gel with a nucleic acid probe capable of specifically hybridizing to DNA encoding a human $\alpha_1$ adrenergic receptor and labelled with a detectable marker; e) detecting labelled bands which have hybridized to the DNA encoding a human $\alpha_1$ adrenergic receptor labelled with a detectable marker to create a unique band pattern specific to the DNA of subjects suffering from the disorder; f) preparing DNA obtained for diagnosis by steps a–e; and g) comparing the unique band pattern specific to the DNA of subjects suffering from the disorder from step e and the DNA obtained for diagnosis from step f to determine whether the patterns are the same or different and thereby to diagnose predisposition to the disorder if the patterns are the same. This method may also be used to diagnose a disorder associated with the expression of a specific human $\alpha_1$ adrenergic receptor allele.

This invention provides a method of preparing an isolated human $\alpha_1$ adrenergic receptor which comprises inducing cells to express the human $\alpha_1$ adrenergic receptor, recovering the $\alpha_1$ adrenergic receptor from the resulting cells, and purifying the $\alpha_1$ adrenergic receptor so recovered. An example of an isolated human $\alpha_{1a}$ adrenergic receptor is an isolated protein having substantially the same amino acid sequence as the amino acid sequence shown in FIGS. 1A–1I. An example of an isolated human $\alpha_{1b}$ adrenergic receptor is an isolated protein having substantially the same amino acid sequence shown in FIG. 2A–2H. An example of an isolated human $\alpha_{1c}$ adrenergic receptor is an isolated protein having substantially the same amino acid sequence shown in FIG. 3A–3G. For example, cells can be induced to express human $\alpha_1$ adrenergic receptors by exposure to substances such as hormones. The cells can then be homogenized and the human $\alpha_1$ adrenergic receptor isolated from the homogenate using an affinity column comprising, for example, epinephrine, norepinephrine, or another substance which is known to bind to the human $\alpha_1$ adrenergic receptor. The resulting fractions can then be purified by contacting them with an ion exchange column, and determining which fraction contains human $\alpha_1$ adrenergic receptor activity or binds anti-human $\alpha1$ adrenergic receptor antibodies.

This invention provides a method of preparing the isolated human $\alpha_{1a}$ adrenergic receptor which comprises inserting nucleic acid encoding the human $\alpha_{1a}$ adrenergic receptor in a suitable vector, inserting the resulting vector in a suitable host cell, recovering the $\alpha_{1a}$ adrenergic receptor produced by the resulting cell, and purifying the $\alpha_{1a}$ adrenergic receptor so recovered. An example of an isolated human $\alpha_{1a}$ adrenergic receptor is an isolated protein having substantially the same amino acid sequence as the amino acid sequence shown in FIGS. 1A–1I. This invention also provides a method of preparing the isolated human $\alpha_{1b}$ adrenergic receptor which comprises inserting nucleic acid encoding the human adrenergic receptor in a suitable vector, inserting the resulting vector in a suitable host cell, recovering the $\alpha_{1b}$ adrenergic receptor produced by the resulting cell, and purifying the $\alpha_{1b}$ adrenergic receptor so recovered. This invention also provides a method of preparing the isolated human $\alpha_{1c}$ adrenergic receptor which comprises inserting nucleic acid encoding the human $\alpha_{1c}$ adrenergic receptor in a suitable vector, inserting the resulting vector in a suitable host cell, recovering the adrenergic receptor produced by the resulting cell, and purifying the $\alpha_{1c}$ adrenergic receptor so recovered. These methods for preparing human $\alpha_1$ adrenergic receptors uses recombinant DNA technology methods well known in the art. For example, isolated nucleic acid encoding a human $\alpha_1$ adrenergic receptor is inserted in a suitable vector, such as an expression vector. A suitable host cell, such as a bacterial cell, or a eukaryotic cell such as a yeast cell, is transfected with the vector. The human $\alpha_1$ adrenergic receptor is isolated from the culture medium by affinity purification or by chromatography or by other methods well known in the art.

This invention provides a method of determining whether a ligand not known to be capable of binding to a human $\alpha_1$ adrenergic receptor can bind to a human $\alpha_1$ adrenergic receptor, which comprises contacting a mammalian cell comprising a plasmid adapted for expression in a mammalian cell which further comprises a DNA molecule which expresses a human $\alpha_1$ adrenergic receptor on the cell surface with the ligand under conditions permitting binding of ligands known to bind to the human $\alpha_1$ adrenergic receptor, detecting the presence of any ligand bound to the human $\alpha_1$ adrenergic receptor and thereby determining whether the ligand binds to the human $\alpha_1$ adrenergic receptor. The DNA in the cell may have a coding sequence substantially the same as the coding sequences shown in FIGS. 1A–1I, 2A–2H, or 3A–3G, preferably, the mammalian cell is nonneuronal in origin. An example of a nonneuronal mammalian cell is a Cos7 cell. The preferred method for determining whether a ligand is capable of binding to the human $\alpha_1$ adrenergic receptor comprises contacting a transfected nonneuronal mammalian cell (i.e. a cell that does not naturally express any type of human $\alpha_1$ adrenergic receptor, thus will only express such human $\alpha_1$ adrenergic receptor if it is transfected into the cell) expressing a human $\alpha_1$ adrenergic receptor on its surface, or contacting a membrane preparation derived from such a transfected cell, with the ligand under conditions which are known to to prevail, and thus to be associated with in vivo binding of the substrates to a human $\alpha1$ adrenergic receptor, detecting the presence of any of the ligand being tested bound to the human $\alpha_1$ adrenergic receptor on the surface of the cell, and thereby determining whether the ligand binds to the human $\alpha_1$ adrenergic receptor. This response system is obtained by transfection of isolated DNA into a suitable host cell. Such a host system might be isolated from pre-existing cell lines, or can be generated by inserting appropriate components into existing cell lines. Such a transfection system provides a complete response system for investigation or assay of the functional activity of human $\alpha_1$ adrenergic receptors with ligands as described above. Transfection systems are useful as living cell cultures for competitive binding assays between known or candidate drugs and substrates which bind to the human $\alpha_1$ adrenergic receptor and which are labeled by radioactive, spectroscopic or other reagents. Membrane preparations containing the transporter isolated from transfected cells are also useful for these competitive binding assays. A transfection system constitutes a "drug discovery system" useful for the identification of natural or synthetic compounds with potential for drug development that can be further modified or used directly as therapeutic compounds to activate or inhibit the natural functions of a specific human $\alpha_1$ adrenergic receptor. The transfection system is also useful for determining the affinity and efficacy of known drugs at human $\alpha_1$ adrenergic receptor binding sites.

This invention provides a method for identifying a ligand which interacts with, and activates or blocks the activation of, a human $\alpha_1$ adrenergic receptor on the surface of a cell, which comprises contacting a mammalian cell which comprises a plasmid adapted for expression in a mammalian cell which further comprises a DNA molecule which expresses a human $\alpha_1$ adrenergic receptor on the cell surface with the ligand, determining whether the ligand activates or blocks the activation of the receptor using a bioassay such as second messenger assays, and thereby identifying a ligand which interacts with, and activates or blocks the activation of, a human $e_1$ adrenergic receptor.

This invention provides functional assays for identifying ligands and drugs which bind to and activate or inhibit a specific human α1 adrenergic receptor activity.

This invention provides a method for identifying a ligand which is capable of binding to and activating or inhibiting a human $\alpha_1$ adrenergic receptor, which comprises contacting a mammalian cell, wherein the membrane lipids have been labelled by prior incubation with a labelled lipid precursor molecule, the mammalian cell comprising a plasmid adapted for expression in a mammalian cell which further comprises a DNA molecule which expresses a human $\alpha_1$ adrenergic receptor with the ligand and identifying an inositol phosphate metabolite released from the membrane lipid as a result of ligand binding to and activating an $\alpha_1$ adrenergic receptor.

This invention provides method for identifying a ligand that is capable of binding to and activating or inhibiting a human $\alpha_1$ adrenergic receptor, wherein the binding of ligand to the adrenergic receptor results in a physiological response, which comprises contacting a mammalian cell which comprises a plasmid adapted for expression in a mammalian cell which further comprises a DNA molecule which expresses a human $\alpha_1$ adrenergic receptor with a calcium sensitive fluorescent indicator, removing the indicator that has not been taken up by the cell, contacting the cells with the ligand and identifying an increase or decrease in intracellular $Ca^{2+}$ as a result of ligand binding to and activating receptor.

Transformed mammalian cells for identifying the ligands and drugs that affect the functional properties of the human α adrenergic receptors include 293-α1a-10, C-α1b-6 and C-α1c-7.

This invention also provides a method of screening drugs to identify drugs which interact with, and bind to, a human $\alpha_1$ adrenergic receptor on the surface of a cell, which comprises contacting a mammalian cell which comprises a plasmid adapted for expression in a mammalian cell which further comprises a DNA molecule which expresses a human $\alpha_1$ adrenergic receptor on the cell surface with a plurality of drugs, determining those drugs which bind to the human $\alpha_1$ adrenergic receptor expressed on the cell surface of the mammalian cell, and thereby identifying drugs which interact with, and bind to, the human $\alpha_1$ adrenergic receptor. Various methods of detection may be employed. The drugs may be "labeled" by association with a detectable marker substance (e.g., radiolabel or a non-isotopic label such as biotin). The DNA in the cell may have a coding sequence substantially the same as the coding sequences shown in FIGS. 1A–1I, 2A–2H or 3A–3G. Preferably, the mammalian cell is nonneuronal in origin. An example of a nonneuronal mammalian cell is a Cos7 cell. Drug candidates are identified by choosing chemical compounds which bind with high affinity to the human $\alpha_1$ adrenergic receptor expressed on the cell surface in transfected cells, using radioligand binding methods well known in the art, examples of which are shown in the binding assays described herein. Drug candidates are also screened for selectivity by identifying compounds which bind with high affinity to one particular human $\alpha_1$ adrenergic receptor subtype but do not bind with high affinity to any other human $\alpha_1$ adrenergic receptor subtype or to any other known receptor site. Because selective, high affinity compounds interact primarily with the target human $\alpha_1$ adrenergic site after administration to the patient, the chances of producing a drug with unwanted side effects are minimized by this approach. This invention provides a pharmaceutical composition comprising a drug identified by the method described above and a pharmaceutically acceptable carrier. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. Once the candidate drug has been shown to be adequately bio-available following a particular route of administration, for example orally or by injection (adequate therapeutic concentrations must be maintained at the site of action for an adequate period to gain the desired therapeutic benefit), and has been shown to be non-toxic and therapeutically effective in appropriate disease models, the drug may be administered to patients by that route of administration determined to make the drug bio-available, in an appropriate solid or solution formulation, to gain the desired therapeutic benefit.

Applicants have identified individual human $\alpha_1$ adrenergic receptor subtypes and have described methods for the identification of pharmacological compounds for therapeutic treatments. Pharmacological compounds which are directed against a specific human $\alpha_1$ adrenergic receptor subtype provide effective new therapies with minimal side effects.

Elucidation of the molecular structures of the neuronal human $\alpha_1$ adrenergic receptors transporters is an important step in the understanding of α-adrenergic neurotransmission. This disclosure reports the isolation, the nucleic acid sequence, and functional expression of DNA clones isolated from human brain which encode human $\alpha_1$ adrenergic receptors. The identification of these human $\alpha_1$ adrenergic receptors will play a pivotal role in elucidating the molecular mechanisms underlying α-adrenergic transmission, and should also aid in the development of novel therapeutic agents.

DNA clones encoding human $\alpha_1$ adrenergic receptors have been isolated from human brain, and their functional properties have been examined in mammalian cells.

This invention identifies for the first time three new human $\alpha_1$ adrenergic receptors, their amino acid sequences, and their human genes. The information and experimental tools provided by this discovery are useful to generate new therapeutic agents, and new therapeutic or diagnostic assays for these new human receptors, their associated mRNA molecules or their associated genomic DNAs. The information and experimental tools provided by this discovery will be useful to generate new therapeutic agents, and new therapeutic or diagnostic assays for these new human receptors, their associated mRNA molecules, or their associated genomic DNAs.

Specifically, this invention relates to the first isolation of human DNA clones encoding encoding three $\alpha_1$-adrenergic receptors. In addition, the human $\alpha_1$ adrenergic receptors have been expressed in mammalian cells by transfecting the cells with the plasmids pCEXV-$\alpha_{1a}$, pCEXV-$\alpha_{1b}$, and pCEXV-$\alpha_{1c}$. The pharmacological binding properties of these receptor proteins have been determined, and these binding properties classify these receptor proteins as $\alpha_1$ adrenergic receptors. Mammalian cell lines expressing the human $\alpha_1$ adrenergic receptors on the cell surface have been constructed, thus establishing the first well-defined, cultured cell lines with which to study human α1 adrenergic receptors. Examples of transformed mammalian cells, expressing human $\alpha_1$ adrenergic receptors are L-α1a (ATCC Accession No. CRL 11138), expressing a human α1a adrenergic receptor, L-α1c (ATCC Accession No. CRL 11139) expressing a human α1b adrenergic receptor, and L-α1c (ATCC Accession No. CRL 11140) expressing a human α1c adrenergic receptor. These cells are suitable for studying the pharmacological properties of the human α1 adrenergic receptors and for the screening of ligands and drugs that specifically bind to human α1 adrenergic receptor subtypes.

The deposits discussed supra were made Sep. 25, 1992 pursuant to, and in satisfaction of, the provisions of the Budapest Treaty on the International Recognition of the Deposit of Microorganisms for the Purpose of Patent Procedure with the American Type Culture Collection (ATCC), 12301 Parklawn Drive, Rockville, Md. 20852.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

MATERIALS AND METHODS

Cloning and Sequencing

α1a: A human lymphocyte genomic library in λ dash II (≈1.5×10$^6$ total recombinants; Stratagene, LaJolla, Calif.) was screened using a cloned rat PCR fragment (RBNC2) as a probe. RBNC2 was obtained by amplifying randomly-primed rat brain cDNA with degenerate primers designed to conserved regions of transmembrane (Tm) regions 3 and 6 of serotonin receptors. The sequence of one PCR product, RBNC2, exhibited strong homology to the α1 AR family.

The probe was labeled with [$^{32}$P] by the method of random priming (5) (Prime-It Random Primer kit, Stratagene, LaJolla, Calif.). Hybridization was performed at 40° C. in a solution containing 50% formamide, 10% dextran sulfate, 5×SSC (1× SSC is 0.15M sodium chloride, 0.015M sodium citrate), 1× Denhardt's solution (0.02% polyvinylpyrrolidone, 0.02% Ficoll, 0.02% bovine serum albumin), and 200 μg/μl sonicated salmon sperm DNA. The filters were washed at 50° C. in 0.1× SSC containing 0.1% sodium dodecyl sulfate and exposed at −70° C. to Kodak XAR film in the presence of an intensifying screen. Lambda phage clones hybridizing with the probe were plaque purified and DNA was prepared for Southern blot analysis (22,17). For subcloning and further Southern blot analysis, DNA was cloned into pUC18 (Pharmacia, Piscataway, N.J.) or pBluescript (Stratagene, LaJolla, Calif.). Nucleotide sequence analysis was accomplished by the Sanger dideoxy nucleotide chain termination method (18) on denatured double-stranded plasmid templates, using Sequenase (US Biochemical Corp., Cleveland, Ohio), Bst DNA sequencing kit (Bio-Rad Laboratories, Richmond, Calif.), or TaqTrack sequencing kit (Promega Corporation, Madison, Wis.).

In order to isolate a full-length clone, human cDNA libraries were screened by polymerase chain reaction (PCR) with 1 μM each of specific oligonucleotide primers designed off the isolated genomic clone: from the sense strand (nucleotide 598–626), 5' CACTCAAGTACCCAGCCAT-CATGAC 3' and from the anti-sense strand (nucleotide 979–1003), 5' CGGAGAGCGAGCTGCGGAAGGTGTG 3' (see FIGS. 1A–1I). The primers were from non-conserved portions of the receptor gene, specifically in the Tm3–Tm4 loop and in the Tm5–Tm6 loop regions for the upstream and downstream primers, respectively. One to 2 μl of phage DNA from cDNA libraries (λ ZapII; Stratagene, LaJolla, Calif.), representing ≈10$^6$–10$^7$ pfu, were amplified in 10 mM Tris-HCl, pH 8.3, 50 mM KCl, 1.5 μM MgCl2, 0.01% gelatin, 200 μM each dATP, dCTP, dGTP, dTTP, 2.5 units of Thermus aquaticus DNA polymerase (Taq polymerase; Perkin-Elmer-Cetus, Norwalk, Conn.). The amplification profile was run for 30 cycles: a 5 min. initial (ie. 1 cycle) denaturation at 95° C., followed by 2 min. at 94° C., 2 min. at 68° C., and 3 min. at 72° C., with a 3 sec. extension, followed by a final 10 min. extension at 72° C. PCR products were analyzed by ethidium bromide (EtBr) stained agarose gels and any sample exhibiting a band on the EtBr stained gel was considered positive.

A positive library was then plated and screened with overlapping 45-mer oligonucleotide probes, filled-in using [α-$^{32}$P]dCTP and [α-$^{32}$P]dATP and Klenow fragment of DNA polymerase. This probe was internal to the amplification primers discussed above: from the sense strand (nucleotide 890–934), 5 ' GCAAGGCCTCCGAGGTGGT-GCTGCGCATCCACTGTCGCGGCGCGG 3', and from the anti-sense strand (nucleotide 915–961), 5 ' TGCCGT-GCGCCCCGTCGGCGCCCGTGGCCGCGC-CGCGACAGTGGATG 3' (see FIGS. 1A–1I). Positive cDNA phage clones were plaque purified and pBluescript recombinant DNAs were excision-rescued from λ Zap II using helper phage R408, as described by manufacturer's protocol (Stratagene, LaJolla, Calif.). Insert size was confirmed by restriction enzyme digest analysis and recombinants were sequenced, as described above.

α1b: A human placenta genomic library in λ dash II (≈1.5×10$^6$ total recombinants; Stratagene, LaJolla, Calif.) was screened using overlapping 45-mer oligonucleotides radiolabeled as described above and directed to the third, fifth and sixth transmembrane regions of serotonin 5HT1Dβ receptor gene. Hybridization and washing conditions were identical to that described for α1a above except lower stringency hybridization and washes were conducted; specifically, hybridization in 25% formamide and washes at 40° C.

Positive-hybridizing λ phage clones were plaque-purified, analyzed by Southern blot analysis, subcloned and sequenced, as described above for α1a. In order to isolate full-length clones, human cDNA libraries in λ Zap II (Stratagene, LaJolla, Calif.) were screened by polymerase chain reaction as described above. The upstream and downstream PCR primers used were from the Tm4–Tm5 loop and the Tm5–Tm6 loop, respectively: from the sense strand (nucleotide 567–593), 5' CAACGATGACAAGGA GTGCGGGGTCAC 3', and from the antisense strand (nucleotide 822–847), 5' TTTGACAGCTATGGAACTC-CTGGGG 3' (see FIG. 2). PCR, library screen, plaque purification excision-rescue from λ Zap II, restriction digestions and sequencing were accomplished as described above for α1a. The internal probe was: from the sense strand (nucleotide 745–789), 5' AAGGAGCTGACCCTGAG-GATCCATTCCAAGAACTTTCACGAGGAC 3', and from the anti-sense strand (nucleotide 770–814), 5' CCTTGGC-CTTGGTACTGCTAAGGGTGTCCTCGT-GAAAGTTCTTGG 3' (see FIGS. 2A–2H).

α1c: A human lymphocyte genomic library in λ dash II (≈1.5×10$^6$ total recombinants; Stratagene, LaJolla, Calif.) was screened using overlapping 45-mer oligonucleotides radiolabeled as described for α1a and directed to the third, fifth and sixth transmembrane regions of serotonin 5HT1A receptor gene. Hybridization and washing conditions were identical to that described for α1b. Positive-hybridizing λ phage clones were plaque-purified, analyzed by Southern blot analysis, subcloned and sequenced, as described above for α1a. Identification and isolation of full-length clones by PCR and screening cDNA libraries were accomplished as described for α1b. The upstream and downstream PCR primers used were from the Tm3–Tm4 loop and the Tm5–Tm6 loop, respectively: from the sense strand (nucleotide 403–425) , 5' CCAACCATCGTCACCCA-GAGGAG 3', and from the antisense strand (nucleotide 775–802), 5' TCTCCCGGGAGAACTTGAGGAGCCT-CAC 3' (see FIGS. 3A–3G). The internal probe was: from the sense strand (nucleotide 711–745), 5' TCCGCATC-CATCGGAAAAACGCCCCGGCAGGAG-GCAGCGGGATGG 3', and from the anti-sense strand (nucleotide 726–771), 5' GAAGTGCGTCTTGGTCTTG-GCGCTGGCCATCCCGCTGCCTCCTGCC 3 ' (see FIGS. 3A–3G). PCR, library screen, plaque purification excision-rescue from λ Zap II, restriction digestions and sequencing were accomplished as described above for α1a.

Expression

α1a: The entire coding region of α1a (1719 bp), including 150 basepairs of 5' untranslated sequence (5' UT) and 300 bp of 3' untranslated sequence (3' UT), was cloned into the BamHI and ClaI sites of the polylinker-modified eukaryotic expression vector pCEXV-3 (13), called EXJ.HR (unpublished data). The construct involved the ligation of partial overlapping human lymphocyte genomic and hippoc-amppal cDNA clones: 5' sequences were contained on a 1.2 kb SmaI-XhoI genomic fragment (the vector-derived BamHI site was used for subcloning instead of the internal insert-derived SmaI site) and 3' sequences were contained on an 1.3 kb XhoI-ClaI cDNA fragment (the ClaI site was from the vector polylinker). Stable cell lines were obtained by cotransfection with the plasmid α1a/EXJ (expression vector containing the α1a receptor gene) and the plasmid pGCcos3neo (plasmid containing the aminoglycoside transferase gene) into LM(tk−), CHO, NIH3T3 cells and 293 cells using calcium phosphate technique. The cells were grown, in a controlled environment (37° C., 5% $CO_2$), as monolayers in Dulbecco's modified Eagle's Medium (GIBCO, Grand Island, N.Y.) containing 25 mM glucose and supplemented with 10% bovine calf serum, 100 units/ml penicillin G, and 100 μg/ml streptomycin sulfate. Stable clones were then selected for resistance to the antibiotic G-418 (1 mg/ml) as described previously (26) and membranes were harvested and assayed for their ability to bind [$^3$H]prazosin as described below (see "Radioligand Binding Assays").

α1b: The entire coding region of α1b (1563 bp), including 200 basepairs of 5' untranslated sequence (5' UT) and 600 bp of 3' untranslated sequence (3' UT), was cloned into the EcoRI site of pCEXV-3 eukaryotic expression vector (5). The construct involved ligating the full-length containing EcoRI brainstem cDNA fragment from λ ZapII into the expression vector. Stable cell lines were selected as described above.

α1c: The entire coding region of α1c (1401 bp), including 400 basepairs of 5' untranslated sequence (5' UT) and 200 bp of 3' untranslated sequence (3' UT), was cloned into the KpnI site of the polylinker-modified pCEXV-3-derived (13) eukaryotic expression vector, EXJ.RH (unpublished data). The construct involved ligating three partial overlapping fragments: a 5' 0.6 kb HincII genomic clone, a central 1.8 EcoRI hippocamppal cDNA clone, and a 3' 0.6kb PstI genomic clone. The hippocamppal cDNA fragment overlaps with the 5' and 3' genomic clones so that the HincII and PstI sites at the 5' and 3' ends of the cDNA clone, respectively, were utilized for ligation. This full-length clone was cloned into the KpnI site of the expression vector, using the 5' and 3' KpnI sites of the fragment, derived from vector (ie. pBluescript) and 3' untranslated sequences, respectively. Stable cell lines were selected as described above.

Radioligand Binding Assays

Transfected cells from culture flasks were scraped into 5 ml of 5 mM Tris-HCl, 5 mM EDTA, pH 7.5, and lysed by sonication. The cell lysates were centrifuged at 1000 rpm for 5 min at 4° C., and the supernatant was centrifuged at 30,000×g for 20 min at 4° C. The pellet was suspended in 50 mM Tris-HCl, 1 mM $MgCl_2$, and 0.1% ascorbic acid at pH 7.5. Binding of the α1 antagonist [$^3$H]prazosin (0.5 nM, specific activity 76.2 Ci/mmol) to membrane preparations of LM(tk−) cells was done in a final volume of 0.25 ml and incubated at 37° C. for 20 min. Nonspecific binding was determined in the presence of 10 μM phentolamine. The reaction was stopped by filtration through GF/B filters using a cell harvester. Data were analyzed by a computerized non-linear regression program.

Measurement of [$^3$H]Inositol Phosphates (IP) Formation

Cells were suspended in Dulbecco's phosphate buffered saline (PBS), and incubated with 5 μCi/ml [$^3$H]m-inositol for 60 min at 37° C. The unincorporated radioactivity was removed by low speed centrifugation, and the cells were suspended in PBS containing 10 mM LiCl and the reaction was started by adding the agonist. After incubation for 60 min at 37° C., the reaction was stopped by adding $CHCl_3$:Methanol:HCl (2/1/0.01 v/v). Total [$^3$H]IP were separated by ion exchange chromatography and quantified as described by Forray and El-Fakahany (7).

Calcium Measurements

Intracellular calcium levels ([$Ca^{2+}$]i) were determined with the calcium-sensitive dye fura-2, and microspectrofluorometry, essentially as previously described (1,3). Briefly, cells were plated into polylysine-coated coverslip bottom dishes (MatTek Corporation, Ashland Mass.). To load with fura-2, cells were washed 3× with HEPES-buffered saline (HBS, in mM: HEPES, 20; NaCl, 150; KCl, 5; $CaCl_2$, 1; $MgCl_2$, 1; glucose, 10; pH 7.4) and incubated for 30 minutes at room temperature with fura-2 loading solution (5 uM fura-2/AM, 0.03% plutonit F-127, and 2% heat-inactivated fetal calf serum, in HBS). After loading, cells were washed 3× with HBS, 1 ml of HBS was added, and the dish was placed on the microscope for determination of [$Ca^{2+}$]$_i$. [$Ca^{2+}$]$_i$ was measured with a Leitz Fluovert microscope equipped for UV-transmission epifluorescence. Fura-2 fluorescence was alternately excited at 340 and 380 nm (0.25 sec), and a pair of readings (500 nm long pass) was taken every two seconds, and recorded by a personal computer interfaced to a data acquisition and control unit from Kinetek (Yonkers, N.Y.). To determine [$Ca^{2+}$]$_i$ from the experimental data the background fluorescence was subtracted, and the corrected ratios were converted to [$Ca^{2+}$]$_i$ by comparison with buffers containing saturating and low free calcium, assuming a $K_D$ of 400 nM (3).

RESULTS

α1a: We screened a human genomic lymphocyte library with a rat PCR fragment that exhibited homology with the α1-AR family. A total of six clones were isolated and characterized by Southern blot analysis. One clone, h13, contained a 4.0 kb XbaI fragment which hybridized with the radiolabeled rat PCR fragment and was subsequently subcloned into pUC vector. DNA sequence analysis indicated greatest homology to human α1a and rat =1a ARs. This clone contained the initiating methionine through Tm6 with ≈1.0–1.5 kb 5' UT region. Subsequent Southern blot, analysis, subcloning and sequencing analysis indicated the presence of a SmaI site ≈150 nts. 5' to the initiating methionine codon. The homology between h13 and rat α1a adrenergic gene breaks just downstream of Tm6 indicating an intron which is located in an analogous region in the α1b- and α1c-genes (4,20). In order to obtain a full-length clone, aliquots of human cDNA libraries totaling ≈1.5×10$^6$ recombinants was screened by polymerase chain reaction using specific oligonucleotide primers from sequence determined off the genomic clone (see Materials and Methods). A positive-containing human hippocamppal cDNA library (Stratagene, LaJolla, Calif.) in λ ZapII (≈1.5×10$^6$ recombinants) was screened using traditional plaque hybridization with an internal probe (see Materials and Methods) and resulted in the isolation of two positive cDNA clones, one containing the upstream sequences (from 5' UT through the 5–6 loop; hH22) and the other containing downstream sequences (from within Tm5 through ≈300 bp 3' UT; hH14). These two clones overlap by ≈200 nts. with a common XhoI site being present within this common region.

The complete full-length gene was constructed by splicing together two restriction fragments, one being the 3' cDNA (hH14) and the other being the 5' genomic clone (h13), using a unique restriction site (XhoI) present in the overlapping region. In addition, another construct was accomplished by ligating the two cDNA clones (hH14 and hH22), using the overlapping XhoI site; however, since this construct produced the same pharmacology as the genomic/cDNA construct, we will not discuss this recombinant (unpublished observation). The genomic/cDNA construct contains an open reading frame of 1719 bp and encoding a protein of 572 aa in length, having a relative molecular mass of ≈63,000 daltons. Hydropathy analysis of the protein is consistent with a putative topography of seven transmembrane domains, indicative of the G protein-coupled receptor family. Initial sequence analysis revealed that clone α1a/EXJ was most related to an AR since it contained a number of conserved structural features/residues found among the members of the adrenergic receptor family, including conserved cysteines in the second and third extracellular loops, a conserved glycine residue in Tm1, aspartic acid residues in Tm regions II and III, conserved valine residues in TmIII, the DRY sequence at the end of TmIII, the conserved proline residues of Tm regions II, IV, V, VI and VII, and the consensus D-V-L-X-X-T-X-S-I-X-X-L-C in Tm3 and the consensus G-Y-X-N-S-X-X-N-P-X-I-Y in Tm VII, both consensus unique to the adrenergic receptor family (8,12). Other features of this human α1a receptor gene are the presence of two potential sites for N-linked glycosylation in the amino terminus (asparagine residues 65 and 82; FIGS. 1a–II) and the presence of several serines and threonines in the carboxyl terminus and intracellular loops, which may serve as sites for potential phosphorylation by protein kinases.

α1b: We screened a human genomic placenta library with probes derived from Tm3, 5 and 6 regions of serotonin 5HT1D$_\beta$ under low stringency. Out of several hundred positive clones pursued by Southern blot analysis, subcloning and sequencing, one resembled the α1 adrenergic family of receptors. This genomic fragment contained Tm3 through Tm6 of a receptor which was most closely related to rat and hamster α1b receptors. In order to obtain a full-length clone, several human cDNA libraries were screened by PCR using primers derived from the 5–6 loop region of the genomic clone (see Materials and Methods). A positive-containing human brainstem cDNA library (Stratagene, LaJolla, Calif.) in λ ZAPII (≈2×10$^6$ recombinants) was screened using traditional plaque hybridization with an internal probe, resulting in the isolation of two identical cDNA clones, containing an insert size of 2.4 kb. Upon sequencing, this clone was found to contain the initiating MET aa, Tm1 through Tm7, and 5' and 3' UT sequences, suggesting a full-length clone on a single EcoRI fragment. This cDNA clone contains an open reading frame of 1563 bp and encodes a protein of 520 aa in length, having a relative molecular mass of ≈57,000 daltons. Hydropathy analysis of the protein is consistent with a putative topography of seven transmembrane domains, indicative of the G protein-coupled receptor family.

Sequence analysis revealed that clone α1b/pCEXV was most related to adrenergic receptor since it contained a number of conserved structural features found among the adrenergic receptor family, as described for α1a receptor (see above). This human α1b receptor contains potential sites for N-linked glycosylation in the amino terminus (asparagine residues 10, 24, 29, 34 in FIG. 2A–2H), consistent with the finding that the α1 AR is glycosylated (4,19).

α1c: We screened a human genomic lymphocyte library with probes derived from the third, fifth and sixth transmembrane regions of serotonin 5HT1A under low stringency. Out of several hundred positive clones analyzed by Southern blot analysis, subcloning and sequencing (see Materials and Methods), one phage clone resembled a novel α1 AR. This genomic fragment contained Tm1 through Tm6 of a receptor with high homology to the bovine α1c receptor and thus suggesting the presence of an intron downstream of Tm6, as shown for the α1 receptor family (4,12,20). In order to obtain a full-length clone, several human cDNA libraries were screened by PCR, as described for α1b (also see Materials and Methods). A positive-containing human hippocamppal cDNA library (Stratagene, LaJolla, Calif.) in λ ZAPII (≈2×10$^6$ recombinants) was screened, as described for α1b. A positive clone (hH 20) was identified which contained a 1.7 kb EcoRI cDNA fragment insert. However, this cDNA clone lacked both the amino end of the receptor (the 5' end of the clone terminated at the 5' end of Tm2) and part of the carboxyl tail (the 3' end of the clone corresponded to 40 aa upstream from the "putative" stop codon). Since an alternative genomic subclone which contained the initiating MET codon in addition to Tm1 through Tm6 was available, we needed to obtain the complete 3' carboxyl tail in order to complete the construct of the full-length clone. This was accomplished by using overlapping 45-mer oligonucleotide primers (corresponding to nts. 1142–1212 in FIG. 3), designed within the carboxyl tail of the receptor (at the 3' end of the hH20 cDNA clone), to screen a human lymphocyte genomic library in order to isolate a genomic clone containing the carboxyl tail that includes the termination codon. Two identical positive human lymphocyte genomic clones were isolated from this library. A 0.6 kb PstI fragment was subcloned and shown to contain most of the carboxyl tail (≈20 aa downstream of Tm7) through the termination codon and ≈200 bp of 3' UT sequence.

The complete full-length gene was constructed by splicing together three restriction fragments: A 0.6 kb HincII fragment from the genomic clone, containing ≈0.4 kb of 5' UT sequence and the initiating MET codon through Tm2; the 0.8 kb HincII-PstI fragment from the hH cDNA clone, which contains Tm2 through part of the carboxyl tail, overlapping with the 5' genomic clone by 20 nts. (sharing the unique HincII site at position 196 in FIG. 3); and a 0.6 kb PstI fragment from the second hl genomic clone, which contains the carboxyl tail, the stop codon and ≈0.2 kb of 3' UT sequence, and overlapping with the hH cDNA clone (sharing the unique Pst I site within the carboxyl tail at position 1038 in FIGS. 3A–3G).

The resulting genomic/cDNA/genomic construct contains an open reading frame of 1401 bp and encoding a protein of 466 aa in length, having a molecular weight of ≈51,000 daltons. Hydropathy analysis of the protein is consistent with a putative topography of seven transmembrane domains, as indicated for the previously described human α1a and α1b receptors and indicative of the G protein-coupled receptor family. Sequence analysis revealed that clone α1c/EXJ was most related to adrenergic receptor because it contained the structural features commonly found among the adrenergic receptor family of receptors, as described for the α1a receptor above. Other features of this human $\alpha_{1a}$ receptor gene is the presence of three potential sites for N-linked glycosylation in the amino terminus, at the same position described for the bovine α1c receptor (asparagine residues 7, 13 and 22 in FIG. 3A–3G) (20). Several threonines and serines exist in the second and third cytoplasmic loops of this α1c receptor, which may serve as potential sites for protein kinases and phosphorylation.

TABLE 1

Competition of adrenergic agonists and antagonits for the binding of [³H]prazosin to membranes prepared from LM(tk⁻) cells expressing the human α1a, α1b, and α1c-adrenergic receptor cDNA. Membrane preparations from stabily transfecetd cell lines increasing concentrations of various agonists or antagonists as described under "Materials and Methods". Data is shown as the mean ± S.E.M. of the binding parameters estimated by a computerized non-linear regression analysis obtained in three independent experiments each performed in triplicate.

| | pKi | | |
|---|---|---|---|
| | α1a | α1b | α1c |
| AGONISTS | | | |
| Norepinephrine | 6.633 ± 0.12 | 5.614 ± 0.09 | 5.747 ± 0.18 |
| Epinephrine | 6.245 ± 0.10 | 5.297 ± 0.15 | 5.511 ± 0.13 |
| Oxymetazoline | 5.903 ± 0.16 | 5.919 ± 0.07 | 7.691 ± 0.10 |
| Naphazoline | 6.647 ± 0.18 | 6.155 ± 0.04 | 6.705 ± 0.22 |
| Xylometazoline | 5.913 ± 0.20 | 6.096 ± 0.30 | 7.499 ± 0.19 |
| ANTAGONISTS | | | |
| Prazosin | 9.479 ± 0.19 | 9.260 ± 0.23 | 9.234 ± 0.13 |
| WB-4101 | 8.828 ± 0.12 | 7.909 ± 0.13 | 9.080 ± 0.09 |
| (+) Niguldipine | 6.643 ± 0.10 | 6.937 ± 0.12 | 8.693 ± 0.18 |
| Indoramin | 6.629 ± 0.09 | 7.347 ± 0.17 | 8.341 ± 0.25 |
| 5-Methyl Urapidil | 7.795 ± 0.15 | 6.603 ± 0.09 | 8.160 ± 0.11 |
| HEAT | 7.857 ± 0.13 | 8.474 ± 0.10 | 8.617 ± 0.10 |
| Urapidil | 6.509 ± 0.18 | 5.932 ± 0.11 | 6.987 ± 0.14 |
| Rauwolscine | 5.274 ± 0.12 | 4.852 ± 0.08 | 4.527 ± 0.11 |

Pharmacological Analysis: To further assess the functional identity of the cloned cDNA the coding regions were subcloned into the pCEXV-3 expression vector, and LM(tk⁻) cell lines stably expressing the human cDNA encoding each of the three α1-ARs were established. Membrane preparations of these cell lines showed high affinity binding of [³H]prazosin, with Kd values of 0.21±0.03 nM (Bmax= 0.72±0.04 pmol/mg prot), 0.88±0.1 nM (Bmax=4.59±0.21 pmol/mg prot) and 0.39±0.08 nM (Bmax=1.9±0.04 pmol/ mg prot) for the cells expressing the α1a, α1b, and ═1c-ARs respectively. In contrast in competition binding experiments rauwolscine showed extremely low affinity at the three cloned receptors (Table 1), consistent with their identity as α1-AR. The α-adrenergic agonists NE and epinephrine were found to be 6 and 5-fold respectively, more potent at the human α1a-AR, conversely the imidazoline derivatives such as oxymetazoline and xylometazoline showed 52-fold higher potency at the α1c-AR. Similarly, several antagonists showed marked differences in their potency to inhibit [³H]prazosin binding from the cloned human α1 receptors subtypes. The selective antagonists WB-4101 and 5-methyl-urapidil showed high affinity for the human α1c subtype (0.8 and 7 nM respectively), followed by less than 2-fold lower potency at the human α1a and at least an order of magnitude (15 and 36-fold respectively) lower potency at the human α1b-AR. Similarly, indoramin was 50 and 10-fold more potent at the α1c than at the α1a and α1b respectively. The calcium channel blocker (+)-niguldipine showed the highest selectivity for the three α1-AR subtypes, displacing [³H]prazosin 112 and 57-fold more potently from the α1c than from α1a and α1b transfected cells respectively.

TABLE 2

Receptor-mediated formation of [³H]IP in cell lines transfected with the human α1-adrenergic receptors cDNA. Cell lines stably expressing the human α1-adrenergic receptors were obtained and the IP formation was measured in the absence or presence of 10 μM norepinephrine (NE) in the presence of 10 mM LiCl as described under "Material and Methods". Data are shown as mean ± S.E.M. of three independent experiments performed in triplicate.

| Cell Line | [3H]IP dpm/dish | Fold Stimulation | Receptor * Density pmol/mg Prot |
|---|---|---|---|
| 293 α1a | | | 3.30 |
| Control | 288 ± 29 | | |
| NE | 3646 ± 144 | 13 | |
| CHO α1b | | | 0.49 |
| Control | 1069 ± 26 | | |
| NE | 5934 ± 309 | 6 | |
| NIH3T3 α1c | | | 0.24 |
| Control | 722 ± 61 | | |
| NE | 13929 ± 1226 | 19 | |

*Determined by [³H]Prazosin binding.

The formation of [3H]IP was measured in 293, CHO, and NIH3T3 cell stably expressing the cloned human α1a, α1b, α1c-ARs respectively, to assess the functional coupling of these receptors with the activation of phosphatidyl-inositol specific phospholipase C (PI-PLC). As shown in Table 2, the adrenergic agonist NE (10 μM) activated the formation of IP by 13-fold in cells expressing the α1a receptor, and by 5 and 15-fold in cells expressing the α1b and α1c receptors respectively. Furthermore, when cells expressing α1a, α1b, and α1c receptors were incubated in the presence of 10 μM NE, a rapid increase of cytosolic calcium was observed. The response was characterized by an early peak, followed by a plateau that slowly declined towards resting calcium levels (FIG. 7). The concentration of $[Ca^{2+}]_i$, was increased by 172±33 (n=6), 170±48 (n=6) and 224±79 nM (n=6) in cell lines transfected with the α1a, α1b and α1c receptors respectively. The changes in $[Ca^{2+}]_i$ induced by NE were suppressed by preincubation of the cells with 10 nM prazosin, indicating that the calcium response was mediated by α1-ARs.

We have cloned DNA representing three α1-ARs subtypes (α1a, α1b, α1c) from human brain cDNA and genomic DNA. Of all known G protein-coupled receptor sequences (EMBL/Genbank Data Base), the greatest homology was found between α1a/EXJ and the rat α1a AR (12), rat α1d AR (16) and a previously reported putative human "α1a" adrenergic receptor (H318/3)(2). Comparison of the human α1a deduced aa sequence with known α1a ARs indicates the greatest concentration of identical aa to be in the transmembrane domains. In these Tm regions, the percentage of identity for the human α1a AR is 98% compared to rat α1a AR (12) (this is approximately the same for rat α1d since rat α1d AR is the same as rat α1a AR, except for two amino acid differences), 100% with the previously reported H318/3, 78% with the human α1b receptor (see below), and 69% with the human α1c receptor (see below), which is typical among subtypes. When considering the full-length proteins, the percent identity drops and is only 50% for the human α1b and 49% for the human α1c receptor. Both the alignment (see FIG. 4) and percent identity of this human α1a sequence, relative to other members of the AR family strongly suggest that this is a new receptor and is the human species homolog of the rat α1a receptor.

FIG. 4 shows a comparison between the deduced aa sequence of α1a/EXJ and the sequences of rat α1a and HAR. An overall homology of 83.5% aa identity with rat α1a and 86.5% aa identity with the previously published H318/3 clone was observed, suggesting that our human α1a receptor is not any more related to the previously published putative human "α1a" than it is to the rat α1a receptor. In fact, in support of this conclusion, is the fact that the overall aa homology of rat α1a receptor with our human α1a receptor is 83.5% but is only 72% compared to the H318/3 receptor. The main differences between our human α1a receptor and the previously reported "α1a" receptor in relation to the rat α1a are indicated in FIG. 4. Most notably are the differences observed at both the amino and carboxyl ends of the receptor. Specifically, both our human α1a and rat α1a use the starting MET aa at position 1 (see FIG. 4) whereas the previously published H318/3 uses the starting MET 48 aa downstream. Also, the amino terminus of the H318/3 clone is completely divergent from either rat α1a or our human α1a receptor until about 12 aa upstream of Tm1 where significant homology begins. Similarly, in the carboxyl tail, the homology of H318/3 diverges ≈90 aa upstream from the stop codon of either rat or our human α1a receptor and instead, uses a stop codon 30 aa upstream from the stop codon on either of these receptors. Finally, the H318/3 clone has an amino terminal extracellular region that does not contain potential sites for N-linked glycosylation (2), in contrast to the rat α1a or our human α1a receptor, which contains two potential sites (12, see also FIG. 1 and above). Thus, these data strongly suggest that our human α1a receptor is different in sequence from the previously reported putative human "α1a" (H318/3) but is more related to the previously published rat α1a receptor. Interestingly, the rat α1a aa sequence diverges from both human α1a receptors for ≈65 aa in the carboxyl tail (position 434–508 in FIG. 1); however, homology is seen again in our human α1a receptor but not with H318/3, downstream from this region.

The cloning of different α1 receptor subtypes permits analysis of both the pharmacological and functional properties of adrenergic receptors. The human α1a/pCEXV clone exhibited the greatest homology with the rat and hamster α1b receptors, out of all known G protein-coupled receptor clones (EMBL/Genbank Data Bank). Comparison of the human α1b deduced aa sequence with known α1ARs indicates the greatest homology in the transmembrane regions. In these Tm regions, the percent identity for the human α1b AR is 99% compared to either rat (25) or hamster (4) α1b receptor, 78% with human α1a receptor and 75% with human α1c receptor, which is typical among subtypes. When analyzing the full-length proteins, the percent identity slightly drops and is 94.5% compared to rat α1b, 95.5% compared to hamster α1b receptor, 50% compared to human α1a and 51% compared to human α1c receptor. Both the alignment (see FIG. 5) and percent identity of this human α1b sequence, relative to other members of the AR family, strongly suggest that this clone represents a new receptor and is the human species homologue of the rat/hamster α1b receptor. FIG. 5 shows a comparison between the deduced amino acid sequence of α1b/pcEXV and the aa sequence of rat α1b and hamster α1b receptors.

A third human adrenergic receptor clone, α1c/EXJ, showed the greatest homology with the bovine α1c AR gene (20), from all known G protein-coupled receptor sequences (EMBL/Genbank Data Bank). Comparison of the human α1c deduced aa sequence with the α1 ARs indicates the greatest homology to be in the transmembrane regions. In these Tm regions, the percent identity for the human α1c AR is 97% compared to the bovine α1c AR (20), 75% with human α1b receptor and 69% with human α1a receptor, which is typical among subtypes. When one examines the full-length proteins, the percent identity drops and is only 51% compared to either the human α1b or human α1a receptor. FIG. 6 shows a comparison between the deduced amino acid sequence of α1c/EXJ and the aa sequence of bovine α1c. An overall homology of 92% aa identity with bovine α1c receptor was observed. Both the alignment (see FIG. 6) and percent identity of this human α1c sequence, relative to other members of the AR family, strongly suggest that this clone represents a new receptor and is the human species homologue of the bovine α1a receptor.

The stable expression of the three cloned human α1 receptors enabled the characterization of their pharmacological as well as their functional properties and allowed identification of certain unique features of the human receptors, not predicted from previous data.

The rank-order of potency of known α-adrenergic agonists and antagonists to compete with [$^3$H]prazosin in binding assays, confirmed that the cloned cDNAs encode three human receptors of the α1-AR family. Moreover, the potencies of selective antagonists such as WB-4101 and 5-methyl-urapidil at the three human α1-receptors were found to be in close agreement with the potencies of these antagonists at the cloned rat α1a, hamster α1b, and bovine α1c (4,12,20). These results suggest that the sequence homology between the three mammalian receptors resulted in a conservation of their pharmacological properties across different species. In the past the pharmacological characterization of α1-adrenergic receptors took advantage of the existence of selective antagonists such as WB-4101 and 5-methyl-urapidil that bind with high affinity to a subset of α1-receptors classified as α1A (9,15). Our results using these selective antagonists indicate that these antagonists bind with similar affinity to both human α1a and α1c-receptors, and that they can only discriminate between either of these two subtypes and the α1b receptor. The calcium channel blocker (+)-niguldipine was found to bind with high affinity to a subset of α1-receptors also labeled by [$^3$H]5-methyl-urapidil in rat brain, thus defining this antagonist as α1A selective (8). The high affinity of the human α1c receptor for (+)-niguldipine and the fact that it binds to the human α1a and α1b subtypes, with at least an order of magnitude lower affinity, strongly supports the notion that the human α1c gene encodes the pharmacological α1A-receptor subtype. The possibility that this also holds true in the rat, is suggested by the fact that the potency of (+)niguldipine for the rat α1a clone is also at least an order of magnitude lower than that found for this antagonist in rat tissues. Moreover, in spite of the earlier reports on the absence of the bovine α1c cognate in rat tissues (20,21) pharmacological evidence suggest that this species express an α1 receptor similar to the cloned α1a receptor. These data altogether indicate that in trying to match the pharmacological subclassification of the α1-ARs with the evidence from molecular cloning studies, the initial assignment of the cloned rat α1a receptor with the α1A receptor subtype was inadequate. Recently, a rat cDNA clone 99.8% homologous to the rat α1a-receptor, was described as a novel α1d subtype (16); however, this incorrect classification was due to the poor correlation between the affinities of α1A-selective antagonists in tissue preparations versus the cloned rat α1a receptor.

The three human α1 receptor subtypes were able to induce the formation of IP, consistent with the known functional coupling of α1-ARs, through a GTP-dependent protein to the activation of PI-PLC. In addition we demonstrated that upon receptor activation by adrenergic agonists, the three human $\alpha_1$ receptor subtypes induced transient changes in $[Ca^{2+}]_i$. Consistent with the mobilization of calcium from intracellular stores by inositol-1,3,5 triphosphate, released by the receptor-mediated activation of PI-PLC.

We have cloned and expressed three human cDNA that encode functional α1-ARs. This three transcripts display significant pharmacologic as well as molecular features to constitute distinct α1-AR subtypes. In sharp contrast with the restricted expression of the rat and bovine transcripts, our findings indicate that species homologs of the three α1-ARs are expressed in human tissues. These findings together with recent reports on the dissimilar tissue distribution of the α1b and α1c receptor cognates between animal species such as rat and rabbit (21), commonly used in the development of novel α1-adrenergic agents, emphasize the need to study the pharmacological properties of the human α1-receptors. In this regard, the results from this study on the selectivity of clinically effective antihypertensives such as indoramin, as well as vasoconstrictors such as oxymetazoline and xylometazoline for the human α1c-AR, suggest a potential role for this α1-receptor subtype in the physiological control of vascular tone in the human. Thus, the availability of cell lines expressing each of the human α1-receptor subtypes constitute a unique tool in the design of subtype specific agonists and antagonists, that can be targeted to selective therapeutic applications. Of specific interest for therapeutics are subtype selective alpha-1 antagonists for the treatment of Benign Prostatic Hypertrophy and subtype selective alpha-1 agonists for the treatment of nasal congestion. In each case, a more selective drug is expected to reduce the side effects which presently limit this avenue of therapy. The development of subtype selective alpha-1 agonists may also lead to more effective treatment of urinary incontinence.

REFERENCES

Borden, L. A., Maxfield, F. R., Goldman, J. E., and Shelanski, M. L., *Neurobiol. Aging.*, 13, 33–38, 1991.

Bruno, J. F., J. Whittaker, J. Song, and M. Berelowitz. *Biochem. Biophys. Res. Comm.* 179, 1485–1490 (1991).

Bush, A. W., Borden, L. A., Greene, L. A., and Maxfield, F. R., *J. Neurochem.* 57, 562–574, 1991.

Cotecchia, S., Schwinn, D. A., Randall, R. R., Lefkowitz, R. J., Caron, M. G., and Kobilka, B. K., *Proc. Natl. Acad. Sci. USA*, 85, 7159–7163, 1988.

Feinberg, A. P., and B. Vogelstein. *Anal. Biochem.* 132, 6–13 (1983).

Flavahan, N. A. and Vanhoutte, P. M., In: *The Alpha-1 Adrenergic Receptors*, (ed. by R. R. Ruffolo, Jr., Humana Press, Clifton N.J.) pp. 351–403, 1987.

Forray, C., and El-Fakahany, E. E., *Mol. Pharmacol.*, 37, 893–902, 1990.

Graziadei, I., Zernig, G., Boer, R., and Glossman, H., *Eur. J. Pharmacol.* 172, 329–337, 1989.

Gross, G., Hanft, G., and Rugevics, C., *Eur. J. Pharmacol.*, 151, 333–335, 1989.

Hieble, J. P., Sarau, H. M., Foley, J-J., DeMarinis, R. M., and Pendleton, P. G., *Naunyn-Schmiedeberg's Arch. Pharmacol.*, 318, 267–273, 1982.

Langer, S. Z., *Pharmacol. Rev.*, 32, 377–360, 1980.

Lomasney, J. W., Cotecchia, S., Lorenz, W., Leung, W.-Y., Schwinn, D. A., Yang-Feng, T. L., Brownstein, M., Lefkowitz, R. J., and Caron, M., *J. Biol. Chem.*, 266, 6365–6369, 1991.

Miller, J. and R. N. Germain. *J. Exp. Med.* 164, 1478–1489 (1986).

Minneman, K. P., *Pharmacol. Rev.*, 40, 87–119, 1988.

Morrow, A. L., and Creese, I., *Mol. Pharmacol.*, 29, 321–330, 1986.

Perez, D. M., M. T. Piascik, and R. M. Graham. *Mol. Pharmacol.* 40, 876–883 (1991).

Sambrook, J., Fritsch, E. F., and Maniatis, T., In: *Molecular Cloning: A Laboratory Manual*, 2nd Edition (Cold Spring Harbor Lab., Cold Spring Harbor, N.Y.), 1989.

Sanger, S. *Proc. Natl. Acad. Sci. USA* 74, 5463–5467 (1977).

Sawutz, D. G., S. M. Lanier, C. D. Warren, and R. M. Graham. *Mol. Pharmacol.* 32, 565–571 (1987).

Schwinn, D. A., Lomasney, J. W., Lorenz, W., Szklut, P. J., Fremeau, R. T., Yang-Feng, T. L., Caron, M. G., Lefkowitz, R. J. and Cotecchia, S., *J. Biol. Chem.*, 265, 8183–8189, 1990.

Schwinn, D. A., Page, S. A., Middleton, J. P., Lorenz, W., Liggett, S. B., Yamamoto, E., Lapetina, E. G., Caron, M. G., Lefkowitz, R. J., and Cotecchia, S., *Mol. Pharmacol.*, 40, 619–626, 1991.

Southern, E. M. *J. Mol. Biol.* 98,503–505 (1975). Starke, S., *Rev. Physiol. Biochem. Pharmacol.*, 88, 199–236, 1981.

Timmermans, P. B. M. W. M., Karamat Ali, F., Kwa, H. Y., Schoop, A. M. C., Slothorst-Grisdijk, F. P., and van Zwieten, P. A., *Mol. Pharmacol.*, 20, 295–301, 1981.

Timmermans, P. B. M. W. M., and Thoolen. M. J. M. C., In: *The Alpha-1 Adrenergic Receptors*, (ed. by R. R. Ruffolo, Jr., Humana Press, Clifton N.J.) pp. 113–187, 1987.

Voigt, M. M., J. Kispert, and H. Chin. *Nucleic Acid Res.* 18, 1053 (1990).

Weinshank, R. L., Zgombick, J. M., Macchi, M., Adham, N., Lichtblau, H., Branchek, T. A., and Hartig, P. R., *Mol. Pharmacol.*, 38, 681–688, 1990.

What is claimed:

1. An isolated nucleic acid molecule encoding a human α$_{1c}$ adrenergic receptor.

2. An isolated nucleic acid molecule of claim 1, wherein the nucleic acid molecule is a DNA molecule.

3. A DNA molecule of claim 2 wherein the DNA molecule is cDNA.

4. An isolated nucleic acid molecule of claim 1, wherein the nucleic acid molecule encodes a human α$_{1c}$ adrenergic receptor having an amino acid sequence as shown in FIGS. 3A–3G (Seq. ID No. 6).

5. A vector comprising the nucleic acid molecule of claim 1.

6. A plasmid comprising the vector of claim 5.

7. A vector of claim 5 adapted for expression in a bacterial cell which comprises the regulatory elements necessary for the expression of the nucleic acid in the bacterial cell so located relative to the nucleic acid encoding a human α$_{1c}$ adrenergic receptor as to permit expression thereof.

8. A vector of claim 5 adapted for expression in a yeast cell which comprises the regulatory elements necessary for the expression of the nucleic acid in the yeast cell so located relative to the nucleic acid encoding a human α$_{1c}$ adrenergic receptor as to permit expression thereof.

9. A vector of claim 5 adapted for expression in a mammalian cell which comprises the regulatory elements necessary for the expression of the nucleic acid in the mammalian cell so located relative to the nucleic acid encoding a human α$_{1c}$ adrenergic receptor as to permit expression thereof.

10. A plasmid of claim 6 adapted for expression in a mammalian cell which comprises the regulatory elements necessary for the expression of the nucleic acid in the mammalian cell so located relative to the nucleic acid encoding a human α$_{1c}$ adrenergic receptor as to permit expression thereof.

11. A plasmid designated pcEXV-α$_{1c}$ (ATCC Accession No. 75317).

12. A mammalian cell comprising the plasmid of claim 6.

13. A mammalian cell of claim 12, wherein the mammalian cell is an LM(tk⁻) cell.

14. An LM(tk⁻) cell comprising the plasmid of claim 9.

* * * * *

UNITED STATES PATENT AND TRADEMARK OFFICE
CERTIFICATE OF CORRECTION

PATENT NO. : 5,714,381
DATED : February 3, 1998
INVENTOR(S) : Jonathan A. Bard, et. al.

It is certified that error appears in the above-identified patent and that said Letters Patent is hereby corrected as shown below:

Col.17, line 28: "human adrenergic" should read --human $a_1$ adrenergic--
Col.22, line 32: "in vivo" should read --*in vivo*--
Col.23, line 3: "e1" should read --$a_1$--
Col.25, line 2: "L-a1c" should read --L-$a_{1b}$--
Col.28, line 46: "plutonit" should read --pluronic--
Col.29, line 4: "rat =1a" should read --rat $a_{1a}$--
Col.31, line 21: "$a_{1a}$" should read --$a_{1c}$--
       line 32: "bindinq" should read --binding--
Col.32, line 1: "=1c-" should read --$a_{1c}$---
       line 35: "[3H]IP" should read --[$^3$H]IP--
       line 46: "[3H]IP" should read --[$^3$H]IP--
Col.33, line 63: "a1a" should read --$a_{1b}$--
Col.34, line 36: "a1a" should read --$a_{1c}$--
       line 51: "mammalian receptor"' should read --mammalian $a_1$ receptor--
Col.35, line 10: "a1a" should read --$a_{1c}$--

Signed and Sealed this

Twenty-second Day of September, 1998

Attest:

BRUCE LEHMAN

*Attesting Officer*      *Commissioner of Patents and Trademarks*

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 2140 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: N ( i v ) ANTI-SENSE: N ( i x ) FEATURE:
        ( A ) NAME/KEY: CDS
        ( B ) LOCATION: 178..1893
        ( D ) OTHER INFORMATION:

( x i ) SEQUENCE DESCRIPTION: SEQ ID NO:1:

```
CCGGGCCAGG  CACGTCCGCT  CTCGGACAGC  CGCTCCGCGT  CACAGGAACT  TGGGCAGGAC    60

CCGACGGGAC  CCGTGCGCGG  AGCTGCATCT  GGAGCCCCGC  GGCTATGCCC  TGTGCTCCCC   120

TCCTGCCGGC  CGCTCGTTCT  GTGCCCCCGG  CCCGGCCACC  GACGGCCGCG  CGTTGAG      177
```

| | | | | | | | | | | | | | | | | |
|---|---|---|---|---|---|---|---|---|---|---|---|---|---|---|---|---|
| ATG | ACT | TTC | CGC | GAT | CTC | CTG | AGC | GTC | AGT | TTC | GAG | GGA | CCC | CGC | CCG | 225 |
| Met | Thr | Phe | Arg | Asp | Leu | Leu | Ser | Val | Ser | Phe | Glu | Gly | Pro | Arg | Pro | |
| 1 | | | | 5 | | | | | 10 | | | | | 15 | | |
| GAC | AGC | AGC | GCA | GGG | GGC | TCC | AGC | GCG | GGC | GGC | GGG | GGC | AGC | GCG | | 273 |
| Asp | Ser | Ser | Ala | Gly | Gly | Ser | Ser | Ala | Gly | Gly | Gly | Gly | Ser | Ala | | |
| | | | 20 | | | | | 25 | | | | | 30 | | | |
| GGC | GGC | GCG | GCC | CCC | TCG | GAG | GGC | CCG | GCG | GTG | GGC | GGC | GTG | CCG | GGG | 321 |
| Gly | Gly | Ala | Ala | Pro | Ser | Glu | Gly | Pro | Ala | Val | Gly | Gly | Val | Pro | Gly | |
| | | 35 | | | | | 40 | | | | | 45 | | | | |
| GGC | GCG | GGC | GGC | GGC | GGC | GGC | GTG | GTG | GGC | GCA | GGC | AGC | GGC | GAG | GAC | 369 |
| Gly | Ala | Gly | Gly | Gly | Gly | Gly | Val | Val | Gly | Ala | Gly | Ser | Gly | Glu | Asp | |
| | 50 | | | | | 55 | | | | | 60 | | | | | |
| AAC | CGG | AGC | TCC | GCG | GGG | GAG | CCG | GGG | AGC | GCG | GGC | GCG | GGC | GGC | GAC | 417 |
| Asn | Arg | Ser | Ser | Ala | Gly | Glu | Pro | Gly | Ser | Ala | Gly | Ala | Gly | Gly | Asp | |
| 65 | | | | | 70 | | | | | 75 | | | | | 80 | |
| GTG | AAT | GGC | ACG | GCG | GCC | GTC | GGG | GGA | CTG | GTG | GTG | AGC | GCG | CAG | GGC | 465 |
| Val | Asn | Gly | Thr | Ala | Ala | Val | Gly | Gly | Leu | Val | Val | Ser | Ala | Gln | Gly | |
| | | | 85 | | | | | 90 | | | | | 95 | | | |
| GTG | GGC | GTG | GGC | GTC | TTC | CTG | GCA | GCC | TTC | ATC | CTT | ATG | GCC | GTG | GCA | 513 |
| Val | Gly | Val | Gly | Val | Phe | Leu | Ala | Ala | Phe | Ile | Leu | Met | Ala | Val | Ala | |
| | | | 100 | | | | | 105 | | | | | 110 | | | |
| GGT | AAC | CTG | CTT | GTC | ATC | CTC | TCA | GTG | GCC | TGC | AAC | CGC | CAC | CTG | CAG | 561 |
| Gly | Asn | Leu | Leu | Val | Ile | Leu | Ser | Val | Ala | Cys | Asn | Arg | His | Leu | Gln | |
| | | 115 | | | | | 120 | | | | | 125 | | | | |
| ACC | GTC | ACC | AAC | TAT | TTC | ATC | GTG | AAC | CTG | GCC | GTG | GCC | GAC | CTG | CTG | 609 |
| Thr | Val | Thr | Asn | Tyr | Phe | Ile | Val | Asn | Leu | Ala | Val | Ala | Asp | Leu | Leu | |
| | 130 | | | | | 135 | | | | | 140 | | | | | |
| CTG | AGC | GCC | ACC | GTA | CTG | CCC | TTC | TCG | GCC | ACC | ATG | GAG | GTT | CTG | GGC | 657 |
| Leu | Ser | Ala | Thr | Val | Leu | Pro | Phe | Ser | Ala | Thr | Met | Glu | Val | Leu | Gly | |
| 145 | | | | | 150 | | | | | 155 | | | | | 160 | |
| TTC | TGG | GCC | TTT | GGC | CGC | GCC | TTC | TGC | GAC | GTA | TGG | GCC | GCC | GTG | GAC | 705 |
| Phe | Trp | Ala | Phe | Gly | Arg | Ala | Phe | Cys | Asp | Val | Trp | Ala | Ala | Val | Asp | |
| | | | 165 | | | | | 170 | | | | | 175 | | | |
| GTG | CTG | TGC | TGC | ACG | GCC | TCC | ATC | CTC | AGC | CTC | TGC | ACC | ATC | TCC | GTG | 753 |

-continued

```
                Val Leu Cys Cys Thr Ala Ser Ile Leu Ser Leu Cys Thr Ile Ser Val
                        180                 185                 190

GAC CGG TAC GTG GGC GTG CGC CAC TCA CTC AAG TAC CCA GCC ATC ATG              801
Asp Arg Tyr Val Gly Val Arg His Ser Leu Lys Tyr Pro Ala Ile Met
        195                 200                 205

ACC GAG CGC AAG GCG GCC GCC ATC CTG GCC CTG CTC TGG GTC GTA GCC              849
Thr Glu Arg Lys Ala Ala Ala Ile Leu Ala Leu Leu Trp Val Val Ala
    210                 215                 220

CTG GTG GTG TCC GTA GGG CCC CTG CTG GGC TGG AAG GAG CCC GTG CCC              897
Leu Val Val Ser Val Gly Pro Leu Leu Gly Trp Lys Glu Pro Val Pro
225                 230                 235                 240

CCT GAC GAG CGC TTC TGC GGT ATC ACC GAG GAG GCG GGC TAC GCT GTC              945
Pro Asp Glu Arg Phe Cys Gly Ile Thr Glu Glu Ala Gly Tyr Ala Val
                245                 250                 255

TTC TCC TCC GTG TGC TCC TTC TAC CTG CCC ATG GCG GTC ATC GTG GTC              993
Phe Ser Ser Val Cys Ser Phe Tyr Leu Pro Met Ala Val Ile Val Val
            260                 265                 270

ATG TAC TGC CGC GTG TAC GTG GTC GCG CGC AGC ACC ACG CGC AGC CTC             1041
Met Tyr Cys Arg Val Tyr Val Val Ala Arg Ser Thr Thr Arg Ser Leu
        275                 280                 285

GAG GCA GGC GTC AAG CGC GAG CGA GGC AAG GCC TCC GAG GTG GTG CTG             1089
Glu Ala Gly Val Lys Arg Glu Arg Gly Lys Ala Ser Glu Val Val Leu
    290                 295                 300

CGC ATC CAC TGT CGC GGC GCG GCC ACG GGC GCC GAC GGG GCG CAC GGC             1137
Arg Ile His Cys Arg Gly Ala Ala Thr Gly Ala Asp Gly Ala His Gly
305                 310                 315                 320

ATG CGC AGC GCC AAG GGC CAC ACC TTC CGC AGC TCG CTC TCC GTG CGC             1185
Met Arg Ser Ala Lys Gly His Thr Phe Arg Ser Ser Leu Ser Val Arg
                325                 330                 335

CTG CTC AAG TTC TCC CGT GAG AAG AAA GCG GCC AAG ACT CTG GCC ATC             1233
Leu Leu Lys Phe Ser Arg Glu Lys Lys Ala Ala Lys Thr Leu Ala Ile
            340                 345                 350

GTC GTG GGT GTC TTC GTG CTC TGC TGG TTC CCT TTC TTT GTC CTG             1281
Val Val Gly Val Phe Val Leu Cys Trp Phe Pro Phe Phe Phe Val Leu
        355                 360                 365

CCG CTC GGC TCC TTG TTC CCG CAG CTG AAG CCA TCG GAG GGC GTC TTC             1329
Pro Leu Gly Ser Leu Phe Pro Gln Leu Lys Pro Ser Glu Gly Val Phe
    370                 375                 380

AAG GTC ATC TTC TGG CTC GGC TAC TTC AAC AGC TGC GTG AAC CCG CTC             1377
Lys Val Ile Phe Trp Leu Gly Tyr Phe Asn Ser Cys Val Asn Pro Leu
385                 390                 395                 400

ATC TAC CCC TGT TCC AGC CGC GAG TTC AAG CGC GCC TTC CTC CGT CTC             1425
Ile Tyr Pro Cys Ser Ser Arg Glu Phe Lys Arg Ala Phe Leu Arg Leu
                405                 410                 415

CTG CGC TGC CAG TGC CGT CGT CGC GGG CGC CGC CGC CCT CTC TGG CGT             1473
Leu Arg Cys Gln Cys Arg Arg Arg Arg Arg Arg Pro Leu Trp Arg
            420                 425                 430

GTC TAC GGC CAC CAC TGG CGG GCC TCC ACC AGC GGC CTG CGC CAG GAC             1521
Val Tyr Gly His His Trp Arg Ala Ser Thr Ser Gly Leu Arg Gln Asp
        435                 440                 445

TGC GCC CCG AGT TCG GGC GAC GCG CCC CCG GGA GCG CCG CTG GCC CTC             1569
Cys Ala Pro Ser Ser Gly Asp Ala Pro Pro Gly Ala Pro Leu Ala Leu
    450                 455                 460

ACC GCG CTC CCC GAC CCC GAC CCC GAA CCC CCA GGC ACG CCC GAG ATG             1617
Thr Ala Leu Pro Asp Pro Asp Pro Glu Pro Pro Gly Thr Pro Glu Met
465                 470                 475                 480

CAG GCT CCG GTC GCC AGC CGT CGA AAG CCA CCC AGC GCC TTC CGC GAG             1665
Gln Ala Pro Val Ala Ser Arg Arg Lys Pro Pro Ser Ala Phe Arg Glu
                485                 490                 495

TGG AGG CTG CTG GGG CCG TTC CGG AGA CCC ACG ACC CAG CTG CGC GCC             1713
```

-continued

| | | | | | | | | | | | | | | |
|---|---|---|---|---|---|---|---|---|---|---|---|---|---|---|
|Trp|Arg|Leu|Leu<br>500|Gly|Pro|Phe|Arg|Arg<br>505|Pro|Thr|Thr|Gln|Leu<br>510|Arg|Ala|

| | | | | | | | | | | | | | | | |
|---|---|---|---|---|---|---|---|---|---|---|---|---|---|---|---|
|AAA|GTC|TCC|AGC|CTG|TCG|CAC|AAG|ATC|CGC|GCC|GGG|GGC|GCG|CAG|CGC|
|Lys|Val|Ser<br>515|Ser|Leu|Ser|His|Lys<br>520|Ile|Arg|Ala|Gly|Gly<br>525|Ala|Gln|Arg|

1761

| | | | | | | | | | | | | | | | |
|---|---|---|---|---|---|---|---|---|---|---|---|---|---|---|---|
|GCA|GAG|GCA|GCG|TGC|GCC|CAG|CGC|TCA|GAG|GTG|GAG|GCT|GTG|TCC|CTA|
|Ala|Glu<br>530|Ala|Ala|Cys|Ala|Gln|Arg<br>535|Ser|Glu|Val|Glu<br>540|Ala|Val|Ser|Leu|

1809

| | | | | | | | | | | | | | | | |
|---|---|---|---|---|---|---|---|---|---|---|---|---|---|---|---|
|GGC|GTC|CCA|CAC|GAG|GTG|GCC|GAG|GGC|GCC|ACC|TGC|CAG|GCC|TAC|GAA|
|Gly<br>545|Val|Pro|His|Glu|Val<br>550|Ala|Glu|Gly|Ala|Thr<br>555|Cys|Gln|Ala|Tyr|Glu<br>560|

1857

| | | | | | | | | | | |
|---|---|---|---|---|---|---|---|---|---|---|
|TTG|GCC|GAC|TAC|AGC|AAC|CTA|CGG|GAG|ACC|GAT ATT TAAGGACCCC|
|Leu|Ala|Asp|Tyr|Ser<br>565|Asn|Leu|Arg|Glu|Thr<br>570|Asp Ile|

1903

AGAGCTAGGC CGCGGAGTGT GCTGGGCTTG GGGGTAAGGG GGACCAGAGA GGCGGGCTGG 1963

TGTTCTAAGA GCCCCGTGC AAATCGGAGA CCCGGAAACT GATCAGGGCA GCTGCTCTGT 2023

GACATCCCTG AGGAACTGGG CAGAGCTTGA GGCTGGAGCC CTTGAAAGGT GAAAAGTAGT 2083

GGGGCCCCCT GCTGGACTCA GGTGCCCAGA ACTCTTTTCT TAGAAGGGAG AGGCTGC 2140

( 2 ) INFORMATION FOR SEQ ID NO:2:

( i ) SEQUENCE CHARACTERISTICS:
        ( A ) LENGTH: 572 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
|Met<br>1|Thr|Phe|Arg|Asp<br>5|Leu|Leu|Ser|Val|Ser<br>10|Phe|Glu|Gly|Pro|Arg<br>15|Pro|

| | | | | | | | | | | | | | | |
|---|---|---|---|---|---|---|---|---|---|---|---|---|---|---|
|Asp|Ser|Ser|Ala<br>20|Gly|Gly|Ser|Ser|Ala<br>25|Gly|Gly|Gly|Gly|Gly<br>30|Ser|Ala|

| | | | | | | | | | | | | | | |
|---|---|---|---|---|---|---|---|---|---|---|---|---|---|---|
|Gly|Gly|Ala|Ala<br>35|Pro|Ser|Glu|Gly|Pro<br>40|Ala|Val|Gly|Gly<br>45|Val|Pro|Gly|

| | | | | | | | | | | | | | | |
|---|---|---|---|---|---|---|---|---|---|---|---|---|---|---|
|Gly|Ala<br>50|Gly|Gly|Gly|Gly|Gly<br>55|Val|Val|Gly|Ala|Gly<br>60|Ser|Gly|Glu|Asp|

| | | | | | | | | | | | | | | |
|---|---|---|---|---|---|---|---|---|---|---|---|---|---|---|
|Asn<br>65|Arg|Ser|Ser|Ala|Gly<br>70|Glu|Pro|Gly|Ser|Ala<br>75|Gly|Ala|Gly|Gly|Asp<br>80|

| | | | | | | | | | | | | | | |
|---|---|---|---|---|---|---|---|---|---|---|---|---|---|---|
|Val|Asn|Gly|Thr|Ala<br>85|Ala|Val|Gly|Gly|Leu<br>90|Val|Val|Ser|Ala|Gln<br>95|Gly|

| | | | | | | | | | | | | | | |
|---|---|---|---|---|---|---|---|---|---|---|---|---|---|---|
|Val|Gly|Val|Gly<br>100|Val|Phe|Leu|Ala|Ala<br>105|Phe|Ile|Leu|Met<br>110|Ala|Val|Ala|

| | | | | | | | | | | | | | | |
|---|---|---|---|---|---|---|---|---|---|---|---|---|---|---|
|Gly|Asn|Leu|Leu<br>115|Val|Ile|Leu|Ser<br>120|Val|Ala|Cys|Asn|Arg<br>125|His|Leu|Gln|

| | | | | | | | | | | | | | | |
|---|---|---|---|---|---|---|---|---|---|---|---|---|---|---|
|Thr|Val|Thr|Asn<br>130|Tyr|Phe|Ile<br>135|Val|Asn|Leu|Ala|Val<br>140|Ala|Asp|Leu|Leu|

| | | | | | | | | | | | | | | |
|---|---|---|---|---|---|---|---|---|---|---|---|---|---|---|
|Leu|Ser<br>145|Ala|Thr|Val|Leu<br>150|Pro|Phe|Ser|Ala|Thr<br>155|Met|Glu|Val|Leu|Gly<br>160|

| | | | | | | | | | | | | | | |
|---|---|---|---|---|---|---|---|---|---|---|---|---|---|---|
|Phe|Trp|Ala|Phe|Gly<br>165|Arg|Ala|Phe|Cys|Asp<br>170|Val|Trp|Ala|Ala|Val<br>175|Asp|

| | | | | | | | | | | | | | | |
|---|---|---|---|---|---|---|---|---|---|---|---|---|---|---|
|Val|Leu|Cys|Cys<br>180|Thr|Ala|Ser|Ile|Leu<br>185|Ser|Leu|Cys|Thr|Ile<br>190|Ser|Val|

| | | | | | | | | | | | | | | |
|---|---|---|---|---|---|---|---|---|---|---|---|---|---|---|
|Asp|Arg|Tyr|Val<br>195|Gly|Val|Arg|His<br>200|Ser|Leu|Lys|Tyr|Pro<br>205|Ala|Ile|Met|

| | | | | | | | | | | | | | | |
|---|---|---|---|---|---|---|---|---|---|---|---|---|---|---|
|Thr|Glu<br>210|Arg|Lys|Ala|Ala|Ala<br>215|Ile|Leu|Ala|Leu|Leu<br>220|Trp|Val|Val|Ala|

| Leu 225 | Val | Val | Ser | Val | Gly 230 | Pro | Leu | Leu | Gly | Trp 235 | Lys | Glu | Pro | Val | Pro 240 |
|---|---|---|---|---|---|---|---|---|---|---|---|---|---|---|---|
| Pro | Asp | Glu | Arg | Phe 245 | Cys | Gly | Ile | Thr | Glu 250 | Glu | Ala | Gly | Tyr | Ala 255 | Val |
| Phe | Ser | Ser | Val 260 | Cys | Ser | Phe | Tyr | Leu 265 | Pro | Met | Ala | Val | Ile 270 | Val | Val |
| Met | Tyr | Cys 275 | Arg | Val | Tyr | Val | Val 280 | Ala | Arg | Ser | Thr | Thr 285 | Arg | Ser | Leu |
| Glu | Ala 290 | Gly | Val | Lys | Arg | Glu 295 | Arg | Gly | Lys | Ala | Ser 300 | Glu | Val | Val | Leu |
| Arg 305 | Ile | His | Cys | Arg | Gly 310 | Ala | Ala | Thr | Gly | Ala 315 | Asp | Gly | Ala | His | Gly 320 |
| Met | Arg | Ser | Ala | Lys 325 | Gly | His | Thr | Phe | Arg 330 | Ser | Ser | Leu | Ser | Val 335 | Arg |
| Leu | Leu | Lys | Phe 340 | Ser | Arg | Glu | Lys | Lys 345 | Ala | Ala | Lys | Thr | Leu 350 | Ala | Ile |
| Val | Val | Gly 355 | Val | Phe | Val | Leu | Cys 360 | Trp | Phe | Pro | Phe | Phe 365 | Phe | Val | Leu |
| Pro | Leu 370 | Gly | Ser | Leu | Phe | Pro 375 | Gln | Leu | Lys | Pro | Ser 380 | Glu | Gly | Val | Phe |
| Lys 385 | Val | Ile | Phe | Trp | Leu 390 | Gly | Tyr | Phe | Asn | Ser 395 | Cys | Val | Asn | Pro | Leu 400 |
| Ile | Tyr | Pro | Cys | Ser 405 | Ser | Arg | Glu | Phe | Lys 410 | Arg | Ala | Phe | Leu | Arg 415 | Leu |
| Leu | Arg | Cys | Gln 420 | Cys | Arg | Arg | Arg | Arg 425 | Arg | Arg | Arg | Pro | Leu 430 | Trp | Arg |
| Val | Tyr | Gly 435 | His | His | Trp | Arg | Ala 440 | Ser | Thr | Ser | Gly | Leu 445 | Arg | Gln | Asp |
| Cys | Ala 450 | Pro | Ser | Ser | Gly | Asp 455 | Ala | Pro | Gly | Ala | Pro 460 | Leu | Ala | Leu |
| Thr 465 | Ala | Leu | Pro | Asp | Pro 470 | Asp | Pro | Glu | Pro | Pro 475 | Gly | Thr | Pro | Glu | Met 480 |
| Gln | Ala | Pro | Val | Ala 485 | Ser | Arg | Arg | Lys | Pro 490 | Pro | Ser | Ala | Phe | Arg 495 | Glu |
| Trp | Arg | Leu | Leu | Gly 500 | Pro | Phe | Arg | Arg 505 | Pro | Thr | Thr | Gln | Leu 510 | Arg | Ala |
| Lys | Val | Ser | Ser 515 | Leu | Ser | His | Lys 520 | Ile | Arg | Ala | Gly | Gly 525 | Ala | Gln | Arg |
| Ala | Glu 530 | Ala | Ala | Cys | Ala | Gln 535 | Arg | Ser | Glu | Val | Glu 540 | Ala | Val | Ser | Leu |
| Gly 545 | Val | Pro | His | Glu | Val 550 | Ala | Glu | Gly | Ala | Thr 555 | Cys | Gln | Ala | Tyr | Glu 560 |
| Leu | Ala | Asp | Tyr | Ser 565 | Asn | Leu | Arg | Glu | Thr 570 | Asp | Ile |

( 2 ) INFORMATION FOR SEQ ID NO:3:

( i ) SEQUENCE CHARACTERISTICS:
        ( A ) LENGTH: 1738 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: N ( i v ) ANTI-SENSE: N ( i x ) FEATURE:
  ( A ) NAME/KEY: CDS
  ( B ) LOCATION: 124..1683
  ( D ) OTHER INFORMATION:

( x i ) SEQUENCE DESCRIPTION: SEQ ID NO:3:

```
GCCAGGAGGG CGCCTCTGGG AAGAAGACCA CGGGGGAAGC AAAGTTTCAG GGCAGCTGAG      60

GAGCCTTCGC CGCAGCCCTT CCGAGCCCAA TCATCCCCCA GGCTATGGAG GGCGGACTCT     120

AAG ATG AAT CCC GAC CTG GAC ACC GGC CAC AAC ACA TCA GCA CCT GCC      168
    Met Asn Pro Asp Leu Asp Thr Gly His Asn Thr Ser Ala Pro Ala
    1           5                   10                  15

CAC TGG GGA GAG TTG AAA AAT GCC AAC TTC ACT GGC CCC AAC CAG ACC      216
His Trp Gly Glu Leu Lys Asn Ala Asn Phe Thr Gly Pro Asn Gln Thr
                20                  25                  30

TCG AGC AAC TCC ACA CTG CCC CAG CTG GAC ATC ACC AGG GCC ATC TCT      264
Ser Ser Asn Ser Thr Leu Pro Gln Leu Asp Ile Thr Arg Ala Ile Ser
            35                  40                  45

GTG GGC CTG GTG CTG GGC GCC TTC ATC CTC TTT GCC ATC GTG GGC AAC      312
Val Gly Leu Val Leu Gly Ala Phe Ile Leu Phe Ala Ile Val Gly Asn
        50                  55                  60

ATC CTA GTC ATC TTG TCT GTG GCC TGC AAC CGG CAC CTG CGG ACG CCC      360
Ile Leu Val Ile Leu Ser Val Ala Cys Asn Arg His Leu Arg Thr Pro
    65                  70                  75

ACC AAC TAC TTC ATT GTC AAC CTG GCC ATG GCC GAC CTG CTG TTG AGC      408
Thr Asn Tyr Phe Ile Val Asn Leu Ala Met Ala Asp Leu Leu Leu Ser
80                  85                  90                  95

TTC ACC GTC CTG CCC TTC TCA GCG GCC CTA GAG GTG CTC GGC TAC TGG      456
Phe Thr Val Leu Pro Phe Ser Ala Ala Leu Glu Val Leu Gly Tyr Trp
                100                 105                 110

GTG CTG GGG CGG ATC TTC TGT GAC ATC TGG GCA GCC GTG GAT GTC CTG      504
Val Leu Gly Arg Ile Phe Cys Asp Ile Trp Ala Ala Val Asp Val Leu
            115                 120                 125

TGC TGC ACA GCG TCC ATT CTG AGC CTG TGC GCC ATC TCC ATC GAT CGC      552
Cys Cys Thr Ala Ser Ile Leu Ser Leu Cys Ala Ile Ser Ile Asp Arg
        130                 135                 140

TAC ATC GGG GTG CGC TAC TCT CTG CAG TAT CCC ACG CTG GTC ACC CGG      600
Tyr Ile Gly Val Arg Tyr Ser Leu Gln Tyr Pro Thr Leu Val Thr Arg
    145                 150                 155

AGG AAG GCC ATC TTG GCG CTG CTC AGT GTC TGG GTC TTG TCC ACC GTC      648
Arg Lys Ala Ile Leu Ala Leu Leu Ser Val Trp Val Leu Ser Thr Val
160                 165                 170                 175

ATC TCC ATC GGG CCT CTC CTT GGG TGG AAG GAG CCG GCA CCC AAC GAT      696
Ile Ser Ile Gly Pro Leu Leu Gly Trp Lys Glu Pro Ala Pro Asn Asp
                180                 185                 190

GAC AAG GAG TGC GGG GTC ACC GAA GAA CCC TTC TAT GCC CTC TTC TCC      744
Asp Lys Glu Cys Gly Val Thr Glu Glu Pro Phe Tyr Ala Leu Phe Ser
            195                 200                 205

TCT CTG GGC TCC TTC TAC ATC CCT CTG GCG GTC ATT CTA GTC ATG TAC      792
Ser Leu Gly Ser Phe Tyr Ile Pro Leu Ala Val Ile Leu Val Met Tyr
        210                 215                 220

TGC CGT GTC TAT ATA GTG GCC AAG AGA ACC ACC AAG AAC CTA GAG GCA      840
Cys Arg Val Tyr Ile Val Ala Lys Arg Thr Thr Lys Asn Leu Glu Ala
    225                 230                 235

GGA GTC ATG AAG GAG ATG TCC AAC TCC AAG GAG CTG ACC CTG AGG ATC      888
Gly Val Met Lys Glu Met Ser Asn Ser Lys Glu Leu Thr Leu Arg Ile
240                 245                 250                 255

CAT TCC AAG AAC TTT CAC GAG GAC ACC CTT AGC AGT ACC AAG GCC AAG      936
His Ser Lys Asn Phe His Glu Asp Thr Leu Ser Ser Thr Lys Ala Lys
                260                 265                 270
```

```
GGC  CAC  AAC  CCC  AGG  AGT  TCC  ATA  GCT  GTC  AAA  CTT  TTT  AAG  TTC  TCC        984
Gly  His  Asn  Pro  Arg  Ser  Ser  Ile  Ala  Val  Lys  Leu  Phe  Lys  Phe  Ser
               275                 280                      285

AGG  GAA  AAG  AAA  GCA  GCT  AAG  ACG  TTG  GGC  ATT  GTG  GTC  GGT  ATG  TTC       1032
Arg  Glu  Lys  Lys  Ala  Ala  Lys  Thr  Leu  Gly  Ile  Val  Val  Gly  Met  Phe
               290                 295                      300

ATC  TTG  TGC  TGG  CTA  CCC  TTC  TTC  ATC  GCT  CTA  CCG  CTT  GGC  TCC  TTG       1080
Ile  Leu  Cys  Trp  Leu  Pro  Phe  Phe  Ile  Ala  Leu  Pro  Leu  Gly  Ser  Leu
     305                      310                      315

TTC  TCC  ACC  CTG  AAG  CCC  CCC  GAC  GCC  GTG  TTC  AAG  GTG  GTG  TTC  TGG       1128
Phe  Ser  Thr  Leu  Lys  Pro  Pro  Asp  Ala  Val  Phe  Lys  Val  Val  Phe  Trp
320                      325                      330                      335

CTG  GGC  TAC  TTC  AAC  AGC  TGC  CTC  AAC  CCC  ATC  ATC  TAC  CCA  TGC  TCC       1176
Leu  Gly  Tyr  Phe  Asn  Ser  Cys  Leu  Asn  Pro  Ile  Ile  Tyr  Pro  Cys  Ser
                    340                      345                      350

AGC  AAG  GAG  TTC  AAG  CGC  GCT  TTC  GTG  CGC  ATC  CTC  GGG  TGC  CAG  TGC       1224
Ser  Lys  Glu  Phe  Lys  Arg  Ala  Phe  Val  Arg  Ile  Leu  Gly  Cys  Gln  Cys
               355                      360                      365

CGC  GGC  CGC  GGC  CGC  CGC  CGA  CGC  CGC  CGC  CGT  CGC  CTG  GGC  GGC            1272
Arg  Gly  Arg  Gly  Arg  Arg  Arg  Arg  Arg  Arg  Arg  Arg  Leu  Gly  Gly
          370                      375                      380

TGC  GCC  TAC  ACC  TAC  CGG  CCG  TGG  ACG  CGC  GGC  GGC  TCG  CTG  GAG  CGC       1320
Cys  Ala  Tyr  Thr  Tyr  Arg  Pro  Trp  Thr  Arg  Gly  Gly  Ser  Leu  Glu  Arg
385                      390                      395

TCG  CAG  TCG  CGC  AAG  GAC  TCG  CTG  GAC  GAC  AGC  GGC  AGC  TGC  CTG  AGC       1368
Ser  Gln  Ser  Arg  Lys  Asp  Ser  Leu  Asp  Asp  Ser  Gly  Ser  Cys  Leu  Ser
400                      405                      410                      415

GGC  AGC  CAG  CGG  ACC  CTG  CCC  TCG  GCC  TCG  CCG  AGC  CCG  GGC  TAC  CTG       1416
Gly  Ser  Gln  Arg  Thr  Leu  Pro  Ser  Ala  Ser  Pro  Ser  Pro  Gly  Tyr  Leu
                    420                      425                      430

GGC  CGC  GGC  GCG  CCA  CCG  CCA  GTC  GAG  CTG  TGC  GCC  TTC  CCC  GAG  TGG       1464
Gly  Arg  Gly  Ala  Pro  Pro  Pro  Val  Glu  Leu  Cys  Ala  Phe  Pro  Glu  Trp
               435                      440                      445

AAG  GCG  CCC  GGC  GCC  CTC  CTG  AGC  CTG  CCC  GCG  CCT  GAG  CCC  CCC  GGC       1512
Lys  Ala  Pro  Gly  Ala  Leu  Leu  Ser  Leu  Pro  Ala  Pro  Glu  Pro  Pro  Gly
          450                      455                      460

CGC  CGC  GGC  CGC  CAC  GAC  TCG  GGC  CCG  CTC  TTC  ACC  TTC  AAG  CTC  CTG       1560
Arg  Arg  Gly  Arg  His  Asp  Ser  Gly  Pro  Leu  Phe  Thr  Phe  Lys  Leu  Leu
465                      470                      475

ACC  GAG  CCC  GAG  AGC  CCC  GGG  ACC  GAC  GGC  GGC  GCC  AGC  AAC  GGA  GGC       1608
Thr  Glu  Pro  Glu  Ser  Pro  Gly  Thr  Asp  Gly  Gly  Ala  Ser  Asn  Gly  Gly
480                      485                      490                      495

TGC  GAG  GCC  GCG  GCC  GAC  GTG  GCC  AAC  GGG  CAG  CCG  GGC  TTC  AAA  AGC       1656
Cys  Glu  Ala  Ala  Ala  Asp  Val  Ala  Asn  Gly  Gln  Pro  Gly  Phe  Lys  Ser
                    500                      505                      510

AAC  ATG  CCC  CTG  GCG  CCC  GGG  CAG  TTT  TAGGGCCCCC  GTGCGCAGCT                  1703
Asn  Met  Pro  Leu  Ala  Pro  Gly  Gln  Phe
               515                 520

TTCTTTCCCT  GGGGAGGAAA  ACATCGTGGG  GGGGA                                            1738
```

( 2 ) INFORMATION FOR SEQ ID NO:4:

( i ) SEQUENCE CHARACTERISTICS:
        ( A ) LENGTH: 520 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

Met  Asn  Pro  Asp  Leu  Asp  Thr  Gly  His  Asn  Thr  Ser  Ala  Pro  Ala  His

-continued

```
  1                    5                         10                        15

Trp Gly Glu Leu Lys Asn Ala Asn Phe Thr Gly Pro Asn Gln Thr Ser
             20                   25                  30

Ser Asn Ser Thr Leu Pro Gln Leu Asp Ile Thr Arg Ala Ile Ser Val
             35                   40                  45

Gly Leu Val Leu Gly Ala Phe Ile Leu Phe Ala Ile Val Gly Asn Ile
             50                   55                  60

Leu Val Ile Leu Ser Val Ala Cys Asn Arg His Leu Arg Thr Pro Thr
 65                   70                  75                   80

Asn Tyr Phe Ile Val Asn Leu Ala Met Ala Asp Leu Leu Leu Ser Phe
                 85                  90                  95

Thr Val Leu Pro Phe Ser Ala Ala Leu Glu Val Leu Gly Tyr Trp Val
             100                  105                 110

Leu Gly Arg Ile Phe Cys Asp Ile Trp Ala Ala Val Asp Val Leu Cys
             115                  120                 125

Cys Thr Ala Ser Ile Leu Ser Leu Cys Ala Ile Ser Ile Asp Arg Tyr
     130                  135                  140

Ile Gly Val Arg Tyr Ser Leu Gln Tyr Pro Thr Leu Val Thr Arg Arg
145                  150                  155                 160

Lys Ala Ile Leu Ala Leu Leu Ser Val Trp Val Leu Ser Thr Val Ile
                 165                  170                 175

Ser Ile Gly Pro Leu Leu Gly Trp Lys Glu Pro Ala Pro Asn Asp Asp
             180                  185                 190

Lys Glu Cys Gly Val Thr Glu Glu Pro Phe Tyr Ala Leu Phe Ser Ser
     195                  200                  205

Leu Gly Ser Phe Tyr Ile Pro Leu Ala Val Ile Leu Val Met Tyr Cys
     210                  215                  220

Arg Val Tyr Ile Val Ala Lys Arg Thr Thr Lys Asn Leu Glu Ala Gly
225                  230                  235                 240

Val Met Lys Glu Met Ser Asn Ser Lys Glu Leu Thr Leu Arg Ile His
                 245                  250                 255

Ser Lys Asn Phe His Glu Asp Thr Leu Ser Ser Thr Lys Ala Lys Gly
             260                  265                 270

His Asn Pro Arg Ser Ser Ile Ala Val Lys Leu Phe Lys Phe Ser Arg
         275                  280                 285

Glu Lys Lys Ala Ala Lys Thr Leu Gly Ile Val Val Gly Met Phe Ile
     290                  295                  300

Leu Cys Trp Leu Pro Phe Phe Ile Ala Leu Pro Leu Gly Ser Leu Phe
305                  310                  315                 320

Ser Thr Leu Lys Pro Pro Asp Ala Val Phe Lys Val Val Phe Trp Leu
             325                  330                 335

Gly Tyr Phe Asn Ser Cys Leu Asn Pro Ile Ile Tyr Pro Cys Ser Ser
             340                  345                 350

Lys Glu Phe Lys Arg Ala Phe Val Arg Ile Leu Gly Cys Gln Cys Arg
     355                  360                  365

Gly Arg Gly Arg Arg Arg Arg Arg Arg Arg Leu Gly Gly Cys
     370                  375                  380                 Cys

Ala Tyr Thr Tyr Arg Pro Trp Thr Arg Gly Gly Ser Leu Glu Arg Ser
385                  390                  395                 400

Gln Ser Arg Lys Asp Ser Leu Asp Asp Ser Gly Ser Cys Leu Ser Gly
                 405                  410                 415

Ser Gln Arg Thr Leu Pro Ser Ala Ser Pro Ser Pro Gly Tyr Leu Gly
             420                  425                 430
```

5,714,381

-continued

| Arg | Gly | Ala | Pro | Pro | Pro | Val | Glu | Leu | Cys | Ala | Phe | Pro | Glu | Trp | Lys |
|---|---|---|---|---|---|---|---|---|---|---|---|---|---|---|---|
| | | 435 | | | | 440 | | | | | 445 | | | | |

| Ala | Pro | Gly | Ala | Leu | Leu | Ser | Leu | Pro | Ala | Pro | Glu | Pro | Pro | Gly | Arg |
|---|---|---|---|---|---|---|---|---|---|---|---|---|---|---|---|
| 450 | | | | | 455 | | | | | 460 | | | | | |

| Arg | Gly | Arg | His | Asp | Ser | Gly | Pro | Leu | Phe | Thr | Phe | Lys | Leu | Leu | Thr |
|---|---|---|---|---|---|---|---|---|---|---|---|---|---|---|---|
| 465 | | | | 470 | | | | 475 | | | | | | 480 | |

| Glu | Pro | Glu | Ser | Pro | Gly | Thr | Asp | Gly | Gly | Ala | Ser | Asn | Gly | Gly | Cys |
|---|---|---|---|---|---|---|---|---|---|---|---|---|---|---|---|
| | | | | 485 | | | | | 490 | | | | | 495 | |

| Glu | Ala | Ala | Ala | Asp | Val | Ala | Asn | Gly | Gln | Pro | Gly | Phe | Lys | Ser | Asn |
|---|---|---|---|---|---|---|---|---|---|---|---|---|---|---|---|
| | | | 500 | | | | | 505 | | | | 510 | | | |

| Met | Pro | Leu | Ala | Pro | Gly | Gln | Phe |
|---|---|---|---|---|---|---|---|
| | 515 | | | | | 520 | |

(2) INFORMATION FOR SEQ ID NO:5:

(i) SEQUENCE CHARACTERISTICS:
    (A) LENGTH: 1639 base pairs
    (B) TYPE: nucleic acid
    (C) STRANDEDNESS: single
    (D) TOPOLOGY: unknown (ii) MOLECULE TYPE: DNA (genomic)

(iii) HYPOTHETICAL: N (iv) ANTI-SENSE: N (ix) FEATURE:
    (A) NAME/KEY: CDS
    (B) LOCATION: 126..1523
    (D) OTHER INFORMATION:

(xi) SEQUENCE DESCRIPTION: SEQ ID NO:5:

```
CCAGCCAAAC CACTGGCAGG CTCCCTCCAG CCGAGACCTT TTATTCCCGG CTCCCGAGCT        60

CCGCCTCCGC GCCAGCCGG GAGGTGGCCC TGACAGCCGG ACCTCGCCCG GCCCCGGCTG       120

GGACC ATG GTG TTT CTC TCG GGA AAT GCT TCC GAC AGC TCC AAC TGC          167
      Met Val Phe Leu Ser Gly Asn Ala Ser Asp Ser Ser Asn Cys
      1               5                   10

ACC CAA CCG CCG GCA CCG GTG AAC ATT TCC AAG GCC ATT CTG CTC GGG        215
Thr Gln Pro Pro Ala Pro Val Asn Ile Ser Lys Ala Ile Leu Leu Gly
    15              20                  25                  30

GTG ATC TTG GGG GGC CTC ATT CTT TTC GGG GTG CTG GGT AAC ATC CTA        263
Val Ile Leu Gly Gly Leu Ile Leu Phe Gly Val Leu Gly Asn Ile Leu
                35                  40                  45

GTG ATC CTC TCC GTA GCC TGT CAC CGA CAC CTG CAC TCA GTC ACG CAC        311
Val Ile Leu Ser Val Ala Cys His Arg His Leu His Ser Val Thr His
            50                  55                  60

TAC TAC ATC GTC AAC CTG GCG GTG GCC GAC CTC CTG CTC ACC TCC ACG        359
Tyr Tyr Ile Val Asn Leu Ala Val Ala Asp Leu Leu Leu Thr Ser Thr
        65                  70                  75

GTG CTG CCC TTC TCC GCC ATC TTC GAG GTC CTA GGC TAC TGG GCC TTC        407
Val Leu Pro Phe Ser Ala Ile Phe Glu Val Leu Gly Tyr Trp Ala Phe
    80                  85                  90

GGC AGG GTC TTC TGC AAC ATC TGG GCG GCA GTG GAT GTG CTG TGC TGC        455
Gly Arg Val Phe Cys Asn Ile Trp Ala Ala Val Asp Val Leu Cys Cys
95                  100                 105                 110

ACC GCG TCC ATC ATG GGC CTC TGC ATC ATC TCC ATC GAC CGC TAC ATC        503
Thr Ala Ser Ile Met Gly Leu Cys Ile Ile Ser Ile Asp Arg Tyr Ile
                115                 120                 125

GGC GTG AGC TAC CCG CTG CGC TAC CCA ACC ATC GTC ACC CAG AGG AGG        551
Gly Val Ser Tyr Pro Leu Arg Tyr Pro Thr Ile Val Thr Gln Arg Arg
            130                 135                 140
```

```
GGT CTC ATG GCT CTG CTC TGC GTC TGG GCA CTC TCC CTG GTC ATA TCC      599
Gly Leu Met Ala Leu Leu Cys Val Trp Ala Leu Ser Leu Val Ile Ser
        145             150             155

ATT GGA CCC CTG TTC GGC TGG AGG CAG CCG GCC CCC GAG GAC GAG ACC      647
Ile Gly Pro Leu Phe Gly Trp Arg Gln Pro Ala Pro Glu Asp Glu Thr
    160             165             170

ATC TGC CAG ATC AAC GAG GAG CCG GGC TAC GTG CTC TTC TCA GCG CTG      695
Ile Cys Gln Ile Asn Glu Glu Pro Gly Tyr Val Leu Phe Ser Ala Leu
175             180             185             190

GGC TCC TTC TAC CTG CCT CTG GCC ATC ATC CTG GTC ATG TAC TGC CGC      743
Gly Ser Phe Tyr Leu Pro Leu Ala Ile Ile Leu Val Met Tyr Cys Arg
                195             200             205

GTC TAC GTG GTG GCC AAG AGG GAG AGC CGG GGC CTC AAG TCT GGC CTC      791
Val Tyr Val Val Ala Lys Arg Glu Ser Arg Gly Leu Lys Ser Gly Leu
            210             215             220

AAG ACC GAC AAG TCG GAC TCG GAG CAA GTG ACG CTC CGC ATC CAT CGG      839
Lys Thr Asp Lys Ser Asp Ser Glu Gln Val Thr Leu Arg Ile His Arg
        225             230             235

AAA AAC GCC CCG GCA GGA GGC AGC GGG ATG GCC AGC GCC AAG ACC AAG      887
Lys Asn Ala Pro Ala Gly Gly Ser Gly Met Ala Ser Ala Lys Thr Lys
    240             245             250

ACG CAC TTC TCA GTG AGG CTC CTC AAG TTC TCC CGG GAG AAG AAA GCG      935
Thr His Phe Ser Val Arg Leu Leu Lys Phe Ser Arg Glu Lys Lys Ala
255             260             265             270

GCC AAA ACG CTG GGC ATC GTG GTC GGC TGC TTC GTC CTC TGC TGG CTG      983
Ala Lys Thr Leu Gly Ile Val Val Gly Cys Phe Val Leu Cys Trp Leu
                275             280             285

CCT TTT TTC TTA GTC ATG CCC ATT GGG TCT TTC TTC CCT GAT TTC AAG     1031
Pro Phe Phe Leu Val Met Pro Ile Gly Ser Phe Phe Pro Asp Phe Lys
            290             295             300

CCC TCT GAA ACA GTT TTT AAA ATA GTA TTT TGG CTC GGA TAT CTA AAC     1079
Pro Ser Glu Thr Val Phe Lys Ile Val Phe Trp Leu Gly Tyr Leu Asn
        305             310             315

AGC TGC ATC AAC CCC ATC ATA TAC CCA TGC TCC AGC CAA GAG TTC AAA     1127
Ser Cys Ile Asn Pro Ile Ile Tyr Pro Cys Ser Ser Gln Glu Phe Lys
    320             325             330

AAG GCC TTT CAG AAT GTC TTG AGA ATC CAG TGT CTC TGC AGA AAG CAG     1175
Lys Ala Phe Gln Asn Val Leu Arg Ile Gln Cys Leu Cys Arg Lys Gln
335             340             345             350

TCT TCC AAA CAT GCC CTG GGC TAC ACC CTG CAC CCG CCC AGC CAG GCC     1223
Ser Ser Lys His Ala Leu Gly Tyr Thr Leu His Pro Pro Ser Gln Ala
                355             360             365

GTG GAA GGG CAA CAC AAG GAC ATG GTG CGC ATC CCC GTG GGA TCA AGA     1271
Val Glu Gly Gln His Lys Asp Met Val Arg Ile Pro Val Gly Ser Arg
            370             375             380

GAG ACC TTC TAC AGG ATC TCC AAG ACG GAT GGC GTT TGT GAA TGG AAA     1319
Glu Thr Phe Tyr Arg Ile Ser Lys Thr Asp Gly Val Cys Glu Trp Lys
        385             390             395

TTT TTC TCT TCC ATG CCC CGT GGA TCT GCC AGG ATT ACA GTG TCC AAA     1367
Phe Phe Ser Ser Met Pro Arg Gly Ser Ala Arg Ile Thr Val Ser Lys
    400             405             410

GAC CAA TCC TCC TGT ACC ACA GCC CGG GTG AGA AGT AAA AGC TTT TTG     1415
Asp Gln Ser Ser Cys Thr Thr Ala Arg Val Arg Ser Lys Ser Phe Leu
415             420             425             430

CAG GTC TGC TGC TGT GTA GGG CCC TCA ACC CCC AGC CTT GAC AAG AAC     1463
Gln Val Cys Cys Cys Val Gly Pro Ser Thr Pro Ser Leu Asp Lys Asn
                435             440             445

CAT CAA GTT CCA ACC ATT AAG GTC CAC ACC ATC TCC CTC AGT GAG AAC     1511
His Gln Val Pro Thr Ile Lys Val His Thr Ile Ser Leu Ser Glu Asn
            450             455             460
```

```
GGG GAG GAA GTC TAGGACAGGA AAGATGCAGA GGAAAGGGGA ATATCTTAGG         1563
Gly Glu Glu Val
            465

TACCATACCC TGGAGTTCTA GAGGATTCCT CGACAAGCTT ATTCCGATCC AGACATGATA   1623

GATACATTGA TGAGTT                                                   1639
```

( 2 ) INFORMATION FOR SEQ ID NO:6:

( i ) SEQUENCE CHARACTERISTICS:
        ( A ) LENGTH: 466 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Val Phe Leu Ser Gly Asn Ala Ser Asp Ser Ser Asn Cys Thr Gln
 1           5                  10                  15

Pro Pro Ala Pro Val Asn Ile Ser Lys Ala Ile Leu Leu Gly Val Ile
            20                  25                  30

Leu Gly Gly Leu Ile Leu Phe Gly Val Leu Gly Asn Ile Leu Val Ile
            35                  40                  45

Leu Ser Val Ala Cys His Arg His Leu His Ser Val Thr His Tyr Tyr
50                      55                  60

Ile Val Asn Leu Ala Val Ala Asp Leu Leu Leu Thr Ser Thr Val Leu
65                  70                  75                  80

Pro Phe Ser Ala Ile Phe Glu Val Leu Gly Tyr Trp Ala Phe Gly Arg
                    85                  90                  95

Val Phe Cys Asn Ile Trp Ala Ala Val Asp Val Leu Cys Cys Thr Ala
                100                 105                 110

Ser Ile Met Gly Leu Cys Ile Ile Ser Ile Asp Arg Tyr Ile Gly Val
            115                 120                 125

Ser Tyr Pro Leu Arg Tyr Pro Thr Ile Val Thr Gln Arg Arg Gly Leu
    130                 135                 140

Met Ala Leu Leu Cys Val Trp Ala Leu Ser Leu Val Ile Ser Ile Gly
145                 150                 155                 160

Pro Leu Phe Gly Trp Arg Gln Pro Ala Pro Glu Asp Glu Thr Ile Cys
                165                 170                 175

Gln Ile Asn Glu Glu Pro Gly Tyr Val Leu Phe Ser Ala Leu Gly Ser
            180                 185                 190

Phe Tyr Leu Pro Leu Ala Ile Ile Leu Val Met Tyr Cys Arg Val Tyr
    195                 200                 205

Val Val Ala Lys Arg Glu Ser Arg Gly Leu Lys Ser Gly Leu Lys Thr
210                 215                 220

Asp Lys Ser Asp Ser Glu Gln Val Thr Leu Arg Ile His Arg Lys Asn
225                 230                 235                 240

Ala Pro Ala Gly Gly Ser Gly Met Ala Ser Ala Lys Thr Lys Thr His
                245                 250                 255

Phe Ser Val Arg Leu Leu Lys Phe Ser Arg Glu Lys Lys Ala Ala Lys
            260                 265                 270

Thr Leu Gly Ile Val Val Gly Cys Phe Val Leu Cys Trp Leu Pro Phe
            275                 280                 285

Phe Leu Val Met Pro Ile Gly Ser Phe Phe Pro Asp Phe Lys Pro Ser
            290                 295                 300

Glu Thr Val Phe Lys Ile Val Phe Trp Leu Gly Tyr Leu Asn Ser Cys
305                 310                 315                 320
```

| | | | | | | | | | | | | | | | |
|---|---|---|---|---|---|---|---|---|---|---|---|---|---|---|---|
| Ile | Asn | Pro | Ile | Ile 325 | Tyr | Pro | Cys | Ser | Ser 330 | Gln | Glu | Phe | Lys | Lys 335 | Ala |
| Phe | Gln | Asn | Val 340 | Leu | Arg | Ile | Gln | Cys 345 | Leu | Cys | Arg | Lys | Gln 350 | Ser | Ser |
| Lys | His | Ala 355 | Leu | Gly | Tyr | Thr | Leu 360 | His | Pro | Pro | Ser | Gln 365 | Ala | Val | Glu |
| Gly | Gln 370 | His | Lys | Asp | Met | Val 375 | Arg | Ile | Pro | Val | Gly 380 | Ser | Arg | Glu | Thr |
| Phe 385 | Tyr | Arg | Ile | Ser | Lys 390 | Thr | Asp | Gly | Val | Cys 395 | Glu | Trp | Lys | Phe | Phe 400 |
| Ser | Ser | Met | Pro | Arg 405 | Gly | Ser | Ala | Arg | Ile 410 | Thr | Val | Ser | Lys | Asp 415 | Gln |
| Ser | Ser | Cys | Thr 420 | Thr | Ala | Arg | Val | Arg 425 | Ser | Lys | Ser | Phe | Leu 430 | Gln | Val |
| Cys | Cys | Cys 435 | Val | Gly | Pro | Ser | Thr 440 | Pro | Ser | Leu | Asp | Lys 445 | Asn | His | Gln |
| Val | Pro 450 | Thr | Ile | Lys | Val | His 455 | Thr | Ile | Ser | Leu | Ser 460 | Glu | Asn | Gly | Glu |
| Glu 465 | Val | | | | | | | | | | | | | | |